United States Patent
Kinsella et al.

(10) Patent No.: US 9,738,599 B2
(45) Date of Patent: *Aug. 22, 2017

(54) THROMBOXANE RECEPTOR ANTAGONISTS

(71) Applicant: UNIVERSITY COLLEGE DUBLIN, NATIONAL UNIVERSITY OF IRELAND, DUBLIN, Belfield (IE)

(72) Inventors: B. Therese Kinsella, Dublin (IE); Patrick Guiry, Dublin (IE); Helen Reid, Dublin (IE); Barry O'Connor, Dublin (IE)

(73) Assignee: UNIVERSITY COLLEGE DUBLIN, NATIONAL UNIVERSITY OF IRELAND, DUBLIN, Belfield (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/460,910

(22) Filed: Mar. 16, 2017

(65) Prior Publication Data

US 2017/0183300 A1    Jun. 29, 2017

Related U.S. Application Data

(63) Continuation of application No. 15/349,379, filed on Nov. 11, 2016, now Pat. No. 9,630,915, which is a continuation of application No. 15/178,931, filed on Jun. 10, 2016, now Pat. No. 9,522,877, which is a continuation of application No. 14/391,856, filed as application No. PCT/IB2013/001258 on Apr. 17, 2013, now Pat. No. 9,388,127.

(60) Provisional application No. 61/625,516, filed on Apr. 17, 2012, provisional application No. 61/625,537, filed on Apr. 17, 2012, provisional application No. 61/625,540, filed on Apr. 17, 2012.

(51) Int. Cl.
     *C07C 311/58*     (2006.01)

(52) U.S. Cl.
     CPC ................. *C07C 311/58* (2013.01)

(58) Field of Classification Search
     CPC ... C07C 311/56; C07C 311/57; C07C 311/58; C07C 311/59
     See application file for complete search history.

(56) References Cited

U.S. PATENT DOCUMENTS

| | | |
|---|---|---|
| 3,556,764 A | 1/1971 | Hamm |
| 3,714,209 A | 1/1973 | Tung et al. |
| 4,166,452 A | 9/1979 | Generales, Jr. |
| 4,256,108 A | 3/1981 | Theeuwes |
| 4,265,874 A | 5/1981 | Bonsen et al. |
| 5,434,124 A | 7/1995 | Mayer et al. |
| 5,697,967 A | 12/1997 | Dinh et al. |
| 6,136,157 A | 10/2000 | Lindeberg et al. |
| 6,214,841 B1 | 4/2001 | Jackson et al. |
| 6,231,600 B1 | 5/2001 | Zhong |
| 6,352,552 B1 | 3/2002 | Levinson et al. |
| 6,583,307 B2 | 6/2003 | Nolan et al. |
| 6,796,998 B2 | 9/2004 | Schaldach et al. |
| 7,135,038 B1 | 11/2006 | Limon |
| 7,618,949 B2 | 11/2009 | Boyer et al. |
| 7,713,538 B2 | 5/2010 | Lewis et al. |
| 7,833,544 B2 | 11/2010 | Lewis et al. |
| 7,947,302 B2 | 5/2011 | Falotico et al. |
| 8,486,994 B2 | 7/2013 | Alberts et al. |
| 8,710,252 B2 | 4/2014 | Pace-Asciak et al. |
| 9,388,127 B2 | 7/2016 | Kinsella et al. |
| 2003/0232877 A1 | 12/2003 | Sikorski et al. |
| 2004/0213818 A1 | 10/2004 | Kashiwabara et al. |
| 2005/0010279 A1 | 1/2005 | Tenerz et al. |
| 2005/0015136 A1 | 1/2005 | Ikeuchi et al. |
| 2005/0025705 A1 | 2/2005 | Wang |
| 2005/0043788 A1 | 2/2005 | Luo et al. |
| 2005/0152943 A1 | 7/2005 | Hezi-Yamit et al. |
| 2006/0122143 A1 | 6/2006 | Boyer et al. |
| 2007/0168015 A1 | 7/2007 | Momma et al. |
| 2009/0062904 A1 | 3/2009 | Furst |
| 2009/0311299 A1 | 12/2009 | Falotico et al. |
| 2010/0023115 A1 | 1/2010 | Robaina et al. |
| 2011/0099785 A1 | 5/2011 | Pacetti |
| 2016/0102051 A1 | 4/2016 | Kinsella et al. |

FOREIGN PATENT DOCUMENTS

| | | |
|---|---|---|
| WO | 00/42004 A1 | 7/2000 |
| WO | 2009/089098 A1 | 7/2009 |
| WO | 2011/057262 A2 | 5/2011 |
| WO | 2013/156871 A2 | 10/2013 |

OTHER PUBLICATIONS

Bambi-Nyanguile, 2013, Synthesis and pharmacological evaluation of 2-aryloxy/arylamino-5-cyanobenzenesulfonyl ureas as novel thromboxane A2 receptor antagonists, Eur J Med Chem 65:32-40.

Born et al., 1963, The Aggregation of Blood Platelets, J. Physiol 168:178-95.

Bousser et al., 2009, Rationale and design of a randomized, double-blind, parallel-group study of terutroban 30; mg/day versus aspirin 100 mg/day in stroke patients: the prevention of cerebrovascular and; cardiovascular events of schemic origin with terutroban in patients with a history of ischemic; stroke or transient ischemic attack (PERFORM) study, PERFORM Study Investigators. Cerebrovasc Dis. 27(5):509-18.

(Continued)

*Primary Examiner* — Craig Ricci
*Assistant Examiner* — Christopher R Stone
(74) *Attorney, Agent, or Firm* — Brown Rudnick LLP; Thomas C. Meyers

(57) ABSTRACT

The invention generally relates to compounds that function as TP antagonists for treating thrombosis and other cardiovascular, renal, or pulmonary diseases. In some embodiments, the invention provides a compound including a substituted nitro phenoxy phenyl, a sulfonylurea, and an alkyl group. In some embodiments, the invention provides a method of treating thrombosis by administering an antithrombotic compound that preferentially binds to a thromboxane receptor, has preferential binding for either TPalpha (TPα) or TPbeta (TPβ) receptor subtype.

10 Claims, 7 Drawing Sheets

(56) References Cited

OTHER PUBLICATIONS

Bousser et al., 2011, Terutroban versus aspirin in patients with cerebral ischaemic events (PERFORM): a; randomised, double-blind, parallel-group trial, PERFORM Study Investigators. Lancet. 11;377(9782):2013-22. Epub May 25, 2011. Erratum in: Lancet. Jul. 30, 2011;378(9789):402.
Bousser et al., 2009, The Prevention of cerebrovascular and cardiovascular events of ischemic origin with terutroban in patients with a history of ischemic stroke or transient ischemic attack (PERFORM) study: baseline characteristics of the population, PERFORM Study Investigators. Cerebrovasc Dis. 27(6):608-13.
Cherdon et al., 2011, BM-573 inhibits the development of early atherosclerotic lesions in Apo E deficient mice by; blocking TP receptors and thromboxane synthase, Prostaglandins Other Lipid Mediat. 94:124-32.
Choi et al., 2011, New therapeutic approaches to combat arterial thrombosis: better drugs for old targets,; novel targets, and future prospects, Mol Interv. 11(2):111-23.
Custodi et al., 2012, Filling the complexity of GPCRs modulation into simple hypotheses of ligand design, Journal of Molecular Graphics and Modelling 38:70-81.
Dogne et al., 2004, Pharmacological Characterization ofN-tert-Butyl-N-[2-(4-methylphenylamino)-5-nitrobenzenesulfonyl]urea (BM-573), a; Novel Thromboxane A2Receptor Antagonist and Thromboxane; Synthase Inhibitor in a Rat Model of Arterial Thrombosis and; Its Effects on Bleeding Time, JPET 309(2):498-505.
Fiessinger et al., 2010, Thromboxane Antagonism with terutroban in Peripheral Arterial Disease: the TAIPAD; study, TAIPAD investigators. J Thromb Haemost. 8(11):2369-76.
Ghuysen et al., 2005, Pharmacological profile and therapeutic potential of BM-573, a combined thromboxane; receptor antagonist and synthase inhibitor, Cardiovasc Drug Rev. 23(1):1-14.
Hanson et al., 2005, In vitro and in vivo pharmacological characterization of BM-613 [N-n-pentyl-N-[2-(4-methylphenylamino)-5-nitrobenzenesulfonyl]urea, a novel dual thromboxane synthase inhibitor and thromboxane receptor antagonist, The Journal of Phramacology and Experimental Therapeutics 313(1):293-301.
Hanson et al., 2006, Synthesis and Pharmacological Evaluation of Novel Nitrobenzenic Thromboxane Modulators as Antiplatelet Agents Acting on Both the Alpha and Beta Isoforms of the Human Thromboxane Receptor, Journal of Medicinal Chemistry 49(12):3701-3709.
Hanson et al., 2007, Design, Synthesis, and SAR study of a Series of N-Alkyl-N'-[2-(aryloxy)-5-nitrobenzenesulfonyl]ureas and-cyanoguanidine as Selective Antagonists of the TP[alpha] and TP[beta] Isoforms of the Human Thromboxane A2 Receptor, Journal of Medicinal Chemistry 50(16):3928-3936.
Hirata et al., 2011, Prostanoid receptors, Chemical Reviews 111:6209-6230.
International Search Report and Written Opinion mailed on May 9, 2014, for International Patent Application No. PCT/IB2013/001258, filed Apr. 17, 2013 (22 pages).
International Search Report and Written Opinion mailed on Oct. 11, 2013, for International Patent Application No. PCT/IB2013/001104, filed Apr. 17, 2013 (17 pages).
Jenkins et al., 2005, Bioluminescent human breast cancer cell lines that permit rapid and sensitive in vivo detection of mammary tumors and multiple metastases in immune deficient mice, Breast Cancer Res 7:444-454.
Kassack et al., 2002, Quantitative comparison of functional screening by measuring intracellular Ca2+ with radioligand binding at recombinant human dopamine receptors, AAPS Pharmsci 4(4)102-111.
Kolh et al., 2005, Effects of dobutamine on left ventriculoarterial coupling and mechanical efficiency in; acutely schemic pigs, J Cardiovasc Pharmacol. 45(2):144-52.
Matsui et al., 2012, Thromboxane A2 receptor signaling facilitates tumor colonization through P-selectin-mediated interaction of tumor cells with platelets and endothelial cells, Cancer Science 103(4):700-707.
Ogletree et al., 1985, Pharmacological actions of SQ 29,548, a novel selective thromboxane antagonist, J. Pharmacol Exp Ther 234:435-441.
Rolin et al, 2001, Activity of a novel dual thromboxane A2receptor antagonist and thromboxane synthase inhibitor (BM-573) on platelet function and isolated smooth muscles, Prostaglandins, Leukotrienes, and Essential Fatty Acids 65(2):67-72.
Rolin et al, 2003, BM-573, a dual 1-5, thromboxane synthase inhibitor and 10-19, thromboxane receptor antagonist, prevents 22-30 pig myocardial infarction induced by coronary thrombosis, The Journal of Phramacology and Experimental Therapeutics 306(1):59-65.
Rolin et al., 2004, Pharmacological evaluation of both enantiomers of (R,S)-BM-591 as thromboxane A2; receptor antagonists and thromboxane synthase inhibitors, Other Lipid Mediat. 74(1-4):75-86.
Ruef et al., 2006, Coronary stent thrombosis related to aspirin resistance: What are the underlying mechanisms?, J Inter. Cardiol. 19:507-509.
Turner et al., 2011, Identification of an interaction between the TPalpha and TPbeta isoforms of the human thromboxane A2 receptor with protein kinase C-related kinase (PRK) 1: implications for prostate cancer.; ; J. Biol. Chem., 29;286(17):15440-57.
International Search Report and Written Opinion mailed Aug. 31, 2016, for International Patent Application PCT/IB2016/000960 with International filing date Jun. 13, 2016 (19 pages).

THROMBOXANE RECEPTOR ANTAGONISTS

CROSS-REFERENCE TO RELATED APPLICATIONS

This application is a continuation of U.S. patent application Ser. No. 15/349,379, filed on Nov. 11, 2016, which application is a continuation of U.S. patent application Ser. No. 15/178,931, filed Jun. 10, 2016, which application is a continuation of U.S. patent application Ser. No. 14/391,856, filed Oct. 10, 2014, which application is a U.S. National Stage entry of International Patent Application No. PCT/IB2013/001258, with international filing date Apr. 17, 2013, and all of the aforementioned applications claim priority to, and the benefit of, U.S. Provisional Application Nos. 61/625,540, 61/625,537, and 61/625,516, each of which were filed Apr. 17, 2012, and the contents of all of the aforementioned applications are incorporated by reference herein in their entirety.

FIELD OF THE INVENTION

The invention generally relates to compounds that function as TP antagonists for treating thrombosis.

BACKGROUND

Blood clotting is an important mechanism in preventing blood loss in response to blood vessel injury. Sometimes, however, clotting occurs in the blood vessels of a healthy person in a process called thrombosis. The resulting blood clot, or thrombus, is largely composed of blood cell fragments known as platelets or thrombocytes. A thrombus that dislodges and circulates within the blood ("embolizes") is known as an embolus.

Thrombosis and embolism are associated with many cardiovascular diseases. When thrombosis blocks the normal flow of blood in arteries, a decreased supply of oxygen and glucose can cause tissue damage. The restricted blood flow, or ischemia, can cause injury to any organ and may even result in death. When a thrombus disturbs the supply of blood to the brain, a stroke may result. When a thrombus obstructs a coronary artery, the result can be a heart attack. Other diseases associated with thrombosis include angina pectoris, transient ischemic attack, peripheral arterial disease (PAD), peripheral vascular disease (PVD) and arterial thrombosis, to name a few. Accordingly, there is medical interest in treating thrombosis.

Thrombosis is stimulated by the arachidonic acid-derived prostanoid thromboxane (TX) $A_2$. $TXA_2$ triggers platelet activation and aggregation by agonistically binding to receptors on the surface of platelets and stimulating the expression of integrins on the platelet surface. Integrins on one platelet are then bound by fibrinogen to other platelets, thereby building up a clot. $TXA_2$ also stimulates contraction of various types of smooth muscle including vascular smooth muscle, leading to vasoconstriction, as well as of renal and pulmonary smooth muscle.

Attempts to treat thrombosis have involved targeting the synthesis of $TXA_2$. An enzyme called cyclooxygenase (COX) produces prostaglandin (PG) $H_2$ through its enzymatic conversion from the 20 carbon lipid arachidonic acid to generate a series of lipid mediators referred to as the prostanoids. In this synthetic pathway, the COX-derived $PGH_2$ endoperoxide product is converted by a host of specific PG synthases to make the prostaglandins $PGD_2$, $PGE_2$, $PGF_{2\alpha}$ and $PGI_2$ (Prostacyclin) and by TXA synthase to make $TXA_2$. The prostanoids are made in a cell- or tissue-specific manner and mediate a diverse range of physiologic roles in the body. By way of example, $TXA_2$ is predominantly made in platelets and in activated macrophages. Thus, inhibiting COX, such as within platelets or macrophage, should reduce or prevent the synthesis of $TXA_2$.

Non-steroidal anti-inflammatory drugs (NSAIDs), such as aspirin, inhibit COX, thus interfering with the synthesis of $TXA_2$. However, since COX produces the other physiologically important prostanoids, NSAIDs can cause a general imbalance in prostanoid levels. This imbalance can actually increase the risk of thrombosis, leading to stroke and other problems. Furthermore, a large part of the population exhibits aspirin resistance. Also problematic, COX inhibitors are associated with the irritation of gastric mucosa, peptic ulceration, and renal failure.

Of note was the discovery that the COX enzyme exists as two distinct types or isoenzymes referred to as COX-1 and COX-2. Since COX-1 inhibition was thought to cause gastric irritation, selective inhibitors of COX-2 (coxibs) were developed. However, the coxibs have not proven satisfactory. For instance, coxibs appear to increase the risk of atherothrombosis and myocardial infarction, even with short-term use. Notably, the coxib Vioxx was withdrawn from the market after its use was shown to be associated with adverse thromboembolic events.

Given these problems with COX inhibitors, there is clinical interest in blocking the function of $TXA_2$ by blocking the $TXA_2$ receptor (the T prostanoid receptor, or in short the TP) at the platelet surface. A compound that binds to the TP antagonistically should inhibit $TXA_2$ binding and platelet aggregation and thus thrombosis. Furthermore, as the primary COX-1/COX-2 product $PGH_2$, an endoperoxide, also binds and activates the TP, antagonists of the TP should also impair its activation by $PGH_2$. Moreover, in addition to its enzymatic conversion into the prostanoids through the COX-1/COX-2 catalyzed reactions, arachidonic acid can also be converted non-enzymatically into the isoprostanes through free-radical mechanisms. Noteworthy, the isoprostane 8-iso-$PGF_{2\alpha}$ is the most abundant isoprostane generated during oxidative injury and actually mediates its actions/signals through the TP. Hence, selective TP antagonists will have the added advantage over COX-1/COX-2 inhibitors, such as aspirin or coxibs, in that they will also inhibit the adverse actions of the isoprostane 8-iso-$PGF_{2\alpha}$ generated during oxidative injury and of the endoperoxide $PGH_2$, in addition to inhibiting the action of $TXA_2$ itself. Unfortunately, existing TP antagonists have proven problematic. For example, they lack efficacy, TP specificity and target other receptors, such as the $PGD_2$, platelet activating factor 4, or Leukotriene $D_4$ receptors.

In humans and primates, but not in other species, $TXA_2$ actually signals through two distinct TP receptor isoforms referred to as TPα and TPβ which are encoded by the same gene and differ exclusively in their distal carboxy-terminal primary amino acid sequences. Furthermore, the current TP antagonists do not discriminate between the two TPα and TPβ receptor isoforms which play similar, but not identical, roles. TPα, for example, is subject to desensitization in ways that TPβ is not and vice versa. Due to their distinct roles, in addition to developing general TP antagonists, there may also be clinical interest in compounds that can selectively interact with one or both isoforms of the TP.

SUMMARY

The invention generally provides compounds that bind to thromboxane (TX) $A_2$ receptors (TP) and inhibit thrombosis and other events within the cardiovascular, renal or pulmonary systems. Compounds of the invention prevent $TXA_2$, and other incidental ligands including the endoperoxide $PGH_2$ and the isoprostane 8-iso-$PGF_{2\alpha}$ from binding to the TP and stimulating platelet activation and aggregation, thereby decreasing the risk of a clinically significant thrombus or embolus, or binding and activating the TPα and/or TPβ isoforms expressed in cells of the cardiovascular, renal or pulmonary systems. Thus, the TP antagonists of the invention provide beneficial pharmaceutical properties for treating thrombosis and other events within the cardiovascular, renal or pulmonary systems. The invention further provides compounds that selectively bind to either the TPα and/or TPβ form of the $TXA_2$ receptor (the TP).

Compounds of the invention include any compound that prevents or attenuates thrombosis by binding antagonistically to the TP and that preferably do not specifically bind to non-thromboxane receptors or other proteins.

In certain aspects, the invention provides a TP antagonist, or a pharmaceutically acceptable salt thereof, which includes a substituted nitro-phenoxy phenyl, a sulfonylurea, and an alkyl group. In some embodiments, the alkyl group is either an isopropyl group, a pentyl group, a tert-butyl group, or a cyclohexyl group.

In certain embodiments, the TP antagonist is represented by formula (I):

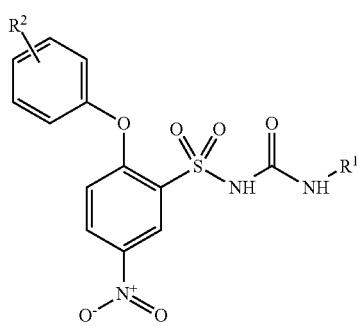

(I)

in which $R^1$ is an alkyl group and $R^2$ is either a halogen, an alkyl group, or an aryl group.

The invention further provides compounds of formula (I), in which $R^1$ is an isopropyl group, a pentyl group, a tert-butyl group, and a cyclohexyl group and $R^2$ is one of:

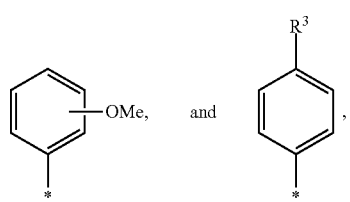

I with $R^3$ being OH, I, $CH_3$, $CO_2Me$, $CO_2H$, or

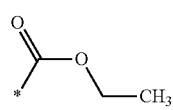 [SMILES: *C(=O)OCC]

As used herein, * represents the point of attachment.

In certain embodiments, the TP antagonist is represented by one of the formulas (II), (III), (IV), (V), (VI), (VII), (VIII), (IX), (X), and (XI):

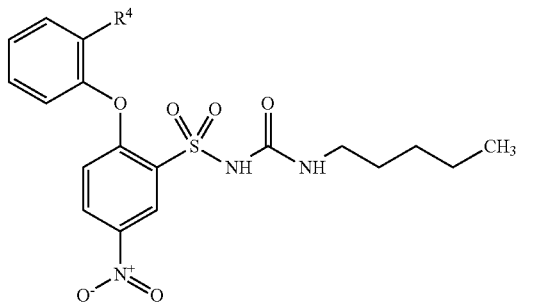

(II)

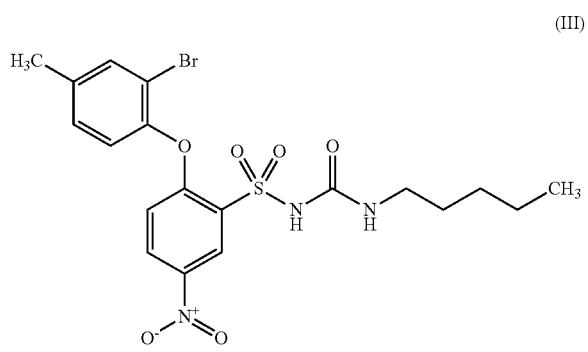

(III)

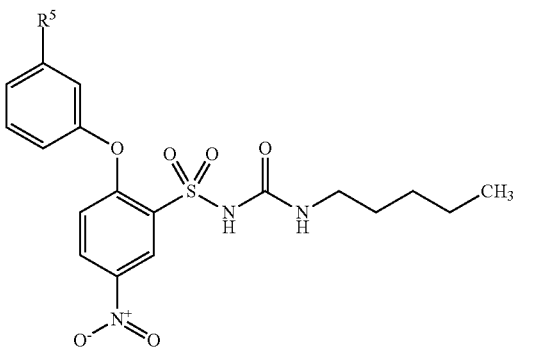

(IV)

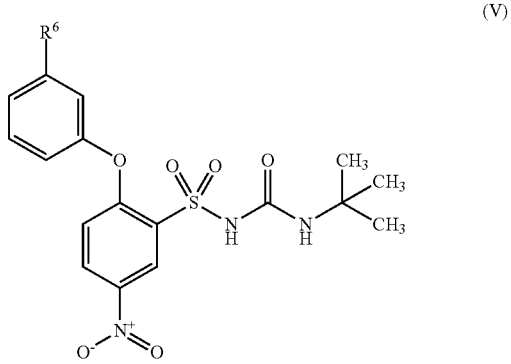

(V)

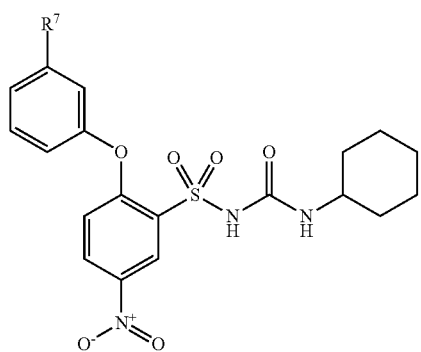
(VI)
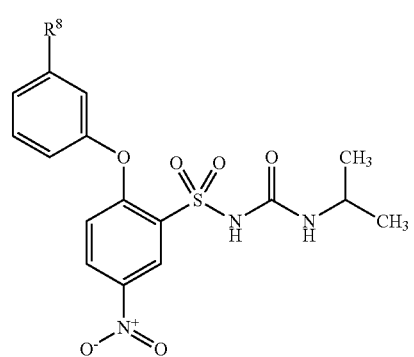
(VII)
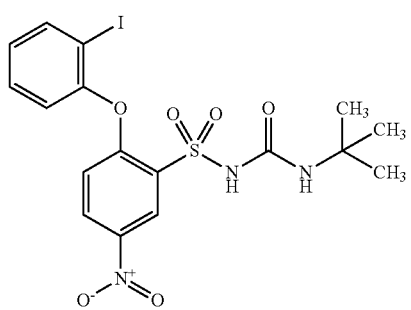
(VIII)
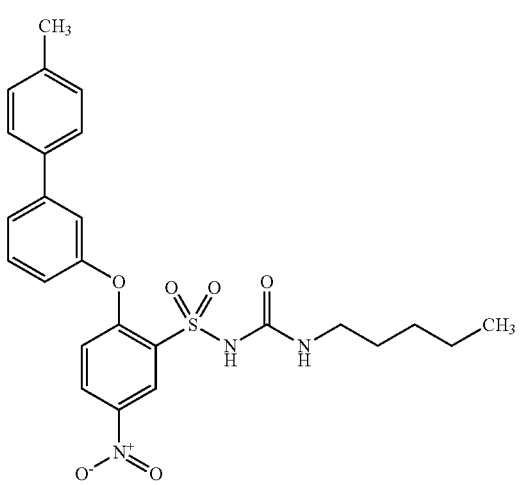
(IX)
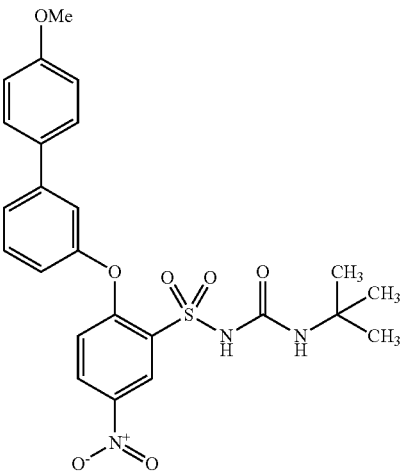
(X)
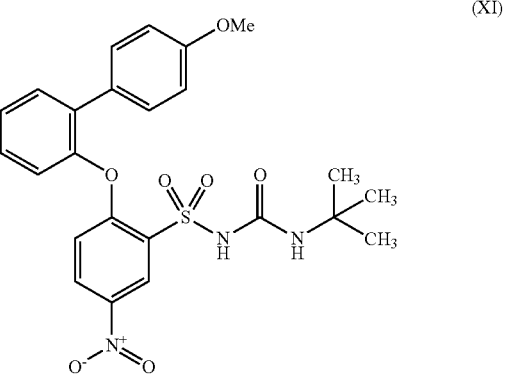
(XI)
In which R⁴ is
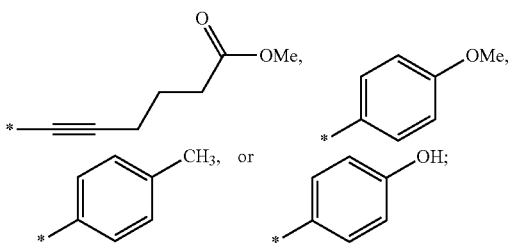
R⁵ is one of
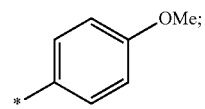
R⁶ is
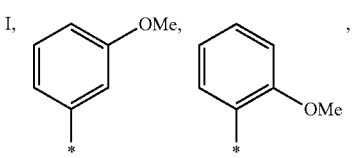

-continued
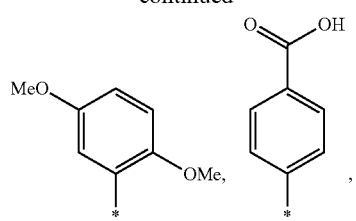
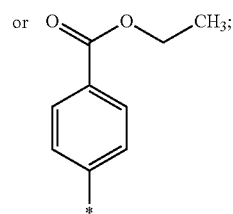 [SMILES: *c1ccc(C(=O)OCC)cc1]
$R^7$ is
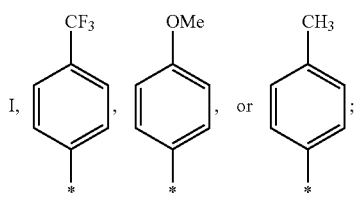
$R^8$ is
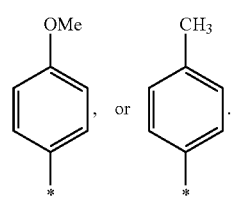
In certain embodiments the TP antagonist is represented by formula (XII):
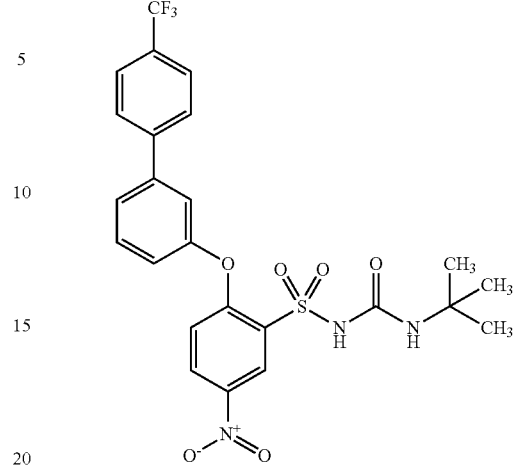
(XII)
In certain embodiments the TP antagonist is represented by formula (XIII):
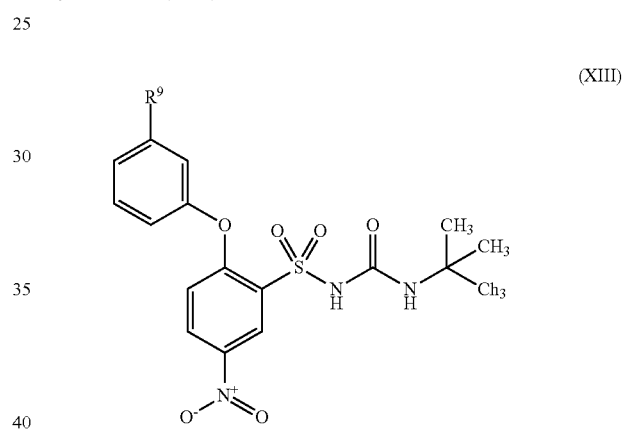
(XIII)
in which $R^9$ is
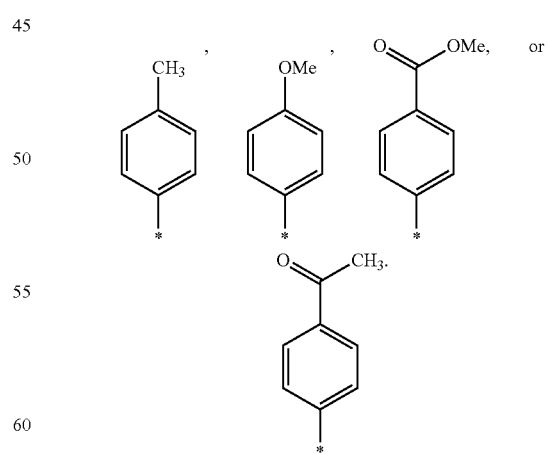
or a pharmaceutically acceptable salt thereof.
In certain embodiments, the TP antagonist is represented by one of the formulas (XIV), (XV), (XVI), (XVII), (XVIII), (XIX), (XX), and (XXI):

(XIV)
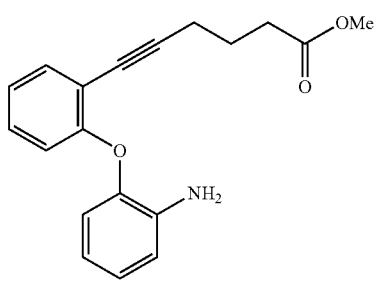
(XV)
(XVI)
(XVII)
(XVIII)
(XIX)
(XX)
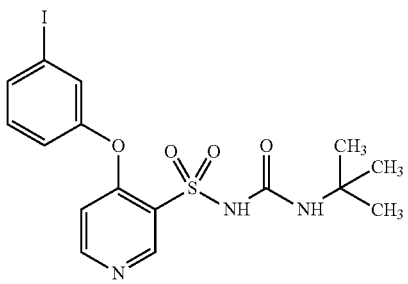
(XXI)
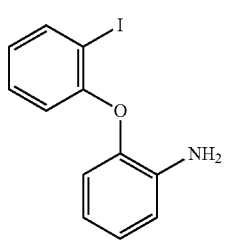
In certain embodiments, the TP antagonist is represented by formula (XXII):
(XXII)
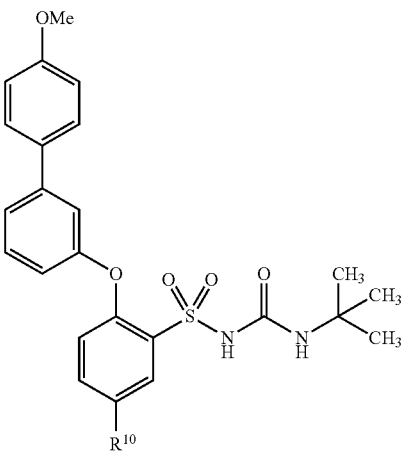
in which $R^{10}$ is
H, $NH_2$, I,
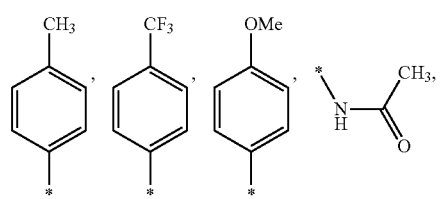
and $CO_2Me$.
In certain embodiments, the TP antagonist is represented by formula (XXII):

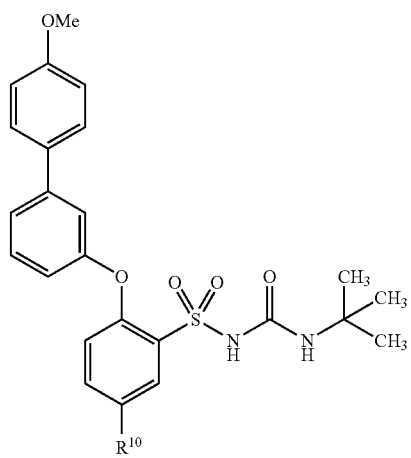
(XXII)
wherein R[10] is selected from the group consisting of
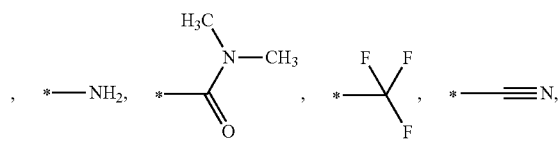
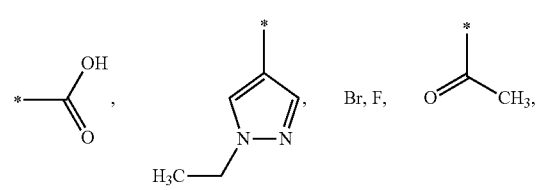
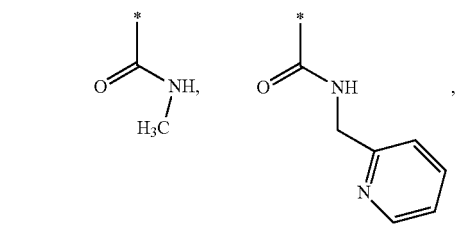
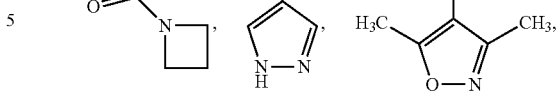
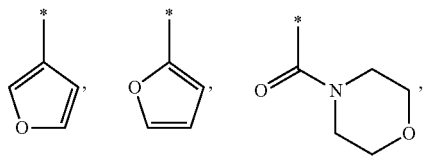
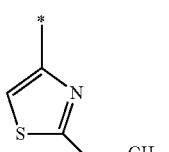 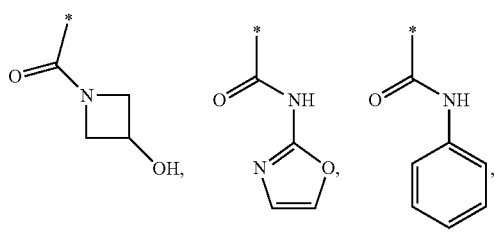
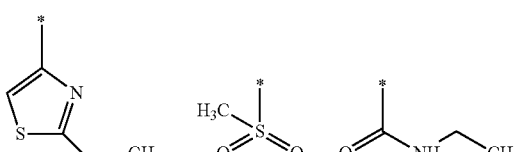
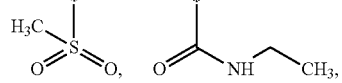
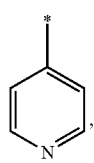
and Cl, or a pharmaceutically acceptable salt thereof.
In certain embodiments, the TP antagonist is represented by one of (LVII), (LVIII), (LIX), and (LX):
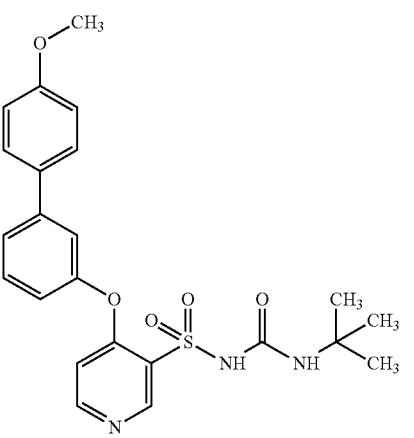
(LVII)

-continued

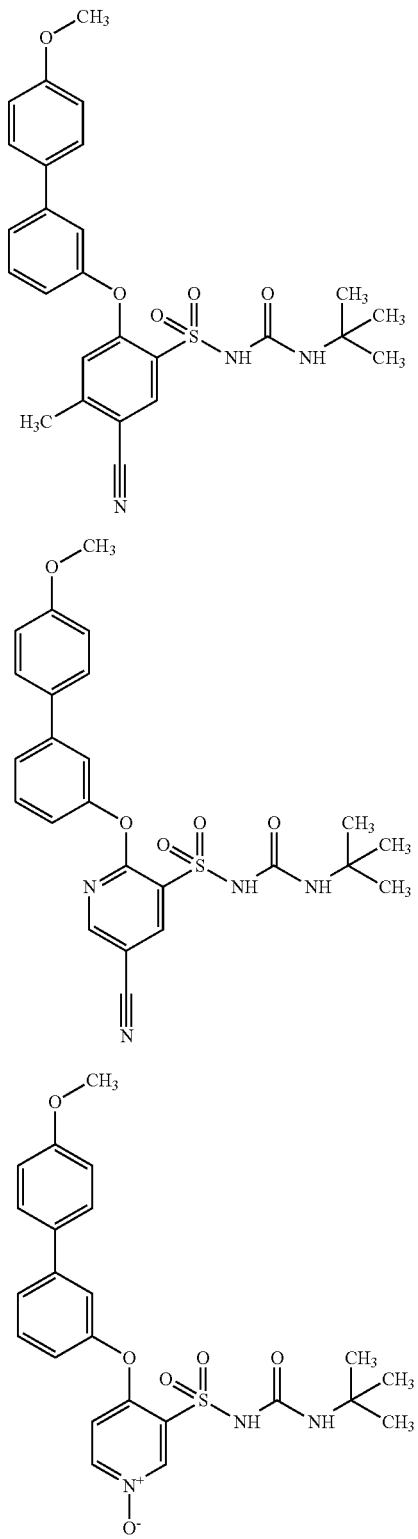

(LVIII)

(LIX)

(LX)

or a pharmaceutically acceptable salt thereof.

In certain aspects, the invention provides a method of treating a condition that involves administering an effective dose of an antithrombotic compound, or a pharmaceutically acceptable salt thereof. The antithrombotic compound or the salt thereof can be one that specifically binds to a TP and preferably does not specifically bind to non-thromboxane receptors. In some embodiments, the antithrombotic compound exhibits preferential binding for either TPα and/or TPβ receptor subtype.

Exemplary conditions treatable by methods of the invention include atherothrombosis, stroke, myocardial infarction, atherosclerosis, arteriosclerotic vascular disease, thromboembolism, deep vein thrombosis, arterial thrombosis, ischemia, peripheral vascular disease, peripheral artery occlusive disease, coronary artery disease, angina pectoris, and transient ischemic attack, various renal (e.g. glomerulonephritis, proteinuria including that associated with types I or II diabetes mellitus etc.) and pulmonary diseases (e.g., asthma. Pulmonary arterial hypertension etc.). Compounds of the invention may be used to treat cardio-vascular diseases (CVDs), atherothrombotic events associated with acute coronary syndrome (ACS), or other conditions. In some embodiments, the invention provides compounds for reducing cerebro- and cardio-vascular episodes in patients with a history of ischemic stroke or transient ischemic attack or for the acute post-operative management of at-risk patients following certain surgical or intervention procedures.

In certain aspects, the invention provides an implantable medical device comprising a compound of the invention and methods of delivering a compound of the invention via a temporary or permanent or retrievable or bioabsorbable or bio-erodable device or implant. Devices and methods of the invention can provide an antithrombotic compound in a stent (e.g., a drug eluting stent (DES)) or a balloon (e.g., a drug eluting balloon). In a preferred embodiment, the compound has formula (X).

The TP antagonist molecules of the invention such as the compound having formula (X) provide ideal drugs as a coating agent on DES, as well as on bifurcation stents, by-pass graft vessel stent and medical devices used to treat stroke or other cardiovascular episodes or diseases. Compounds of the invention and implantable devices comprising the compounds may exhibit any of a number of salutary effects, including: prevention of platelet aggregation and secretion at sites of local vessel damage; reduction of the inflammatory effects of elevated levels of $TXA_2$ at sites of local vessel damage; prevention of $TXA_2$-induced smooth muscle cell proliferation, neo-intima thickening, and restenosis (which is primarily driven by elevated levels of $TXA_2$ and/or $PGH_2$ at the damaged blood vessel wall); and inhibition of the undesirable actions of 8-iso-$PGF_{2\alpha}$ within a damaged blood vessel. Compounds and devices of the invention in combination with very low levels of sirolimus and/or paclitaxel will be synergistic in further preventing restenosis while at the same time in eliminating and/or reducing the adverse effects associated with local, high levels of sirolimus or paxlitaxol. By antagonizing the TP receptor on endothelial cells compounds of the invention may prevent both $TXA_2$- and isoprostane (8-iso-$PGF_{2\alpha}$)-induced suppression of VEGF signaling, which in turn will enable VEGF induced re-endothelialization and/or vascular repair, further preventing restenosis in response to $TXA_2$ or isoprostanes or other growth factor(s) released from activated platelets or macrophages.

In certain aspects, the invention provides an implantable medical device coated with a compound of the invention along with clot-dissolving agents such as tissue plasminogen activator (tPA) or urokinase, their derivatives or other such agents which will act synergistically to both lyse and dissolve clots in the vicinity of the stent or balloon as well as preventing future clot formation, such as in the treatment of ischemic or cerebral stroke. Such dual coatings can also be incorporated into clot retriever systems.

A stent according to the invention comprises a compound of the invention and may have an expandable structure. A stent may be formed at least in part from an open lattice. In some embodiments, the invention provides an implantable medical device coated with a compound of the invention, preferably having formula (X).

DETAILED DESCRIPTION

Figure 1A:
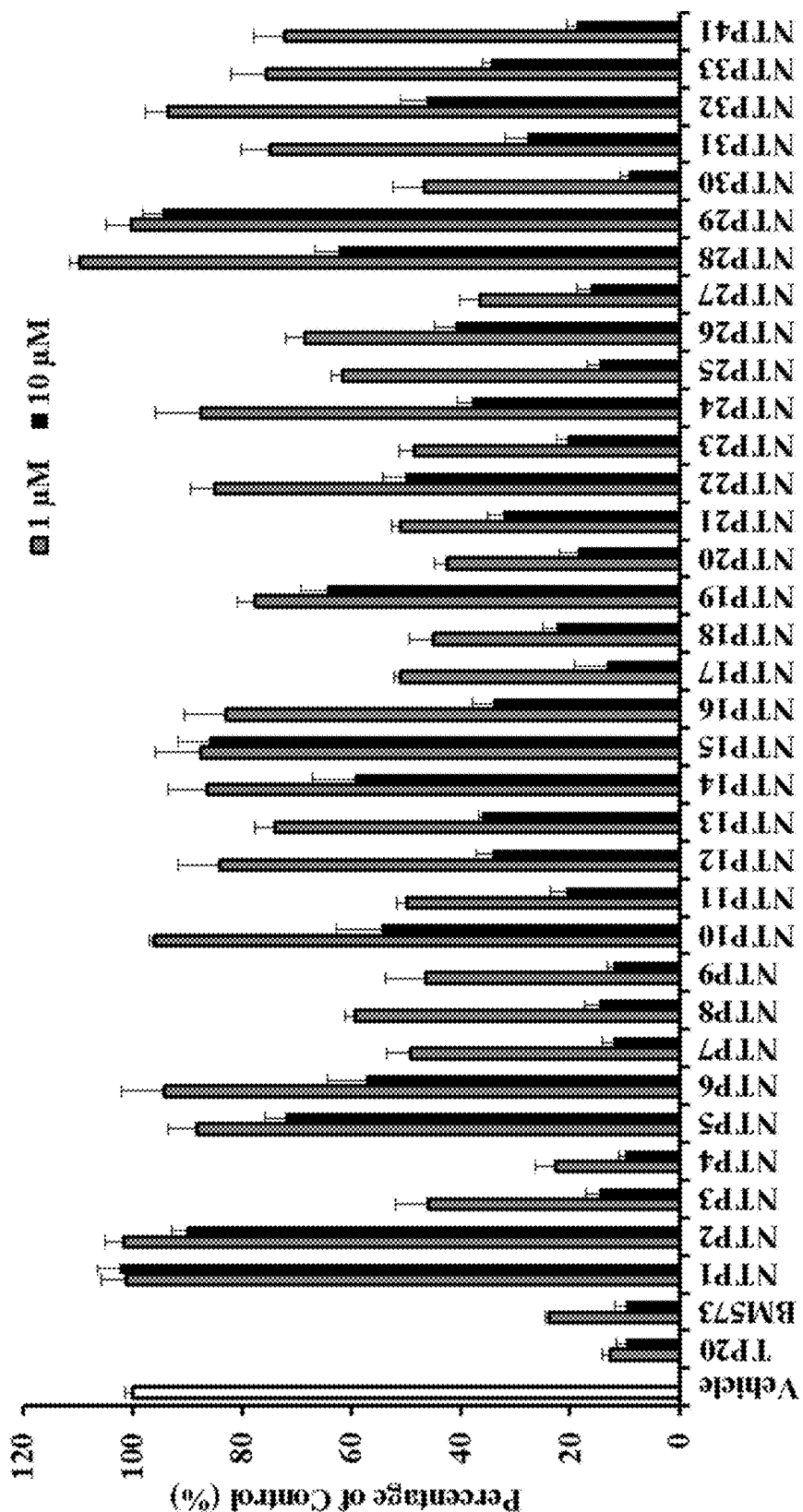
FIGS. 1A and 1B show the effect of the TP antagonist compounds of the invention on U46619-mediated calcium mobilization in HEK.TPα and HEK.Tβ cells

The invention generally relates to compounds that prevent or attenuate thrombosis by binding antagonistically with TP to prevent the binding of $TXA_2$, $PGH_2$ and/or isoprostanes including 8-iso-$PGF_{2\alpha}$. Compounds of the invention include those that exhibit preferential binding for either TPα and/or TPβ receptor subtype. As discussed herein, the invention provides small molecule antithrombotic compounds, which inhibit platelet aggregation and exhibit attractive ADME (absorption, distribution, metabolism, and excretion) properties. The invention further provides exemplary synthetic routes for antithrombotic compounds by way of example but not exhaustive of all routes of synthesis. Exemplary compounds of the invention are disclosed.

In some embodiments, compounds of the invention display significant TP selectivity and antagonistic activity ex vivo in human platelets and are effective in preventing in vivo thrombosis in rodents using the ferric chloride model, as discussed, for example, in U.S. Pub. 2005/0025705, herein incorporated by reference in its entirety.

Compounds of the invention preferably inhibit $TXA_2$-induced platelet aggregation at a half-maximal inhibitory concentration ($IC_{50}$) below 100 nM. Compounds of the invention preferably inhibit $TXA_2$-induced platelet aggregation at a half-maximal inhibitory concentration ($IC_{50}$) below 50 nM. Compounds of the invention preferably inhibit $TXA_2$-induced platelet aggregation at a half-maximal inhibitory concentration ($IC_{50}$) below 20 nM. Compounds of the invention preferably inhibit $TXA_2$-induced platelet aggregation at a half-maximal inhibitory concentration ($IC_{50}$) below 5 nM. In certain embodiments, compounds of the invention further inhibit $TXA_2$-induced platelet aggregation but not aggregation induced by other platelet agonists such as, for example, thrombin or adenosine diphosphate (ADP). Further, compounds of the invention preferably do not agonize or antagonize signaling by several other G-protein coupled receptors, kinases, phosphatases, or ion channels including human Ether-á-go-go related gene (hERG).

Compounds of the invention exhibit attractive ADME properties. In some embodiments, compounds have a half-life of 20 minutes and more than 200 minutes in rat hepatic microsomes and plasma, respectively. Inventive compounds have greater than 50% oral bioavailability and a 4.5 hour elimination half-life for oral delivery. In some embodiments, inventive compounds exhibit 1.4 ml/min/kg clearance rates following I.V. delivery and are neither cytotyoxic or genotoxic. TP antagonists of the invention exhibit the ability to inhibit agonist-induced intracellular calcium mobilization and inhibit platelet aggregation in ex vivo assays. In some embodiments, compounds of the invention show no effect on signaling through other prostanoid (prostaglandin (PG) $I_2$ receptor, IP; $PGE_2$ receptors $EP_3$ and $EP_1$; $PGF_{2\alpha}$ receptor, FP) and non-prostanoid receptors including the purinergic (ADP) and thrombin (PAR1) receptors, also involved in platelet activation similar to the TP isoforms. Further, compounds exhibit minimal toxicity and favorable cell permeability.

Shown below are exemplary methods of synthesis of compounds of the invention.

First, 2-Chloro-5-nitrobenzenesulfonamide is synthesized according to Pathway A.

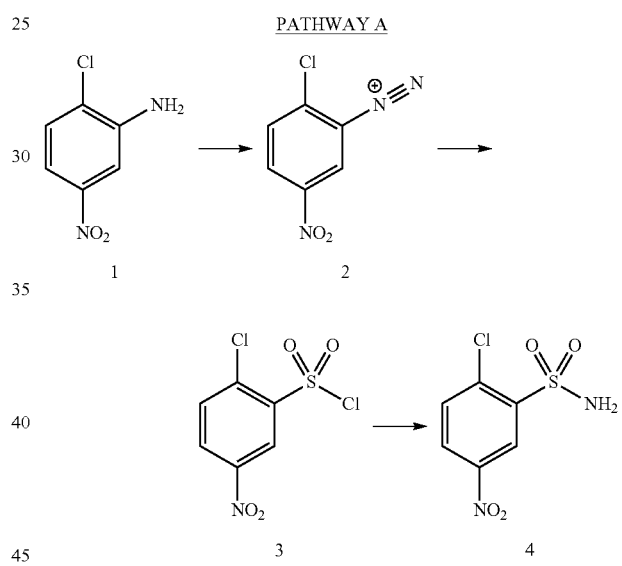

PATHWAY A

Sodium nitrite (4.96 g; 72 mmol) dissolved in water (11 mL) was added drop wise over 30 minutes to a cooled solution (−5° C.) of 2-chloro-5-nitroaniline (1; 10.00 g; 58 mmol) in 12M HCl (104 mL). While stirring at −5° C. for a further 30 minutes, a solution of copper(II) chloride dissolved in water (4 mL) was poured into acetic acid (110 mL) previously saturated with sulphur dioxide (gas). This was then added to the diazonium salt 2 solution and stirred until nitrogen gas ceased to evolve. The reaction mixture was quenched with ice-water and the subsequent precipitate formed was collected by filtration and washed with cold water. Aqueous ammonium hydroxide (35%) (120 mL) was added to the resulting sulfonyl chloride 3 and stirred for 18 hours. The solution was then filtered and the resulting filtrate was acidified using 12M HCl to precipitate the title compound 4 (7.55 g; 55% over 3 steps). M.p 186-187° C. (lit. 177-179° C.)

From this point, Pathway B was used for the synthesis of 2-(3-Iodophenoxy)-5-nitrobenzenesulfonamide 6.

PATHWAY B

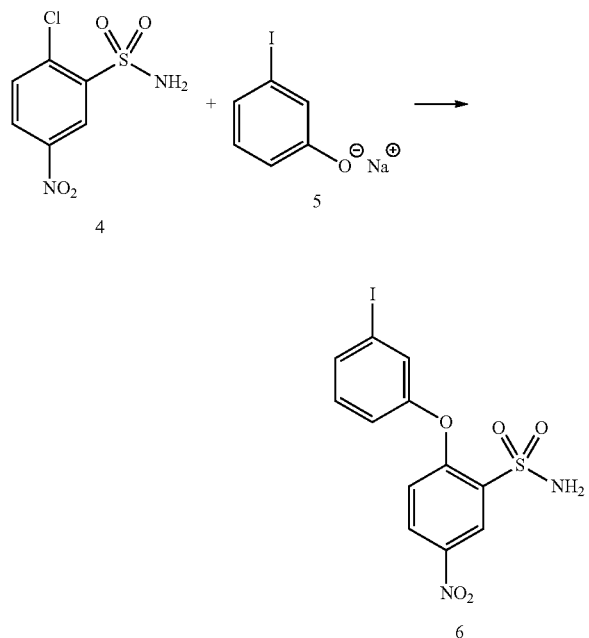

An aqueous solution of NaOH (3.66 g; 92 mmol; 10% w/v) was added to a solution of 3-iodophenol (18.30 g; 83 mmol) in acetone (130 mL). Evaporation under reduced pressure afforded the crystals of the sodium salt 5, which were added to a solution of sulfonamide 4 (3.94 g; 17 mmol) in acetonitrile (24 mL). The mixture was refluxed and potassium carbonate (1.62 g; 12 mmol) was added. After completion of the reaction (48 h, monitored by TLC), the solution was acidified using 12M HCl, diluted with water and extracted with ethyl acetate (×3). The combined organics were dried (MgSO$_4$), and concentrated in vacuo. The crude product was purified using column chromatography (SiO$_2$; pentane/ethyl acetate, 3:1), yielding the title compound 6 as a colorless solid (5.84 g; 84%). M.p. 153-155° C. (lit. 153-154° C.).

From this point, 2-(3-Iodophenoxy)-5-nitrobenzene(t-butyl)sulfonyl urea (Formula XXXVIII) was prepared according to Pathway C.

PATHWAY C

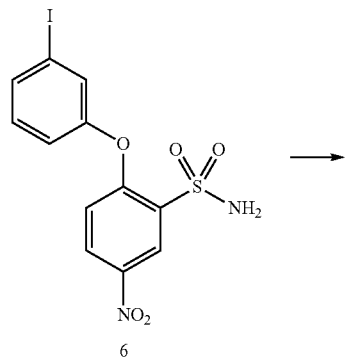

NaOH (122 mg; 3.04 mmol) dissolved in water (10% w/v) was added to a solution of sulfonamide 6 (1279 mg; 3.04 mmol) in acetone (10 mL). The mixture was stirred for 10 minutes, then the solvent was evaporated in vacuo. The resulting sodium salt was resuspended in acetone (10 mL) and gently put under reflux, then t-butyl isocyante was added to the mixture (603 mg; 700 µL; 6.08 mmol). After 40 minutes the reaction mixture was concentrated under reduced pressure and the resulting solid was washed with ethyl acetate, isolated by filtration and dissolved in an aqueous solution of 0.5M NaOH. The subsequent solution that formed was acidified to pH 1 with 12 M HCl, and the precipitate that formed was collected by filtration. This delivered the title compound 7 (Formula XXXVIII) with no further purification necessary (1484 mg; 94%). M.p. 233-236° C. (lit. 154-157° C.).

Compound 8 (Formula XLI) and/or compound 9 (Formula X) are obtained via pathway D.

PATHWAY D

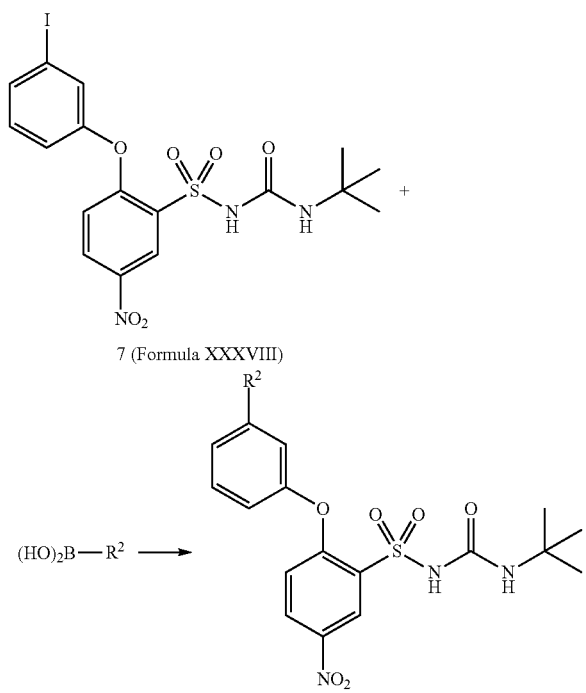

An aqueous degassed solution of potassium carbonate (4 mmol in 3.1 mL H$_2$O) was added to a schlenk tube containing aryl iodide 7 (1 mmol; Formula XXXVIII), the appropriate boronic acid (1.1 mmol), palladium(II) acetate (0.08 mmol) in DMF (3.1 mL) under nitrogen. The reaction mixture was degassed and refilled with nitrogen 3 times, and then stirred at room temperature for 24 hours. Upon completion of the reaction, the mixture was diluted with water and extracted with ethyl acetate (×3), dried over MgSO$_4$ and concentrated in vacuo. The crude product was purified using flash chromatography (8; SiO$_2$; pentane/diethyl ether, 1:1) (9; SiO$_2$; pentane/diethyl ether, 1:2), isolating the title compounds (8; 63% (Formula XLI); 9; 58% (Formula X)). M.p. (8 210-212° C.; 9 194-197° C.).

Further description of preparation of sulfonylurea derivatives is given in U.S. Pat. No. 5,434,124, incorporated by reference in its entirety. The preparation of p-nitrobenzenesulfonylurea from p-nitrobenzenesulfonamide, through a p-nitrobenzenesulfonylisourea intermediate, is described in U.S. Pat. Nos. 3,556,764 and 3,714,209, incorporated by reference herein in their entirety.

Through suitable variations of the pathways discussed herein, a variety of substituted nitrobenzenesulfonylureas of formula (I) can be prepared:

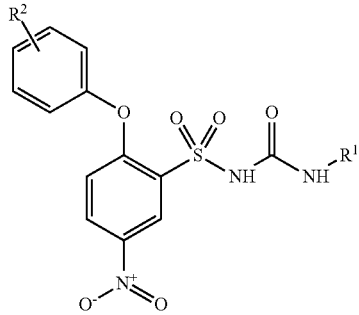

(I)

In certain embodiments, N-(tert-butylcarbamoyl)-2-(3-methoxyphenoxy)-5-nitrobenzenesulfonamide (also known as CAY10535) is obtained. CAY10535 has formula (XXIII):

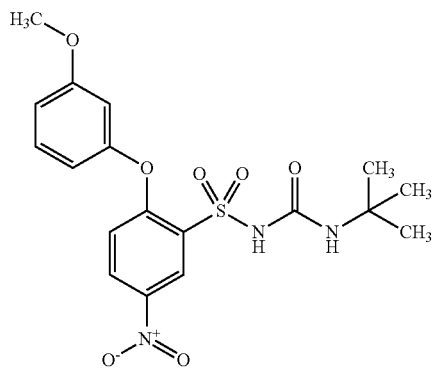

(XXIII)

CAY10535 is available from Cayman Chemical (Ann Arbor, Mich.), and has a molecular formula of C$_{18}$H$_{21}$N$_3$O$_7$S and formula weight 423.4. CAY10535 can be obtained as a crystalline solid. A stock solution is made by dissolving the compound in DMSO or ethanol with an inert gas. For solution in a aqueous buffer, CAY10535 is first dissolved in DMF and then diluted in a desired aqueous buffer.

In certain embodiments, the palladium-catalyzed Suzuki reaction is further used to add one or more aryl groups, optionally containing one or more substituents, to the above-described compounds. For example, where R$^2$ represents a para methyl group of a 4-methylphenol substituent on the oxygen bridge, that R$^2$ group can be replaced with an aryl group, including, for example, 4-methylphenyl or any other. Use of the palladium-catalyzed Suzuki reaction is described in U.S. Pat. No. 6,583,307 and U.S. Pat. No. 6,136,157, both of which are herein incorporated by reference in their entirety.

In certain embodiments, compounds of the invention, for example as synthesized according to combinations of the above-described pathways, are described by formulas (XXIV), (XXV), (XXVI), (XXVII), (III), (XXVIII), (VIII), (XXIX), (XXX), (XXXI), (XXXII), (XXXIII), (XXXIV), (XXXV), (XXXVI), (XXXVII), (XXXVIII), (XXXIX), (IX), (XL), (XLI), (XLII), (XLIII), (XLIV), (X), (XLV), (XLVI), (XII), (XLVII), and (XI).

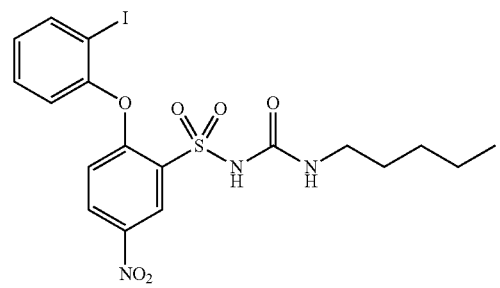

(XXIV)

Mw - 533.34

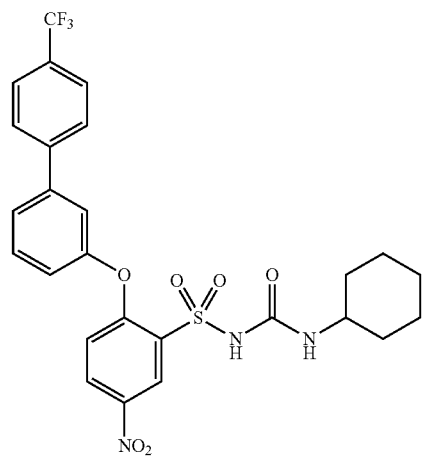

(XXV)

Mw - 563.55

(XXVI)
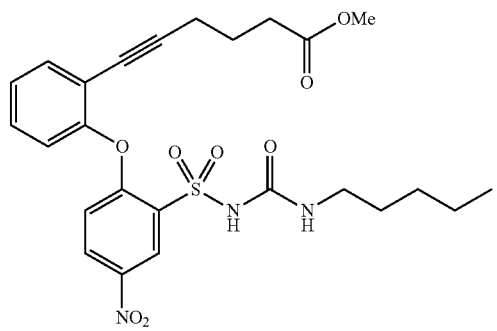
Mw - 531.17
(XXVII)
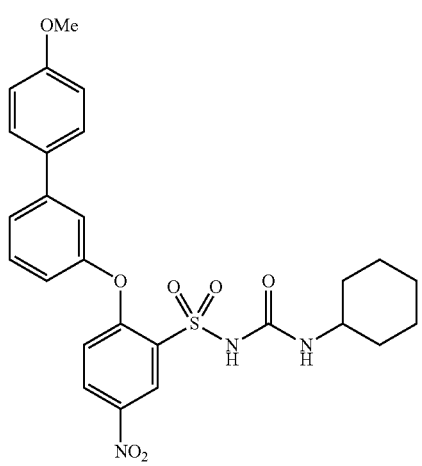
Mw - 525.57
(III)
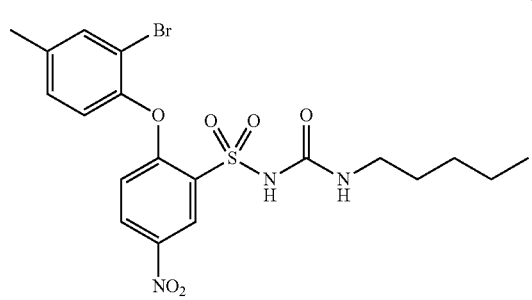
Mw - 500.36
(XXVIII)
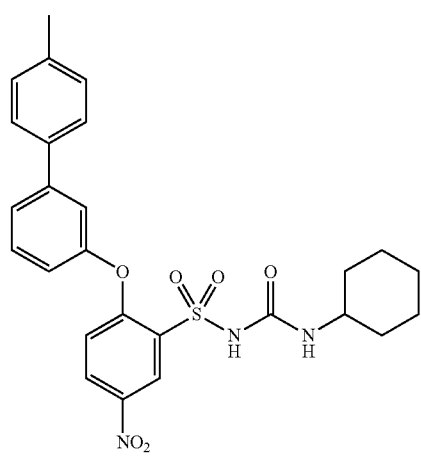
Mw - 509.57
(VIII)
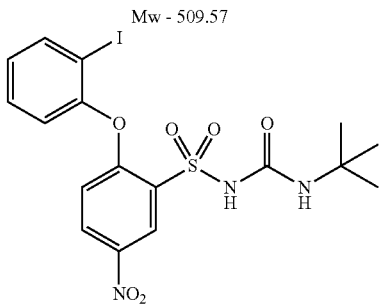
Mw - 519.31
(XXIX)
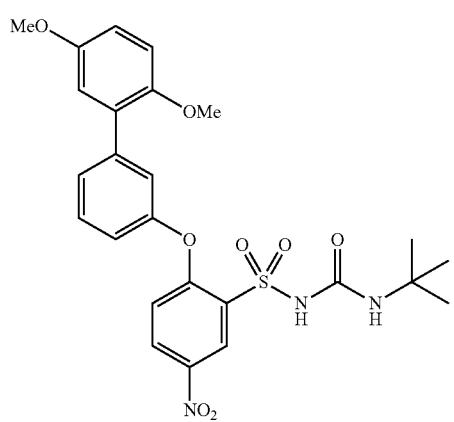
Mw - 529.56
(XXX)
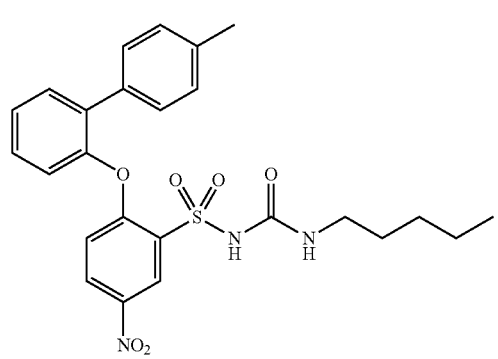
Mw - 497.56

(XXXI)
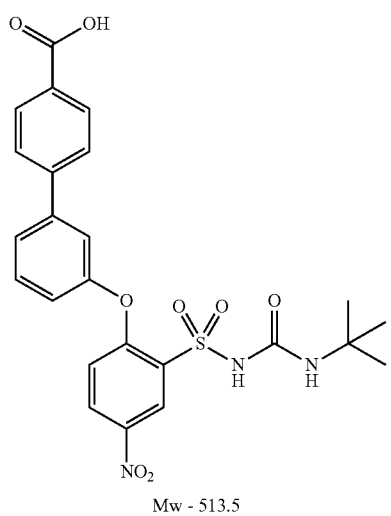
Mw - 513.5
(XXXII)
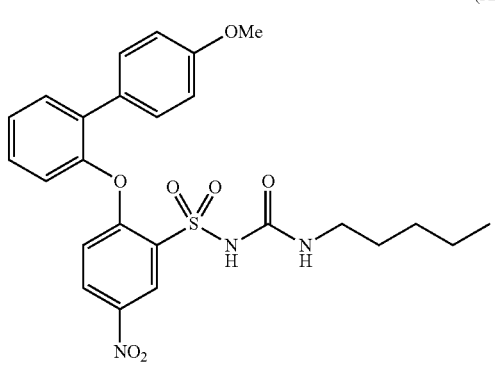
Mw - 513.56
(XXXIII)
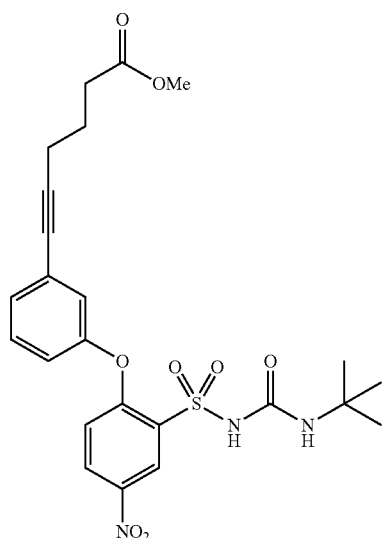
Mw - 517.55
(XXXIV)
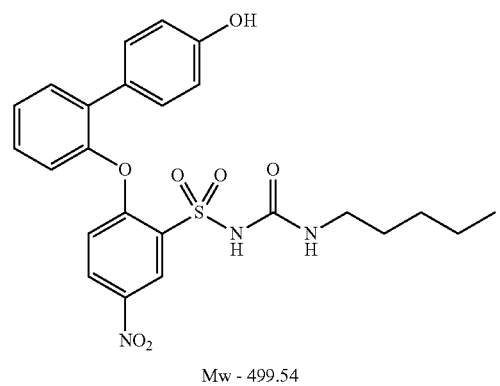
Mw - 499.54
(XXXV)
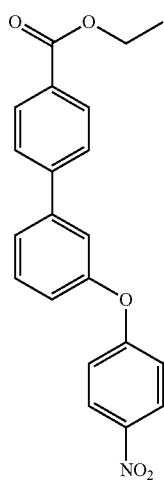
Mw - 541.57
(XXXVI)
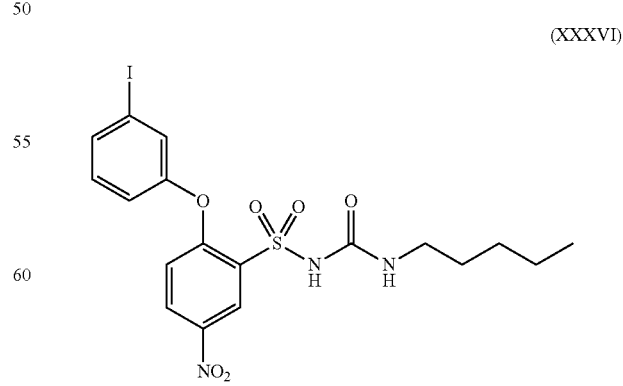
Mw - 533.34

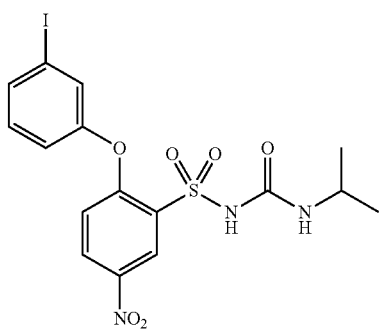
(XXXVII)
Mw - 505.28
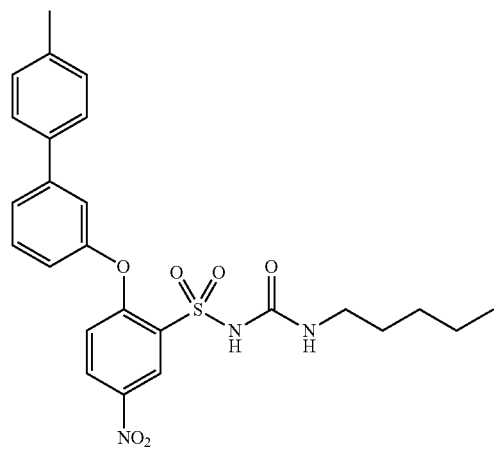
(IX)
Mw - 497.56
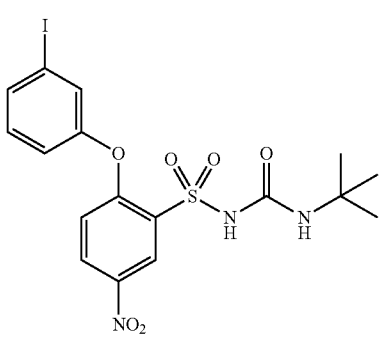
(XXXVIII)
Mw - 519.31
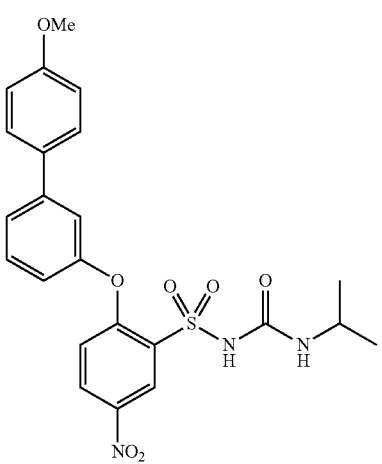
(XL)
Mw - 485.51
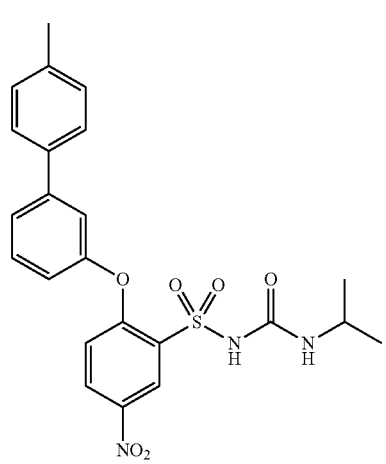
(XXXIX)
Mw - 469.51
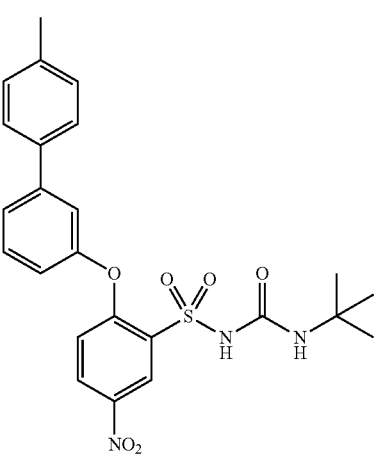
(XLI)
Mw - 483.54

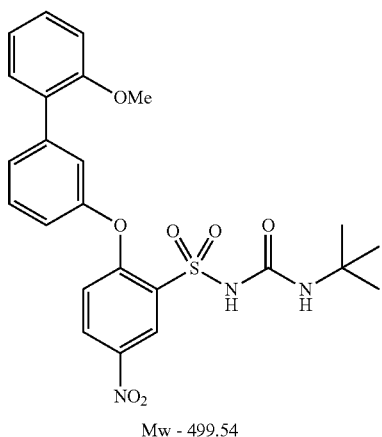
(XLII)
Mw - 499.54
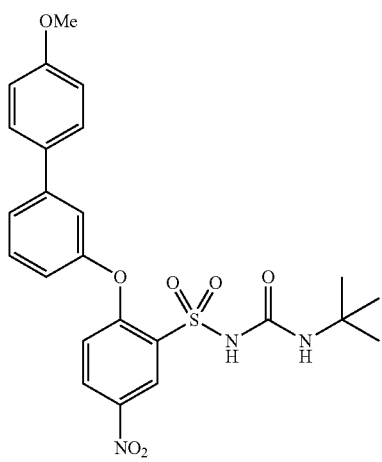
(X)
Mw - 499.54
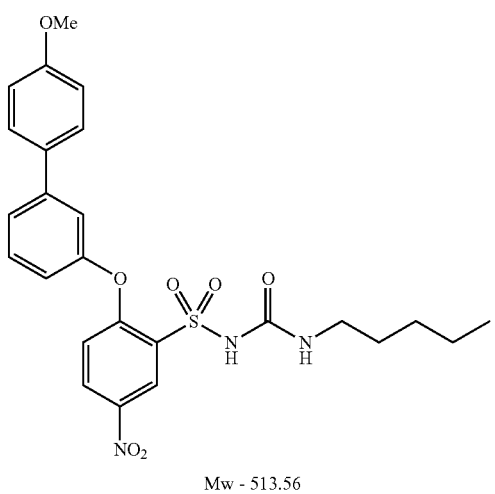
(XLIII)
Mw - 513.56
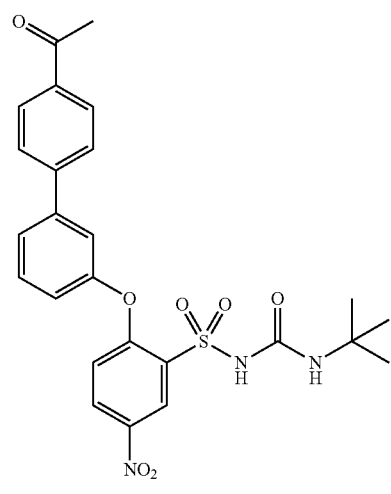
(XLV)
Mw - 511.55
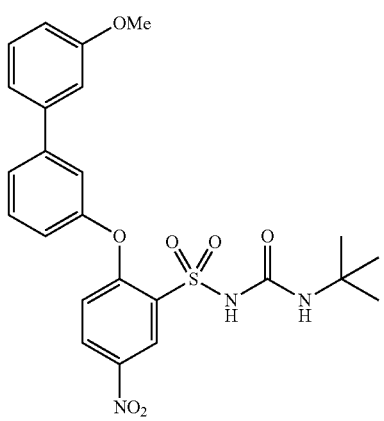
(XLIV)
Mw - 499.54
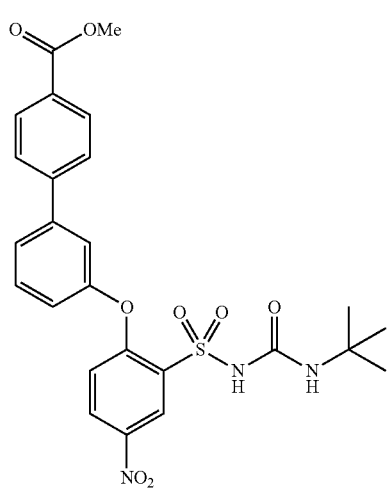
(XLVI)
Mw - 527.55

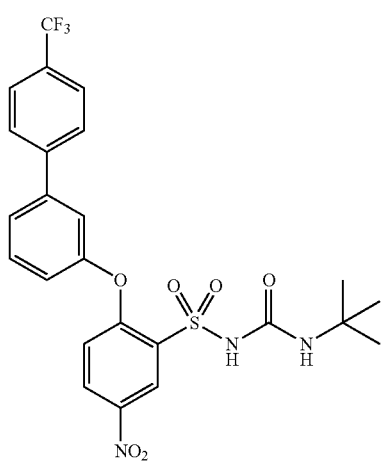

(XII)

Mw - 537.51

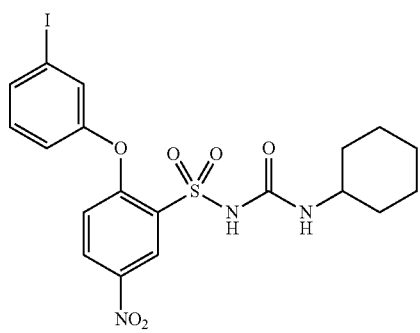

(XLVII)

Mw - 545.35

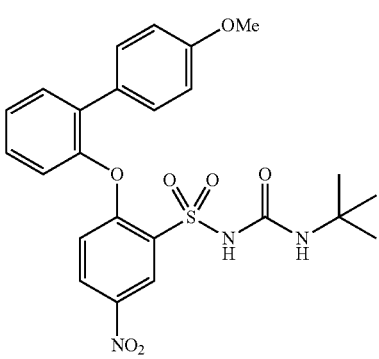

(XI)

Mw - 499.54

Further compounds of the invention are synthesized according to Pathway E. Synthesis according to Pathway E begins with a compound of formula (LII). Compounds synthesized according to Pathway E can include any moiety known in the art at $R^{13}$. Exemplary moieties for $R^{13}$ include: I, $CF_3$, H, various organic groups, methoxy phenyl, methyl phenyl, trifluoromethyl phenyl, methyl ester, and H.

PATHWAY E

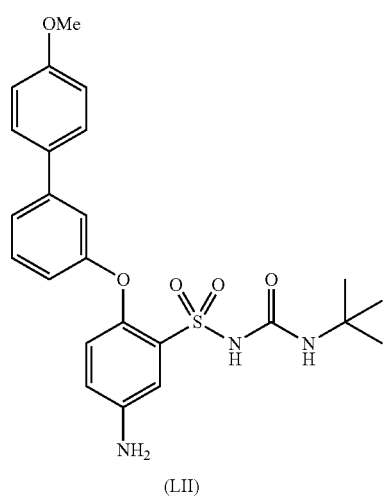

(LII)

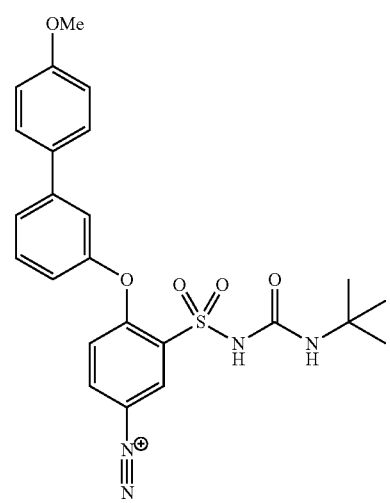

17

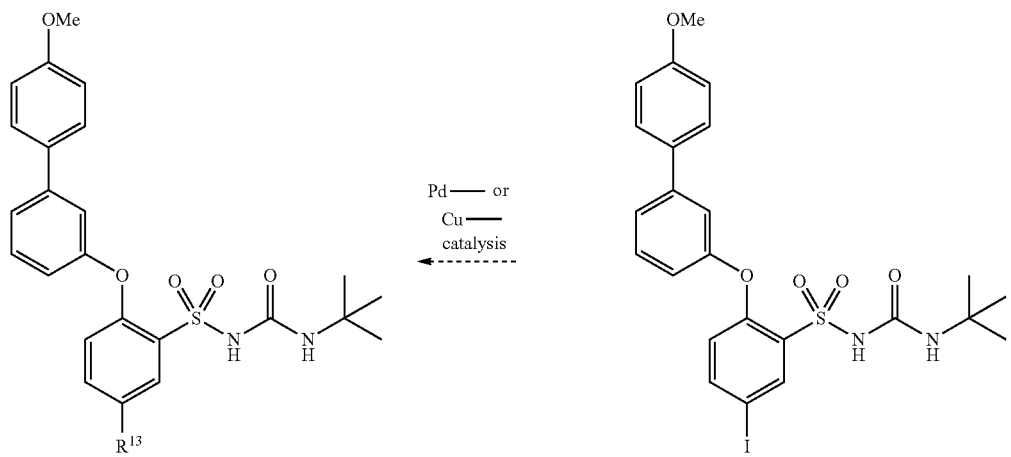
Compounds of the invention, for example, synthesized in-part according to Pathway E include compounds described by formulas (XVI), (XLVIII), (XVIII), (XLIX), (L), (LI), (LII), (LIII), (LIV), (LV), and (LVI):
(XVI)
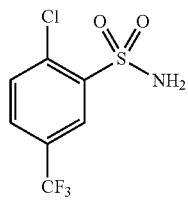
Mw - 259.63
(XVIII)
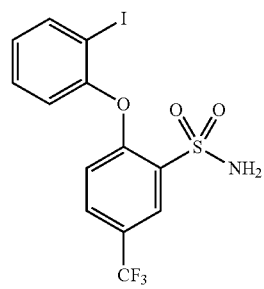
Mw - 443.18
(XLVIII)
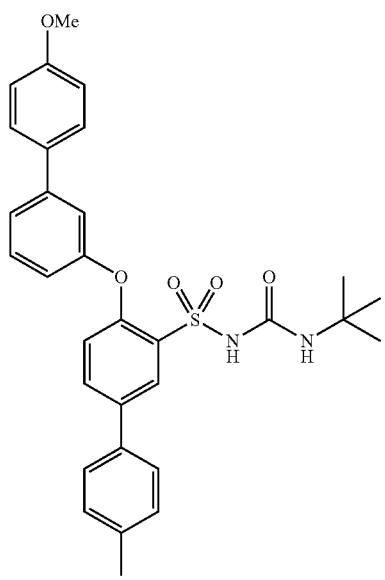
Mw - 544.66
(XLIX)
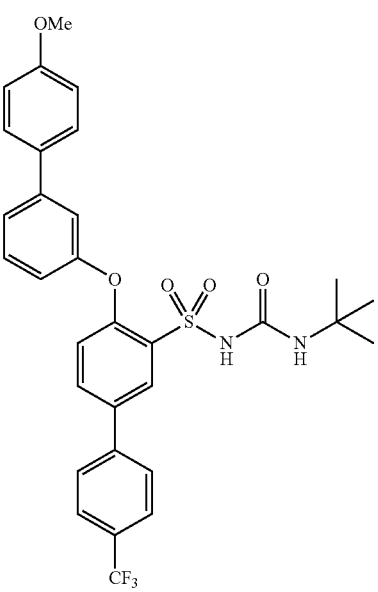
Mw - 598.63

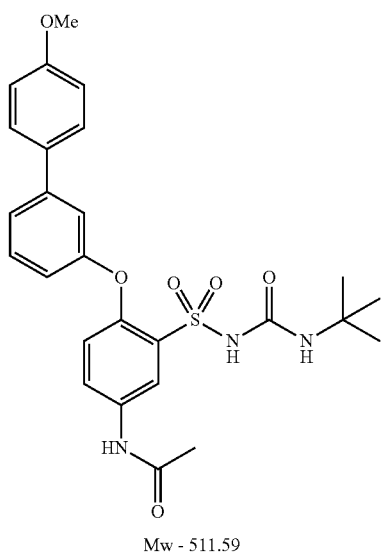
(L)
Mw - 511.59
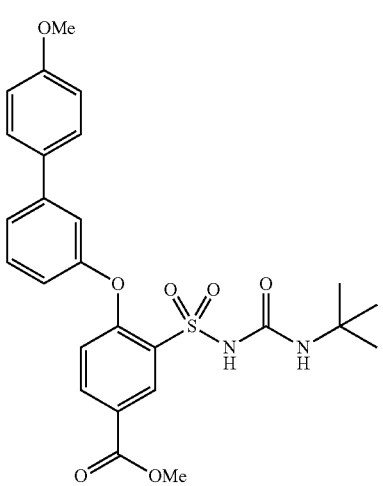
(LI)
Mw - 512.57
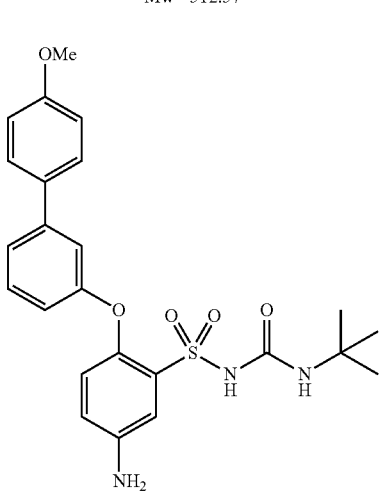
(LII)
Mw - 469.55
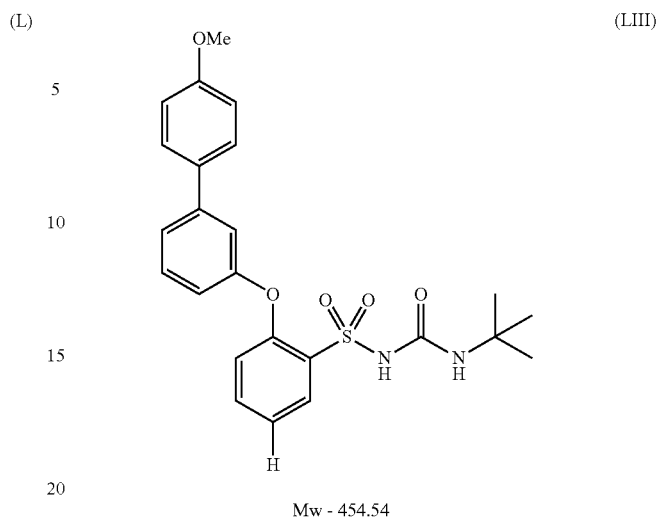
(LIII)
Mw - 454.54
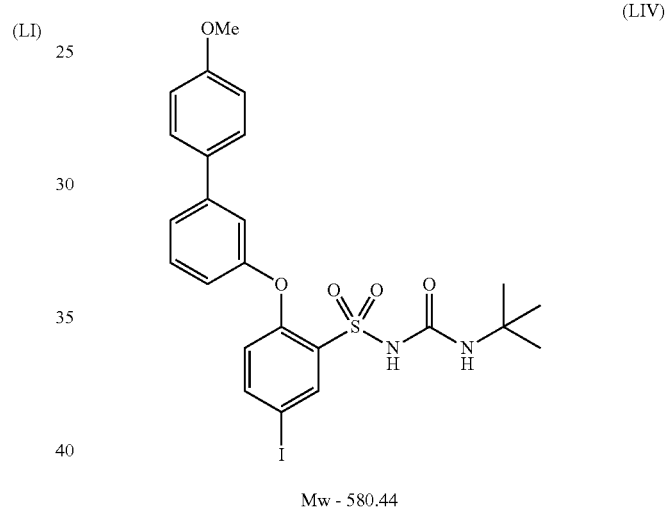
(LIV)
Mw - 580.44
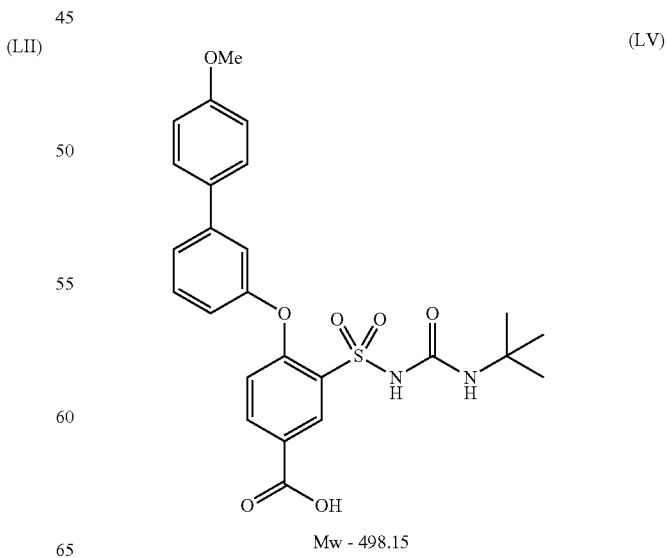
(LV)
Mw - 498.15

(LVI)

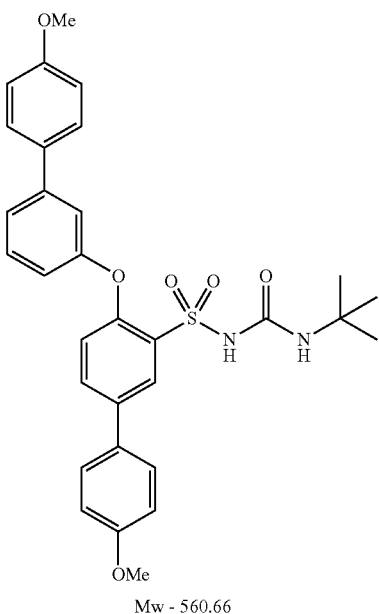

Mw - 560.66

Further compounds of the invention synthesized according to methods known in the art include compounds described by formulas (XXI), (XVII), (XIV), (XIX), (XV), and (XX):

(XXI)

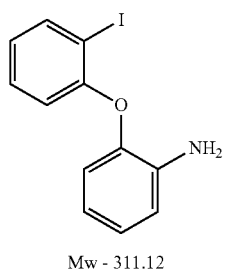

Mw - 311.12

(XVII)

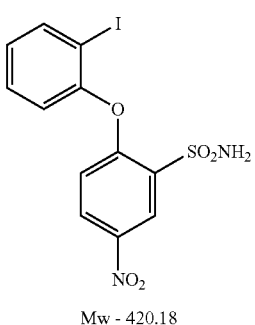

Mw - 420.18

(XIV)

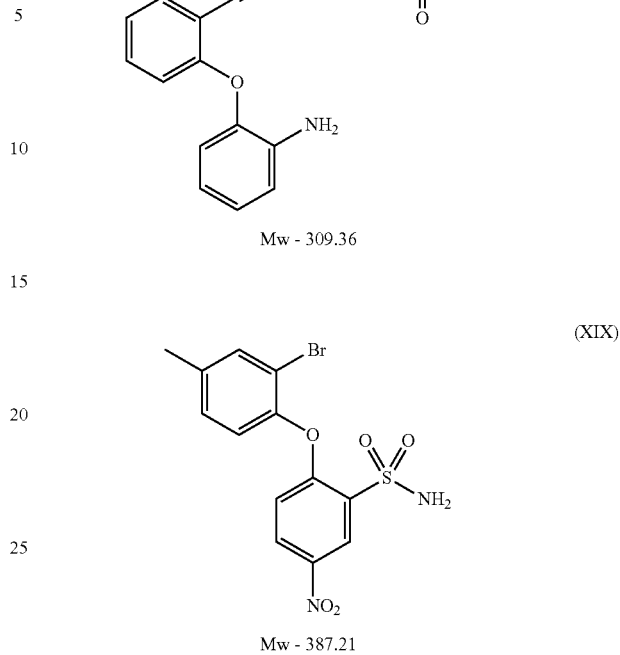

Mw - 309.36

Mw - 387.21

Mw - 236.63

(XX)

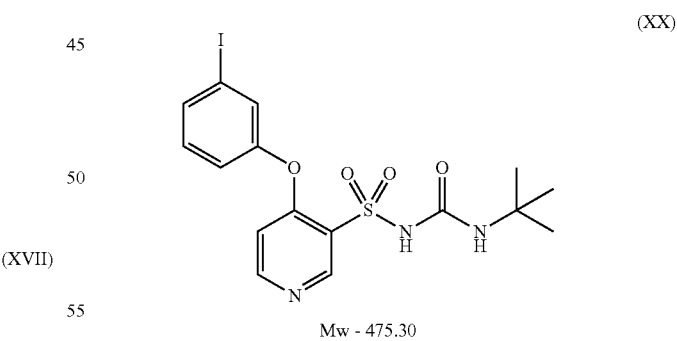

Mw - 475.30

In certain embodiments, the invention provides TP antagonist compounds, which include a substituted nitrophenoxy phenyl, a sulfonylurea, and an alkyl group. In some embodiments, the alkyl group is either an isopropyl group, a pentyl group, a tert-butyl group, or a cyclohexyl group. In some exemplary embodiments according to combinations of or modifications to the above-described synthetic pathways, the invention provides a TP antagonist including a compound represented by formula (I):

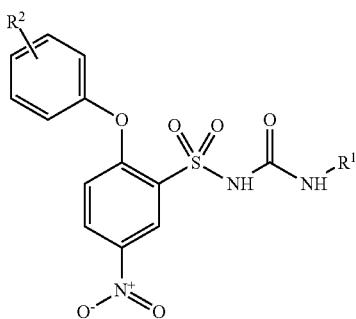

in which $R^1$ is a tert-butyl group or a pentyl group and $R^2$ is I,

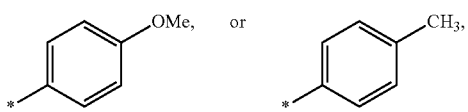 [SMILES: *c1ccc(OC)cc1 ; *c1ccc(C)cc1]

optionally in the para position.

In certain embodiments the TP antagonist is represented by formula (XIII):

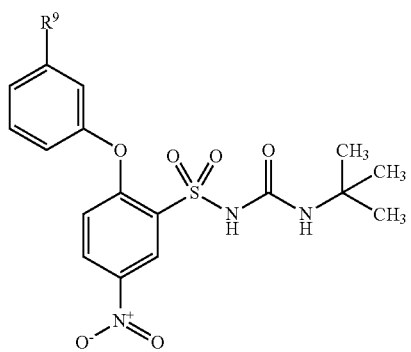

in which $R^9$ is

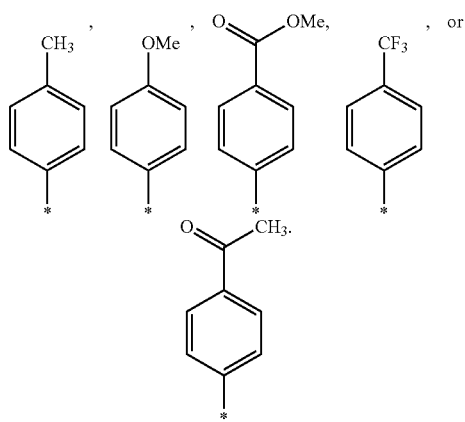

In some embodiments, it may be beneficial to replace the nitro group of any of the foregoing compounds (e.g., the nitro group shown in formula (XIII) with a nitrile group (—CN) or other substituent.

The following synthetic pathways may be used to arrive at compounds of the present invention. Pathway F can be used to synthesize 2-Chloro-5-nitrobenzenesulfonamide for use as an intermediate.

PATHWAY F

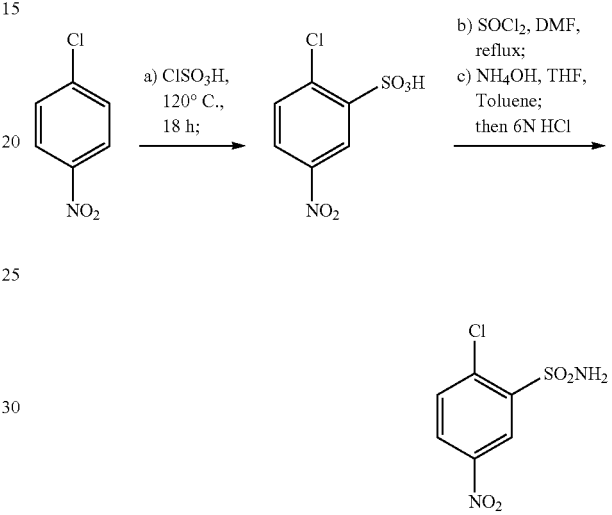

1-Chloro-4 nitrobenzene (6.93 g, 44 mmol) was added to chlorosulphonic acid (20 mL) and heated to 120° C. for 18 hours. After cooling to room temperature, the reaction was poured onto ice. The 2-chloro-5-nitrobenzene sulfonic acid was extracted with dichloromethane (DCM) and the organic phase was washed with brine, dried over MgSO$_4$ and then concentrated to dryness under vacuum. The reaction yielded 8.71 g of crude sulfonic acid and was used directly without further purification.

2-chloro-5-nitrobenzenesulfonic acid (44 mmol) was heated at reflux for 3.5 hours in a mixture of thionyl chloride (22 mL) and dimethylformamide (2 mL). After cooling the reaction mixture to room temperature, the solvents were removed under high vacuum. The crude solid was azeotroped with toluene (3×100 mL) to dryness under vacuum. The final residue was taken up in a mixture of toluene (20 mL) and tetrahydrofuran (50 mL) then cooled to 0° C. Ammonia (50 mL) was added to the stirred reaction mixture, then allowed to warm to room temperature overnight. The solution was acidified using 6 M HCl (pH~4) and extracted with ethyl acetate (3×100 mL). The combined organics were dried over MgSO$_4$, filtered and then concentrated to dryness under vacuum to yield 2-Chloro-5-nitrobenzenesulfonamide as a light brown solid (3.91 g, 38% over 2 steps).

Pathway G yields 4'-methoxy-[1,1'-biphenyl]-3-ol.

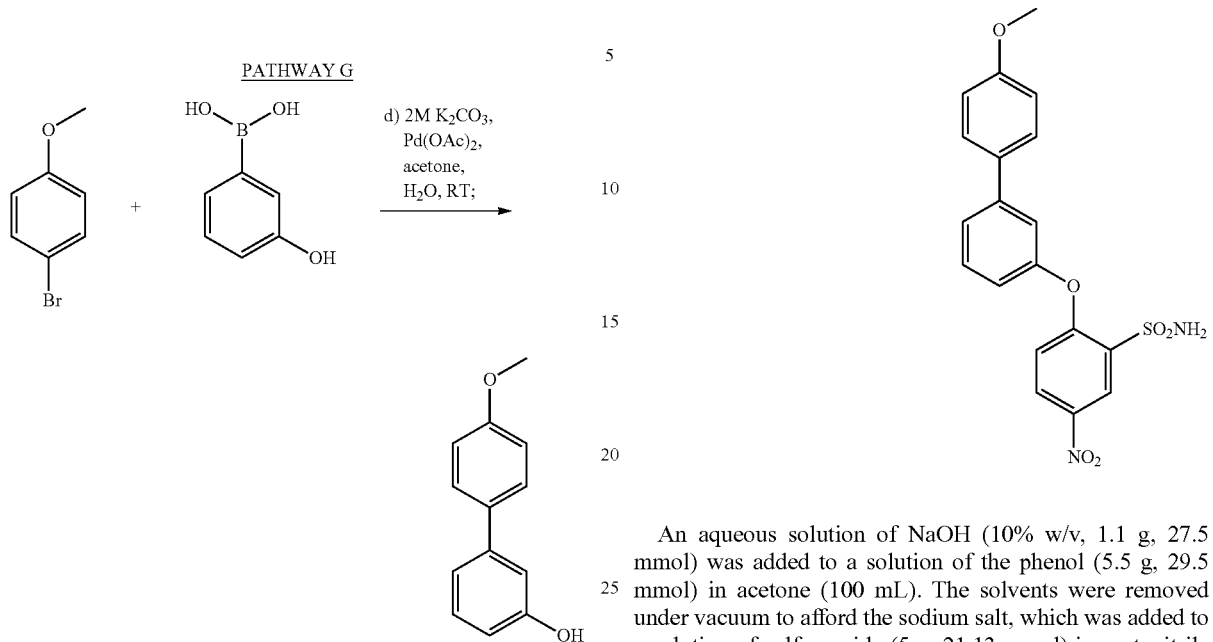

Nitrogen was bubbled through a mixture of 1-bromo-4-methoxybenzene (5.0 g, 26.8 mmol), 3-hydroxyphenylboronic acid (6.8 g, 49.6 mmol), aqueous potassium carbonate (2 M, 20 mL, 40 mmol), acetone (170 mL) and $H_2O$ (300 mL) for 5 minutes. $Pd(OAc)_2$ (800 mg, 3.55 mmol) was added and the mixture was stirred under a nitrogen atmosphere at room temperature for 20 minutes, after which time LC-MS analysis showed the reaction to be complete. The reaction mixture was concentrated under vacuum then diluted with ethyl acetate (200 mL). The resulting suspension was filtered through a pad of celite, and the aqueous phase was then separated and extracted with EtOAc (2×100 mL). The combined organics were dried over $MgSO_4$, filtered and concentrated to dryness under vacuum. The crude product was loaded onto a 340 g Biotage silica cartridge and purified by Biotage chromatography (eluting with iso-hexane/EtOAc, gradient 0 to 50%). The target compound 4'-methoxy-[1,1'-biphenyl]-3-ol was isolated as a white solid (5.66 g, 78% yield).

Pathway H produced 2-((4'-methoxy-[1,1'-biphenyl]-3-yl)oxy)-5-nitrobenzenesulfonamide.

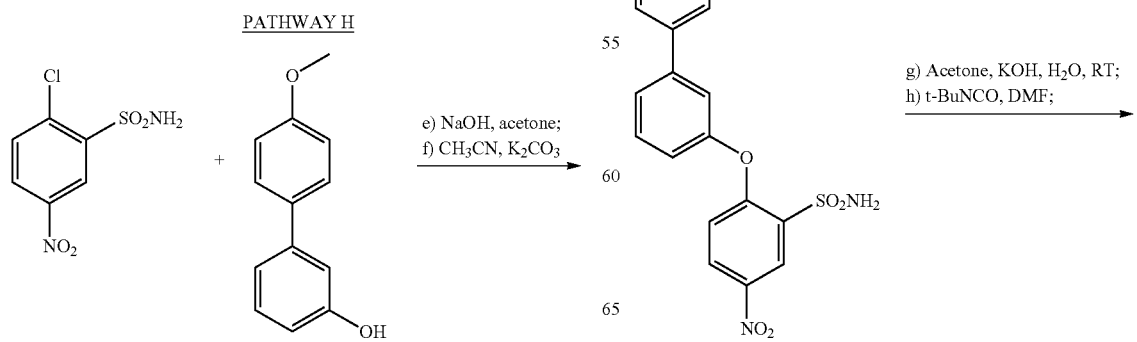

An aqueous solution of NaOH (10% w/v, 1.1 g, 27.5 mmol) was added to a solution of the phenol (5.5 g, 29.5 mmol) in acetone (100 mL). The solvents were removed under vacuum to afford the sodium salt, which was added to a solution of sulfonamide (5 g, 21.13 mmol) in acetonitrile (100 mL). The mixture was heated to reflux, potassium carbonate (2.0 g) was added and the mixture was heated at reflux for a further 18 hours. The reaction mixture was concentrated under vacuum, diluted with water (25 mL) and acidified with concentrated HCl (pH~1). The aqueous phase was extracted with EtOAc (3×50 mL) and the combined organic phases were washed with brine, dried over $MgSO_4$, filtered and concentrated to dryness. The crude product was loaded onto a Biotage silica cartridge (100 g) and purified by Biotage chromatography (eluting with iso-hexane/EtOAc gradient 0 to 50%). The target compound nitrobenzene sulfonamide was isolated as an off white solid (7, 1.0 g, 50%).

Pathway I can be used to produce N-(tert-butylcarbamoyl)-2-((4'-methoxy-[1,1'-biphenyl]-3-yl)oxy)-5-nitrobenzene-sulfonamide represented by formula (X).

PATHWAY I

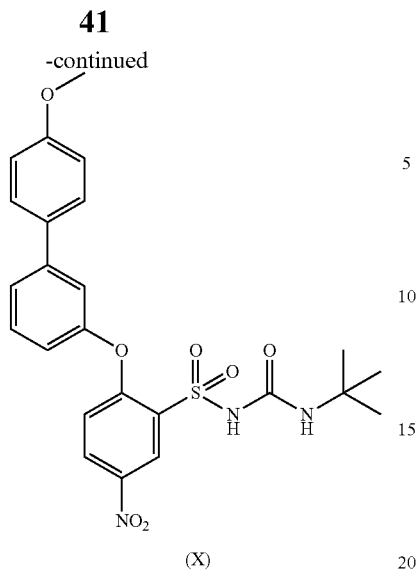

(X)

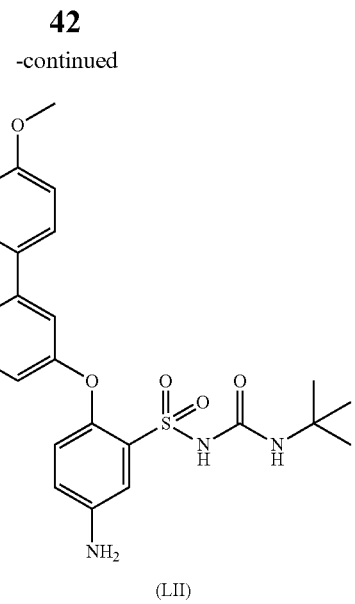

(LII)

A solution of the sulfonamide (2.1 g, 5.24 mmol) in acetone (30 mL) was treated with a solution of potassium hydroxide (295 mg, 5.24 mmol) in water (1.8 mL). After stirring the reaction at room temperature for 15 minutes, the solvents were removed under vacuum. The residue was dissolved in DMF (30 mL), tert-butylisocyanate (1.2 mL, 10.4 mmol) was added and the reaction mixture was stirred at room temperature for 18 hours. The solvents were removed under high vacuum and the crude product was loaded onto a 50 g Biotage silica cartridge and purified by Biotage chromatography (eluting with 1-100% gradient iso-hexane/EtOAc). The crude product was re-dissolved in DMF (15 mL), NaH (60% in oil, 35 mg, 0.87 mmol) was added, followed by tert-butylisocyanate (110 µl, 0.95 mmol). The mixture was stirred at room temperature for 4 hours and then evaporated under high vacuum before loading onto a 50 g silica cartridge. The crude product was purified by Biotage chromatography (eluting 1-100% gradient iso-hexane/EtOAc), obtaining the title compound as an off white solid (Formula (X), 2.6 g, 99%).

5-amino-N-(tert-butylcarbamoyl)-2-((4'-methoxy-[1,1'-biphenyl]-3-yl)oxy)benzene-sulfonamide, or Formula (LII) is made from Formula (X) according to Pathway J.

The nitrobenzene sulphonylurea (Formula (X), 2.6 g, 5.2 mmol) was heated with iron powder (1.74 g, 31 mmol), ethanol (15 mL), acetic acid (15 ml) and H₂O (7.5 mL) at 55° C. for 3 hours. After cooling to room temperature the reaction was diluted with EtOAc, the resulting suspension was then filtered through a small pad of celite. The filtrate was washed with 2 M KOH and the aqueous layer was extracted with EtOAc. The combined organics were washed with brine, dried over MgSO₄, filtered and concentrated under vacuum to yield the desired product as an off white solid (Formula (LII), 2.4 g, 98% yield).

Pathway K yields N-(tert-butylcarbamoyl)-5-chloro-2-((4'-methoxy-[1,1'-biphenyl]-3-yl)oxy) benzenesulfonamide (Formula (CX)).

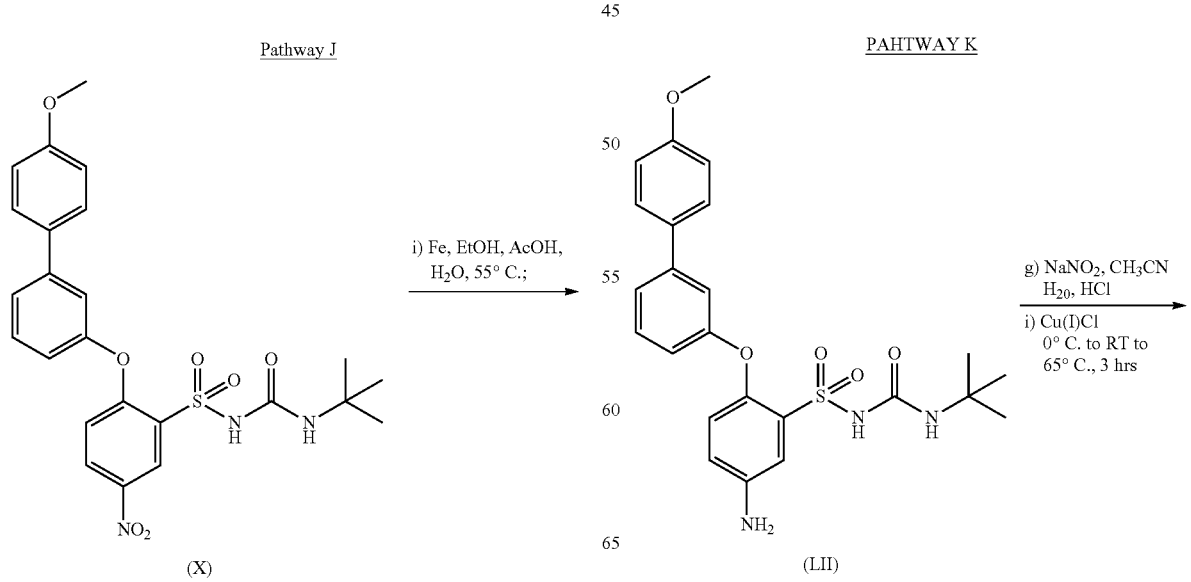

Pathway J / PAHTWAY K

-continued

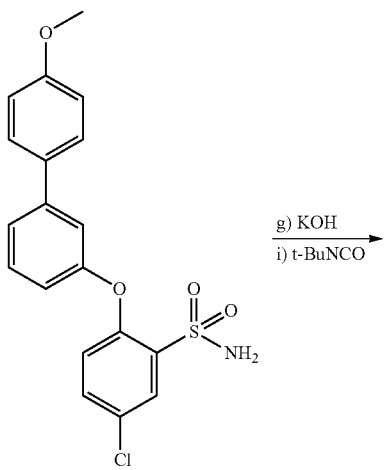

g) KOH
i) t-BuNCO

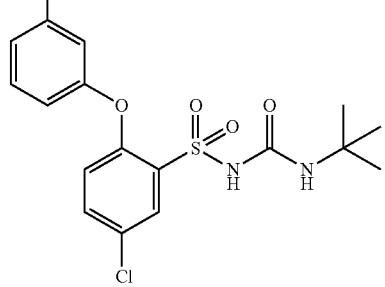

(CX)

The amino benzene sulfonamide (Formula (LII), 150 mg, 0.3198 mmol) was dissolved in acetonitrile (3 mL) and cooled to 0° C. Concentrated HCl (400 µL) was then added, followed by NaNO$_2$ (26.5 mg, 0.3838 mmol) and the mixture was then stirred for 20 minutes. A solution of Cu(I)Cl (63.3 mg, 0.6396 mmol) in H$_2$O (1 mL) was added and the mixture was stirred for a further 18 hours, allowing to warm to room temperature, after which time LC-MS analysis showed 5-10% conversion. Further Cu(I)Cl (60 mg) was added to the reaction and after heating to 65° C. for a further 3 hours, full conversion was confirmed by LC-MS. The reaction mixture was concentrated under vacuum and then diluted with water. The aqueous phase was extracted with EtOAc (3×50 mL). The combined organic phases were washed with brine, dried over MgSO$_4$, filtered and concentrated to dryness under vacuum. The crude solid was dissolved in acetone (2 mL) and added to a solution of KOH (1.8 mg) in H$_2$O (300 µL). The reaction mixture was stirred for 20 minutes before concentrating to dryness under vacuum. The solid was dissolved in DMF (2 mL) and tert-butylisocyanate (23 µL) was added and the reaction was stirred for 18 hours. The crude product was filtered through a syringe filter before purifying by preparative HPLC to give the desired product as an off-white solid (Formula (CX), 50 mg, 32% yield).

Pathway L makes 5-bromo-N-(tert-butylcarbamoyl)-2-((4'-methoxy-[1,1'-biphenyl]-3-yl)oxy)benzenesulfonamide represented by formula (LXI).

PATHWAY L

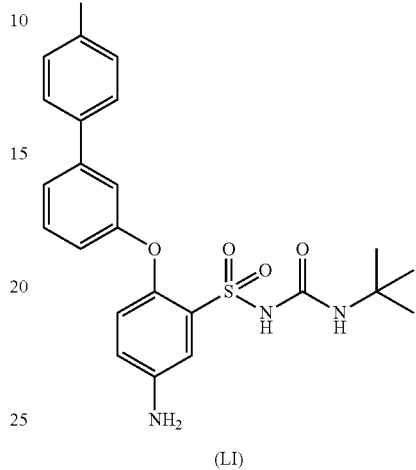

k) NaNO$_2$, CH$_3$CN, H$_2$O, HBr 48%
l) Cu(I)Br
0° C. to RT

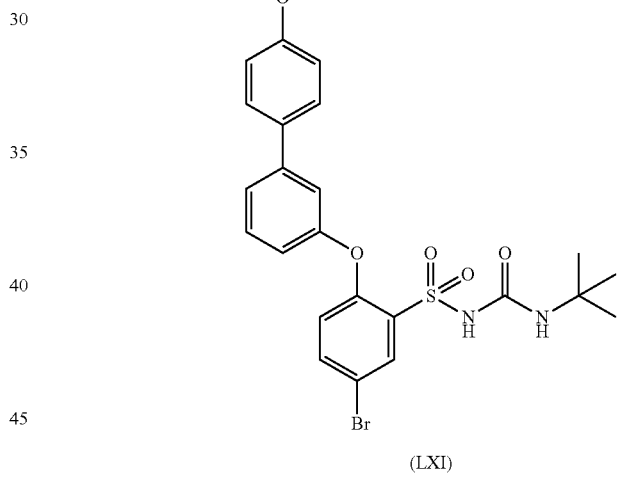

Hydrobromic acid (48%, 3.6 mL) was added to a stirred solution of NaNO$_2$ (318 mg, 4.606 mmol) and amino benzene sulfonamide (Formula (LI), 1.8 mg, 3.838 mmol) in CH$_3$CN (40 mL) and water (9 mL) at 0° C. The reaction mixture was maintained at 0° C. for 15 minutes and Cu(I)Br (1.21 g, 8.4436 mmol) was added. The mixture was allowed to warm to room temperature over 18 hours. The reaction mixture was diluted with water (50 mL) and extracted with EtOAc (3×100 mL). The combined organics were dried over MgSO$_4$, filtered and concentrated to dryness under vacuum. The crude product was loaded onto a 100 g silica cartridge and purified by Biotage chromatography (eluting with iso-hexane/EtOAc, gradient 0 to 100%), to yield the target compound 5-bromo-N-(tert-butylcarbamoyl)-2-((4'-methoxy-[1,1'-biphenyl]-3-yl)oxy)benzenesulfonamide as a white solid (Formula LXI, 0.92 g, 96.4%).

Pathway M provides for the synthesis of an intermediate N-(tert-butylcarbamoyl)-5-cyano-2-((4'-methoxy-[1,1'-biphenyl]-3-yl)oxy)benzenesulfonamide, formula (LXII), from the compound represented by formula (LI).

methoxy-[1,1'-biphenyl]-3-yl)oxy)benzenesulfonamide, formula (LXIII), from compound represented by formula (LXI) provided by Pathway L, as described below in Pathway N.

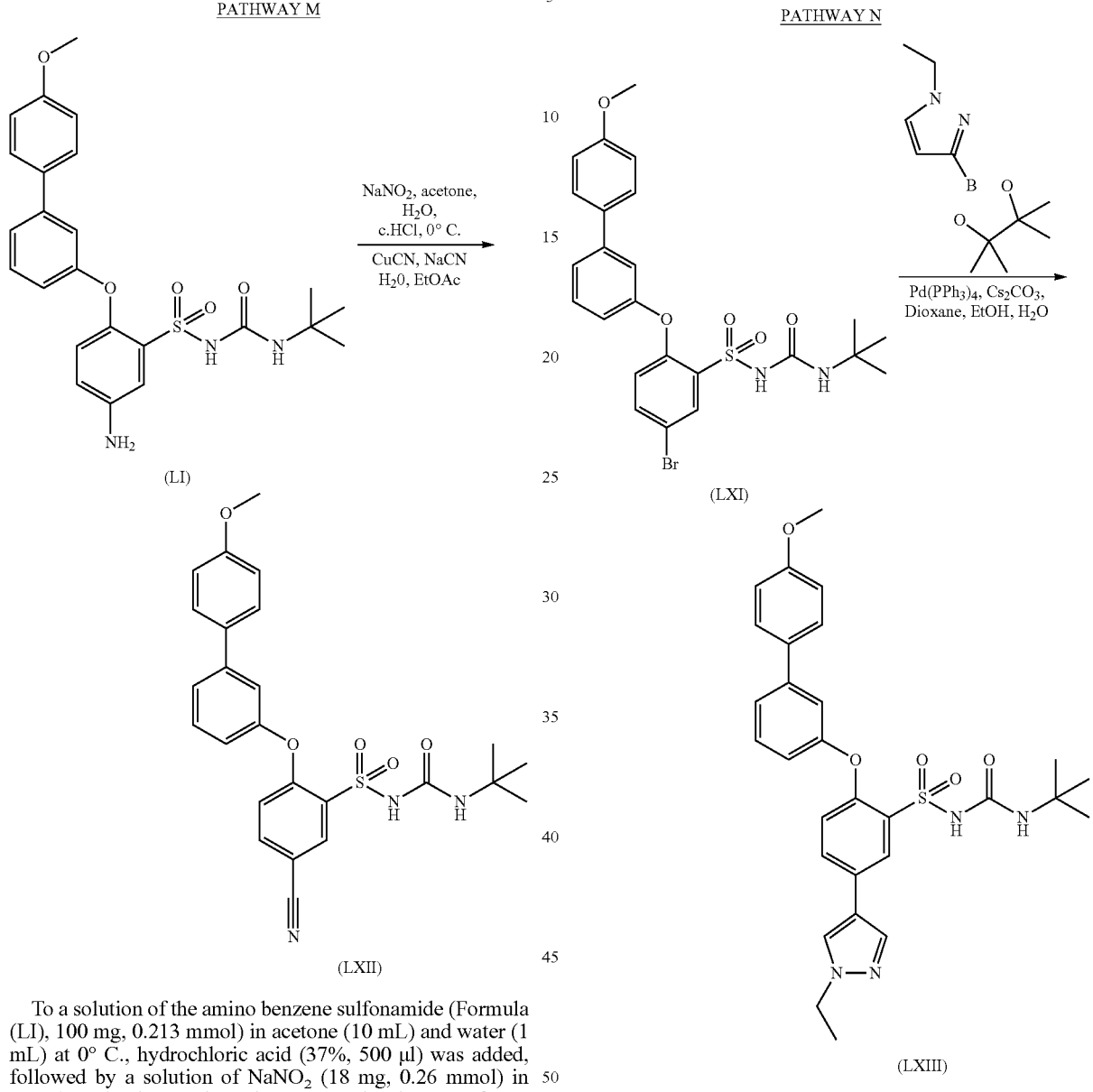

To a solution of the amino benzene sulfonamide (Formula (LI), 100 mg, 0.213 mmol) in acetone (10 mL) and water (1 mL) at 0° C., hydrochloric acid (37%, 500 µl) was added, followed by a solution of NaNO$_2$ (18 mg, 0.26 mmol) in H$_2$O (1 mL). The reaction mixture was stirred at 0° C. for 20 minutes after which time it was poured onto a solution of NaCN (45 mg, 0.92 mmol) and CuCN (30 mg, 0.33 mmol) in H$_2$O (10 mL) and EtOAc (5 mL), stirring at room temperature for 4 hours. The reaction mixture was diluted and extracted with EtOAc (3×100 mL). The combined organics were washed with brine, dried over MgSO$_4$, filtered and then concentrated to dryness under vacuum. The crude product was diluted with DMSO (1.5 mL) and then purified by preparative HPLC to yield the target compound N-(tert-butylcarbamoyl)-5-cyano-2-((4'-methoxy-[1,1'-biphenyl]-3-yl)oxy)benzenesulfonamide as a white solid (Formula (LXII), 7.51 mg, 7.3%).

Synthesis of various compounds from compound represented by formula (LXI) is described.

In some embodiments, a test Suzuki provides N-(tert-butylcarbamoyl)-5-(1-ethyl-1H-pyrazol-4-yl)-2-((4'-

The bromo benzene sulfonamide (Formula (LXI), 50 mg, 0.09375 mmol), Pd(PPh$_3$)$_4$ (10.8 mg, 0.009375 mmol), Cs$_2$CO$_3$ (73.11 mg, 0.2249 mmol), dioxane (1 mL), EtOH (0.5 mL), H$_2$O (0.15 mL) and the boronate (61 mg, 0.1875 mmol) were added to a stem tube under N$_2$. The reaction tube was degassed for 5 minutes, sealed and then heated to 80° C. for 18 hours, after which time LC-MS analysis showed ~60% conversion. The solvents were removed under vacuum and the residue was diluted with water and extracted with DCM. The organic phase was removed and concentrated to dryness under vacuum. The crude product was dissolved in DMSO (1.5 mL) and then purified by preparative HPLC to yield the target compound as an off-white solid (Formula (LXIII), 14.4 mg, 28%).

Using C-Linked palladium array chemistry, as shown in Pathway O below, arrives at a number of compounds based on the compound represented by formula (XXII) and starting with the compound represented by formula (LXI). This is shown in Pathway O, below, where Table 1.1 shows which boronate compound reactant and in what amount to use to yield which product.

PATHWAY O

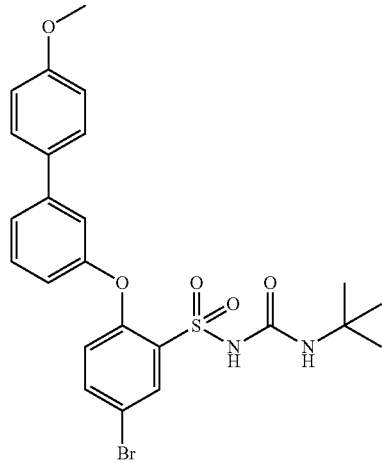

(LXI)

p) RB(OH)$_2$, Pd(PPh$_3$)$_4$, Dioxane, EtOH, H$_2$0, Cs$_2$CO$_3$

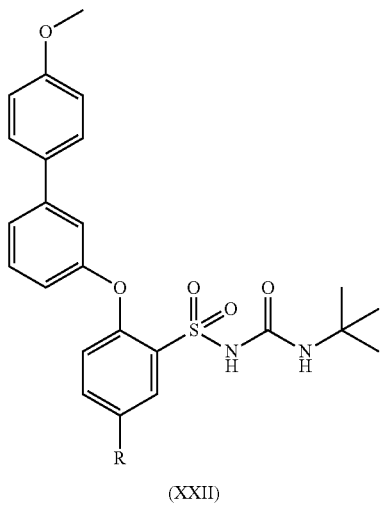

(XXII)

TABLE 1.1

| C-Linked Palladium Array Chemistry | | |
|---|---|---|
| Boronate reactant | Amount (mg); Amount (mmol); Yield (mg, %) | Target Compound/product |
|  | 49.63; 0.1687; 20 mg, 17% | (LXIV) |

TABLE 1.1-continued
C-Linked Palladium Array Chemistry
| Boronate reactant | Amount (mg); Amount (mmol); Yield (mg, %) | Target Compound/product |
|---|---|---|
| 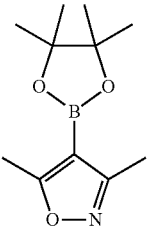 | 37.64; 0.1687; 6 mg, 9% | 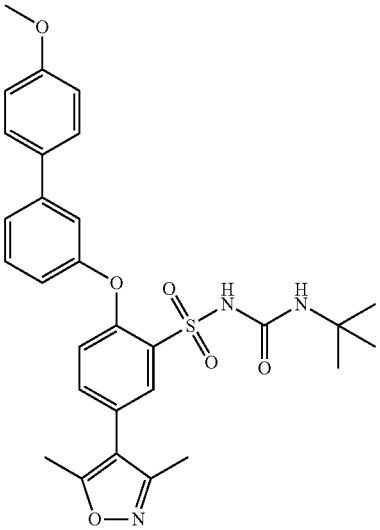 (LXV) |
| 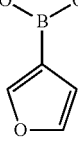 | 18.88; 0.1687; 33 mg, 56% | 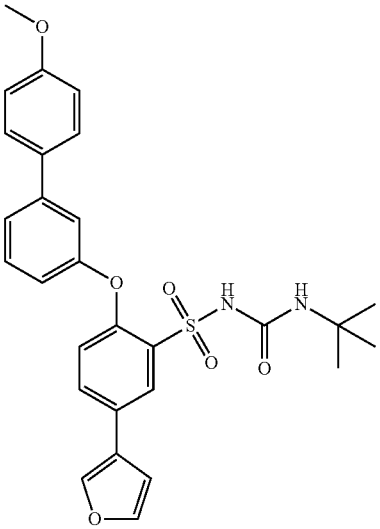 (LXVI) |

TABLE 1.1-continued

C-Linked Palladium Array Chemistry

| Boronate reactant | Amount (mg); Amount (mmol); Yield (mg, %) | Target Compound/product |
|---|---|---|
| 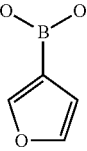 | 18.88; 0.1687; 33 mg, 56% | 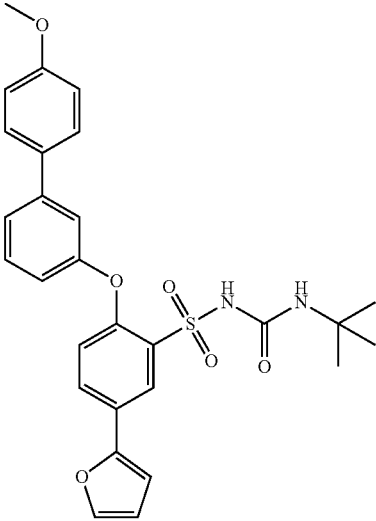 (LXVII) |
| 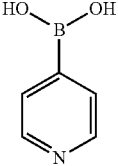 | 20.74; 0.1687; 7.8 mg, 13% | 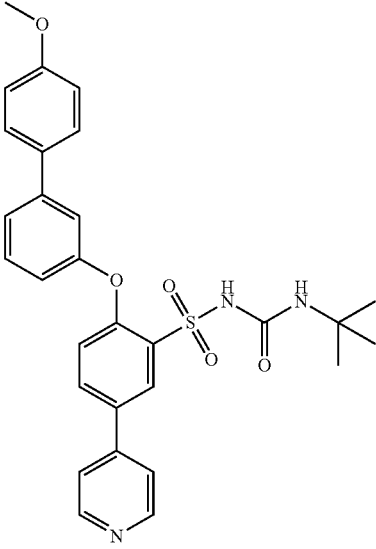 (LXVIII) |

For each of the target reactions, bromo benzene sulfonamide (Formula (LXI), 60 mg, 0.1125 mmol), Pd(PPh$_3$)$_4$ (13 mg, 0.01125 mmol), Cs$_2$CO$_3$ (73.11 mg, 0.2249 mmol), dioxane (1 mL), EtOH (0.5 mL), H$_2$O (0.15 mL) and the corresponding boronates, as indicated in Table 1.1, were added to a stem tube under N$_2$. The reaction tubes were degassed for 5 minutes, sealed and then heated to 80° C. for 18 hours. The solvents were removed under vacuum and diluted with water, then extracted with DCM. The organic phase was removed and concentrated to dryness under vacuum. The crude products were dissolved in DMSO (1.5 mL) and then purified by preparative HPLC to yield the desired target compounds represented by formulas (LXIV), (LXV), (LXVI), (LXVII), and (LXVIII) with yields as indicated in Table 1.1.

The Stille reaction shown in Pathway P can produce N-(tert-butylcarbamoyl)-2-((4'-methoxy-[1,1'-biphenyl]-3-yl)oxy)-5-(2-methoxythiazol-4-yl)benzenesulfonamide, formula (LXIX), from (LXI).

PATHWAY P

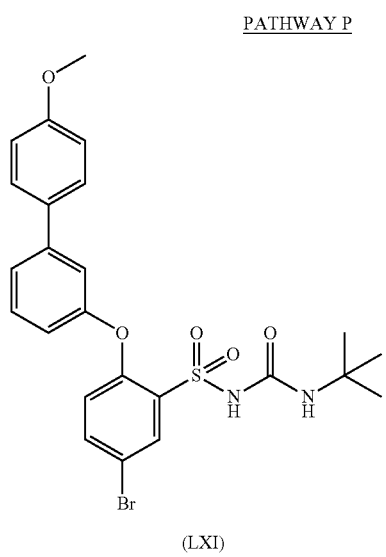

Pathway Q, shown below, produces 5-acetyl-N-(tert-butylcarbamoyl)-2-((4'-methoxy-[1,1'-biphenyl]-3-yl)oxy)benzenesulfonamide, formula (LXX), from (LXI).

PATHWAY Q

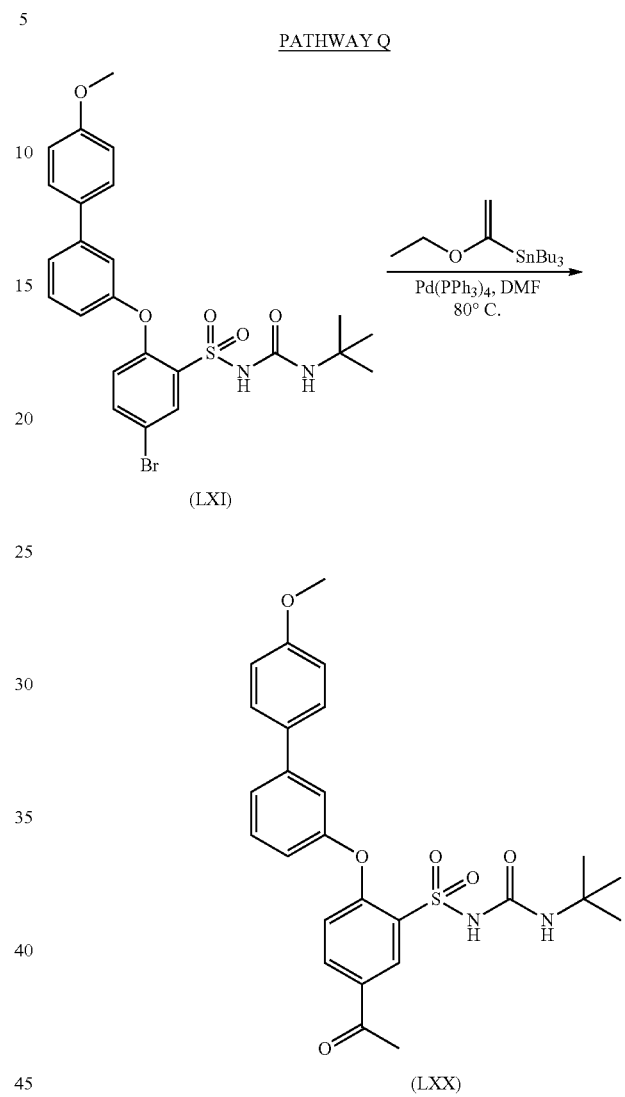

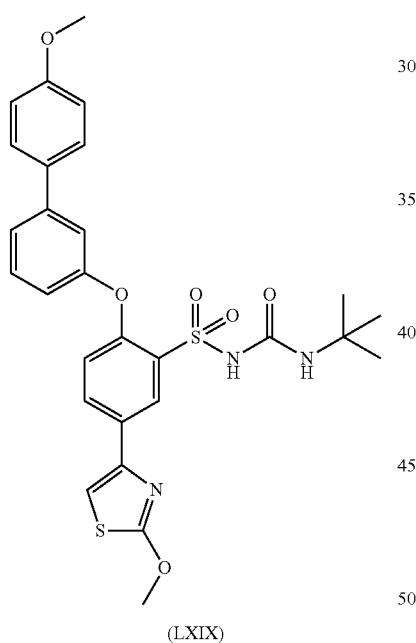

Pd(PPh$_3$)$_4$ (13 mg, 0.01125 mmol) was added to a N$_2$ flushed reaction tube containing the sulphonamide (Formula (LXI), 60 mg, 0.1125 mmol), DMF (1.5 mL) and the tributyl stannyl thiazole (68 mg, 0.1688 mmol). The reaction tube was flushed with N$_2$ before sealing the tube and heating to 80° C. for 18 hours, after which time, LC-MS analysis confirmed complete conversion. The crude product was filtered and then purified by preparative HPLC to yield the product as a white solid (Formula (LXIX), 29 mg; 45%).

The tributyl-(1-ethoxyvinyl)stannane (67.7 mg, 0.1875 mmol) was added to a solution of the bromo-benzenesulfonurea (Formula (LXI), 80 mg, 0.150 mmol) in DMF (1.5 mL) under N$_2$. Pd(PPh$_3$)$_4$ (17 mg, 0.015 mmol) was added and the reaction tube was flushed with N$_2$, sealed and then heated to 80° C. for 18 hours. LC-MS analysis showed near complete reaction to the vinyl ether intermediate. The DMF was removed under high vacuum and HCl (2M, 1 mL) was added followed by THF (1 mL). The reaction was stirred for 1 hour after which time LC-MS analysis confirmed complete conversion to the desired product. The solvents were removed under vacuum and the residue was diluted with water, extracting with DCM. The organic phase was removed and concentrated to dryness under vacuum. The crude products were dissolved in DMSO (1.5 mL) and purified by preparative HPLC to yield the target compound as a white solid (Formula (LXX), 15.2 mg, 20%).

Methyl 4-fluoro-3-sulfamoylbenzoate, formula (LXXI) is a product of pathway R and an intermediate in synthetic pathways disclosed herein.

PATHWAY R

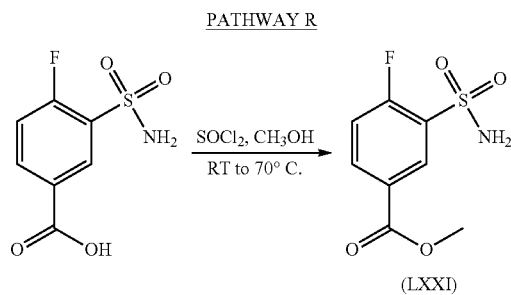

(LXXI)

Thionyl chloride (3 mL) was added to a solution of 4-fluoro-3-sulfamoylbenzoic acid (1.8 g, 8.91 mmol) in methanol (100 mL). The resulting mixture was heated at 70° C. for 3 hours and then evaporated to dryness under vacuum. The resulting crude solid was re-dissolved in DCM and washed with water. The organic phase was dried over $MgSO_4$, filtered and evaporated to dryness to provide desired product as a beige solid (Formula (LXXI), 1.5 g, 78% yield).

In Pathway S, Methyl 4-((4'-methoxy-[1,1-biphenyl]-3-yl)oxy)-3-sulfamoylbenzoate, Formula (LXXII), is produced.

An aqueous solution of NaOH (40% w/v, 380 mg, 27.5 mmol) was added to a solution of the phenol (1.9 g, 9.5 mmol) in acetone (50 mL). The reaction mixture was stirred for 10 minutes then evaporated to dryness under high vacuum. The residue was dissolved in acetonitrile (60 mL) and then the sulfonamide (Formula (LXXI), 2.0 g, 8.6 mmol) and potassium carbonate (840 mg) were added. The resulting mixture was heated to 90° C. for 18 hours. The solvents were removed under vacuum and the crude solid obtained was partitioned between water and EtOAc (100 mL), acidifying to pH~1 with concentrated HCl. The aqueous phase was removed and re-extracted with EtOAc (2×100 mL) and the combined organic phases were washed with brine, dried over $MgSO_4$, filtered and evaporated to dryness. The crude product was loaded with DCM, onto a silica cartridge (25 g) and then purified by Biotage chromatography (eluting with iso-hexane/EtOAc gradient 20 to 100% EtOAc). The target compound nitrobenzene sulfonamide was isolated as a white solid (Formula (LXXII), 2.64 g, 75%).

Pathway T produces Methyl 3-(N-(tert-butylcarbamoyl)sulfamoyl)-4-((4'-methoxy-[1,1'-biphenyl]-3-yl)oxy) benzoate, represented by formula (LXXIII), from compound formula (LXXII).

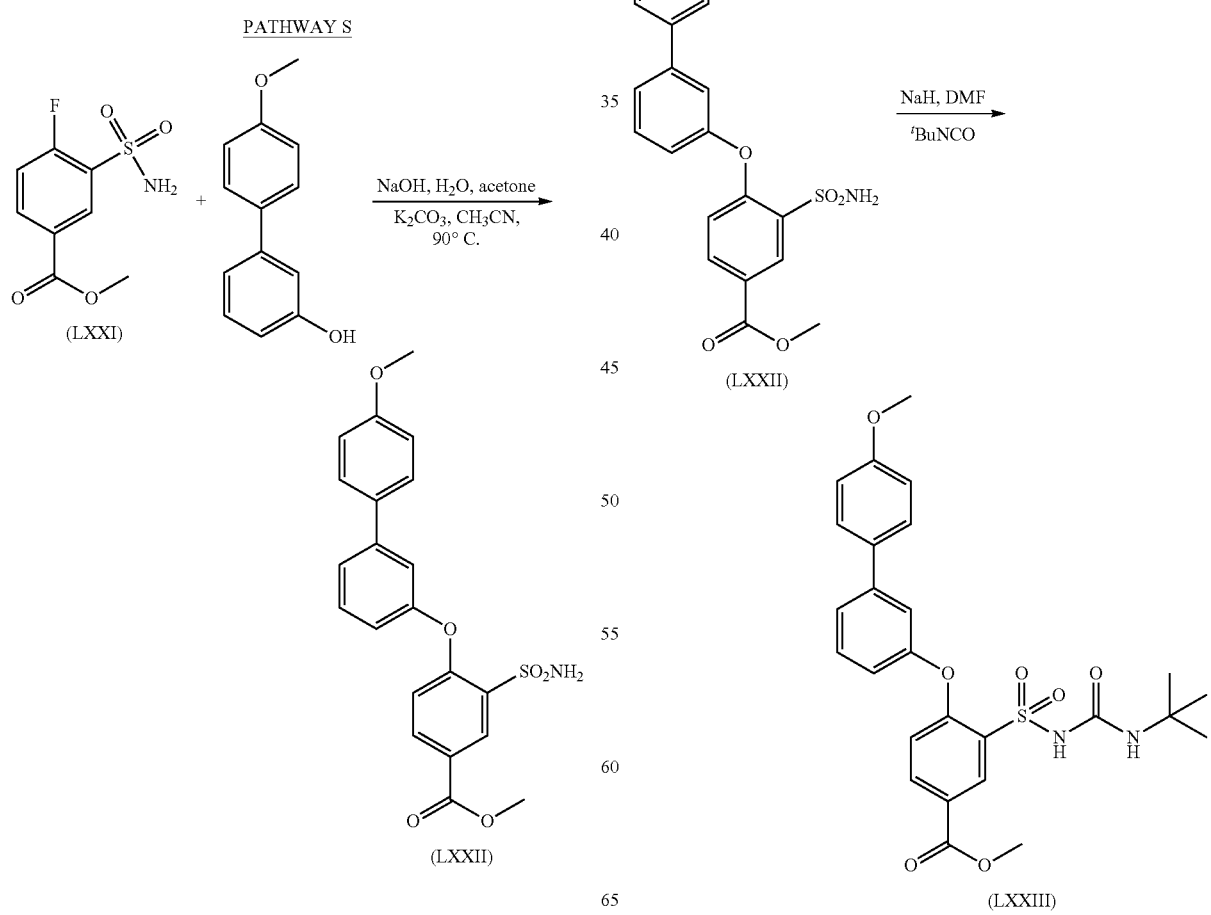

Sodium hydride (60% in oil, 281 mg, 7.0 mmol) was added to a solution of the nitrobenzene sulfonamide (Formula (LXXII), 2.64 g, 6.4 mmol) in DMF (50 mL). The mixture was stirred for 10 minutes at ambient temperature before the addition of tert-butylisocyanate (1 mL, 8.7 mmol). The resulting mixture was stirred overnight at room temperature. The solvents were removed under high vacuum and then the crude solid obtained was partitioned between water and EtOAc (50 mL), before acidifying the aqueous with 1 M HCl (pH~1). The aqueous phase was removed and re-extracted with EtOAc (2×50 mL) and the combined organic phases were dried over MgSO4, filtered and evaporated to dryness under vacuum to yield the desired product (Formula (LXXIII), 2.8 g, 86%).

Below, 3-(N-(tert-butylcarbamoyl)sulfamoyl)-4-((4'-methoxy-[1,1'-biphenyl]-3-yl)oxy) benzoic acid, formula (LXXIV) is produced from (LXXIII) by pathway U.

PATHWAY U

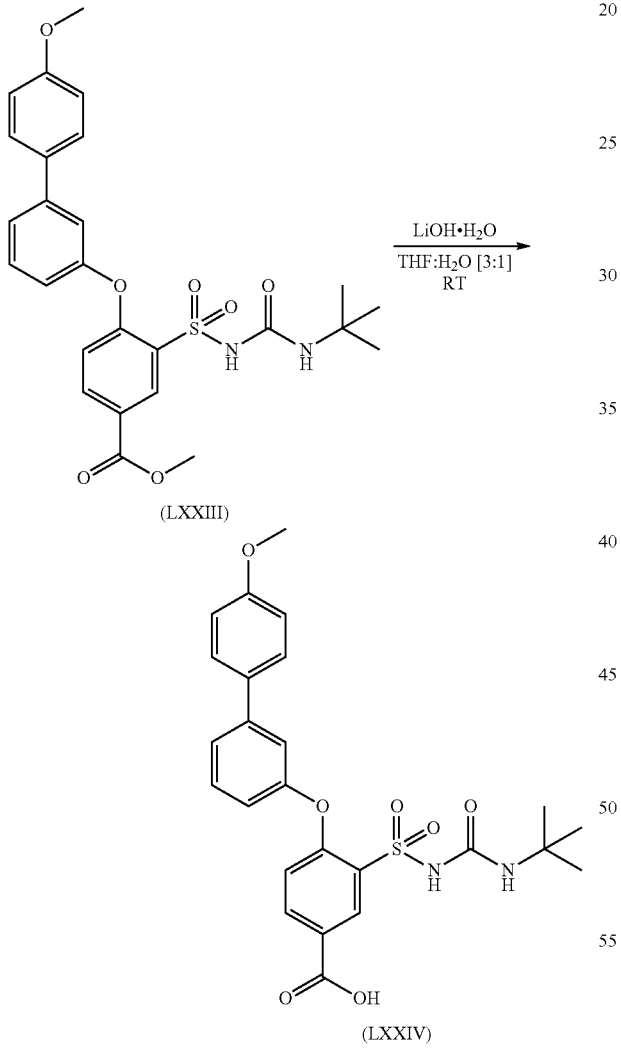

(LXXIV)

Lithium hydroxide monohydrate (262 mg, 6.243 mmol) was added to a solution of the methyl ester (Formula (LXXIII), 2.0 g, 3.902 mmol) in THF (100 mL) and H₂O (33 mL). The mixture was stirred at room temperature for 18 hours and then evaporated to dryness under vacuum. The residue was dissolved in H₂O and acidified using concentrated HCl (pH~1). The resulting white solid was removed by filtration, re-dissolved in EtOAc (50 mL), and dried by passing through a hydrophobic filter before evaporating to dryness under vacuum to give the desired product as a white solid (Formula (LXXIV), 1.7 g, 87% yield).

Synthesis of various compounds from the compound represented by formula (LXXIV) is described.

Pathway V shows synthesis of 3-(N-(tert-butylcarbamoyl)sulfamoyl)-4-((4'-methoxy-[1,1-biphenyl]-3-yl)oxy)-N,N-dimethylbenzamide, formula (LXXV), from compound formula (LXXIV).

PATHWAY V

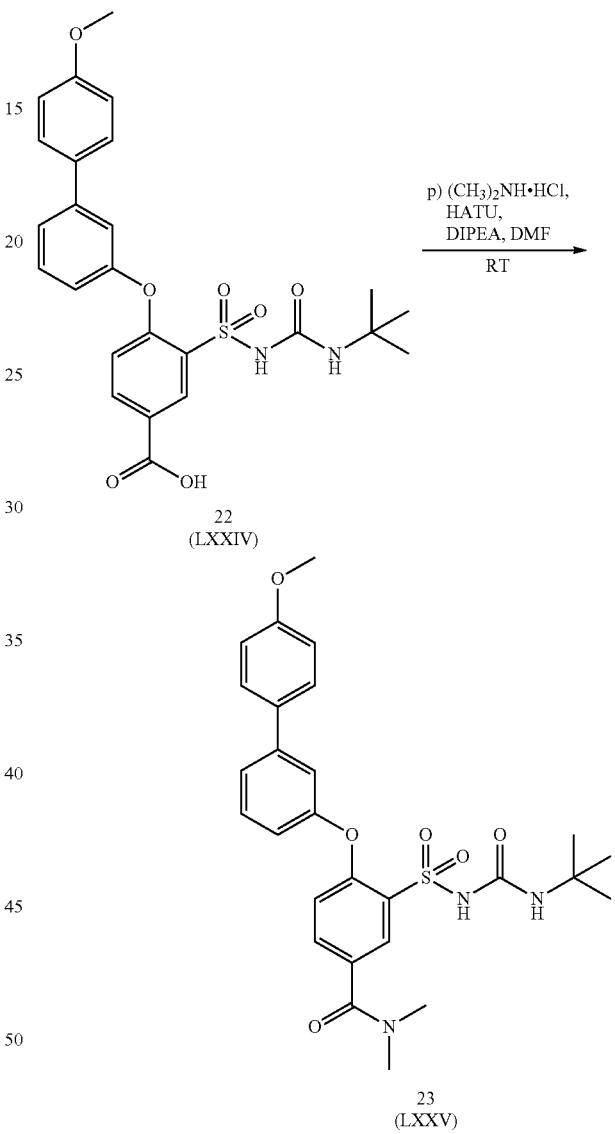

The amine (16 mg, 0.196 mmol), HATU (71 mg, 0.1868 mmol) and DIPEA (120 µL) were successively added to a solution of the acid (Formula LXXIV), 85 mg, 0.170 mmol) in DMF (4 mL). The resulting mixture was stirred at room temperature for 18 hours, after which time LC-MS analysis confirmed ~80% conversion to the target compound. The DMF was removed under high vacuum and the residue taken up in in EtOAc (20 mL) and H₂O (10 mL). The aqueous phase was acidified using concentrated HCl (pH~2) and then extracted with EtOAc (2×20 mL). The combined organics were dried over MgSO₄, filtered and evaporated to dryness. The crude product was dissolved in DMSO (1.5 mL), filtered and then purified by preparative HPLC to yield a white solid (Formula (LXXV), 41 mg, 98.3%).

Pathway W shows an amide array synthesis of various amides as listed in Table 1.2 from compound Formula (LXXV).
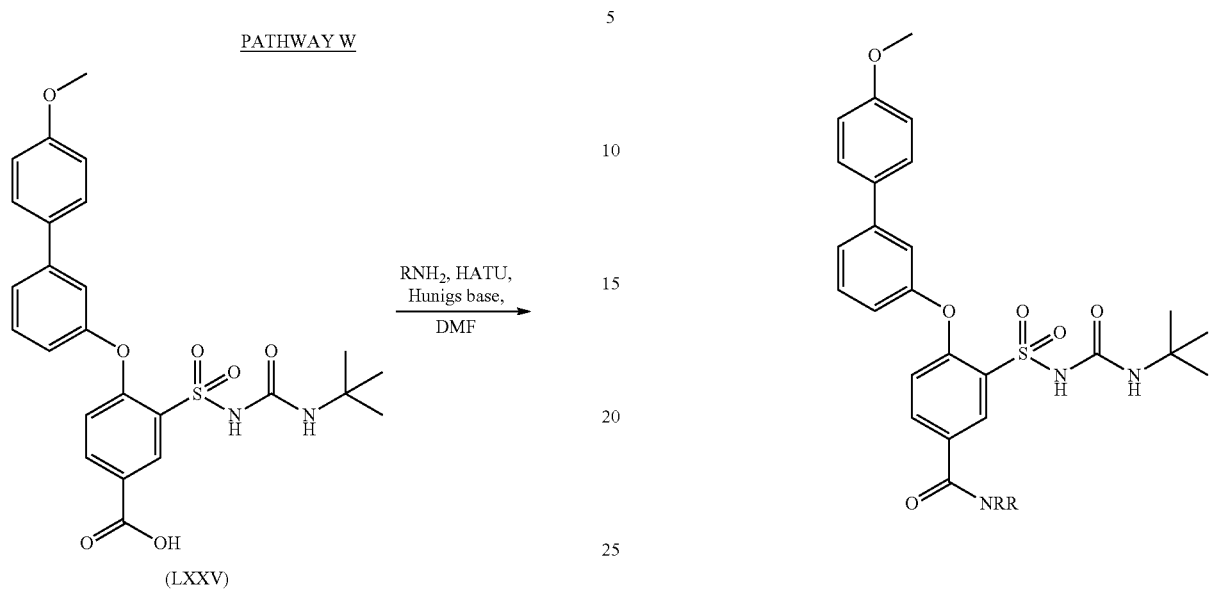
TABLE 1.2
Amide Array: Synthesis of various amides from (LXXV)
| Amine | Amount (mg); Amount (mmol); Yield (mg; %) | Target Compound |
|---|---|---|
| ⟋NH₂Cl | 16.25; 0.2407; 54 mg; 65% | 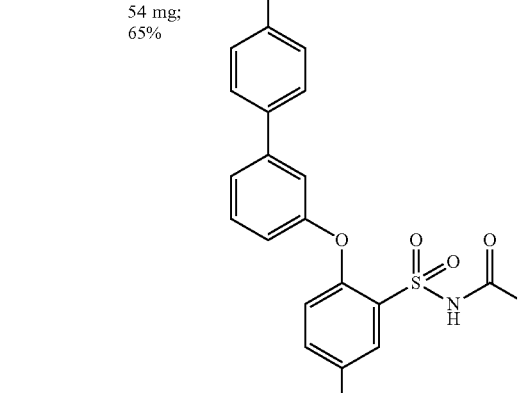 (LXXVI) |

TABLE 1.2-continued
Amide Array: Synthesis of various amides from (LXXV)
| Amine | Amount (mg); Amount (mmol); Yield (mg; %) | Target Compound |
|---|---|---|
| H₂N⌒ | 10.85; 0.2407; 28 mg; 33% | 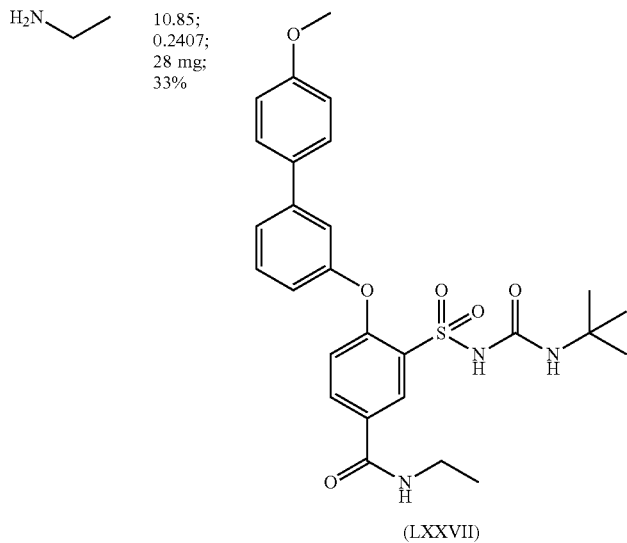<br>(LXXVII) |
| NH₄Cl | 12.88; 0.2407; 49 mg; 61% | 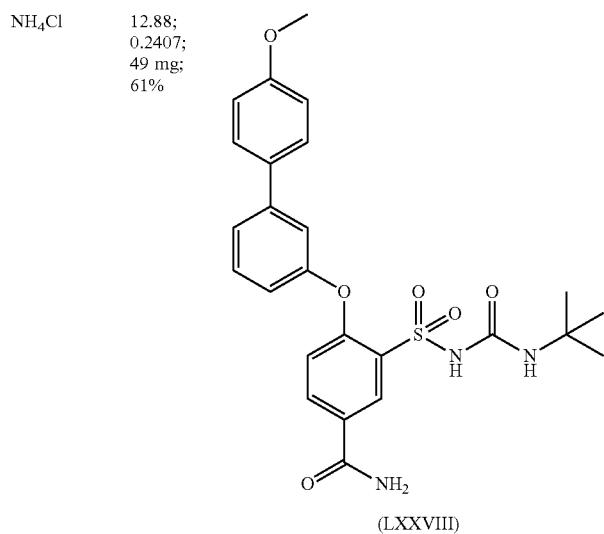<br>(LXXVIII) |

TABLE 1.2-continued
Amide Array: Synthesis of various amides from (LXXV)
| Amine | Amount (mg); Amount (mmol); Yield (mg; %) | Target Compound |
|---|---|---|
| HN⟨morpholine⟩ | 20.97; 0.2407; 31 mg; 34% | 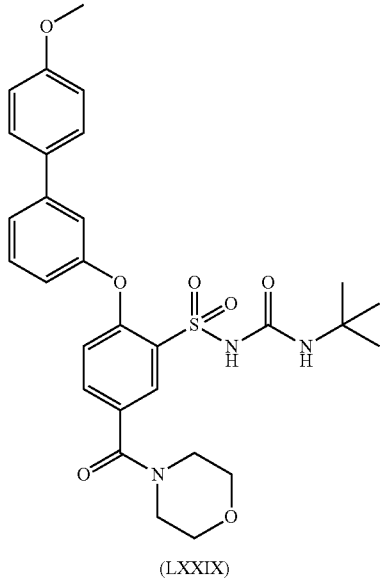 [SMILES: COc1ccc(-c2cccc(Oc3ccc(C(=O)N4CCOCC4)cc3S(=O)(=O)NC(=O)NC(C)(C)C)c2)cc1] (LXXIX) |
| H₂N-CH₂CH₂-O-CH₃ | 18.08; 0.2407; 63 mg; 71% | 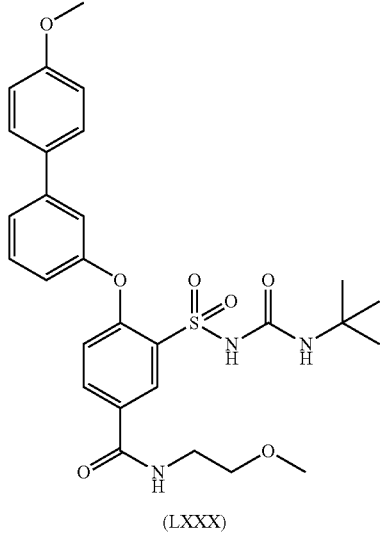 [SMILES: COCCNC(=O)c1ccc(Oc2cccc(-c3ccc(OC)cc3)c2)c(S(=O)(=O)NC(=O)NC(C)(C)C)c1] (LXXX) |

TABLE 1.2-continued
Amide Array: Synthesis of various amides from (LXXV)
| Amine | Amount (mg); Amount (mmol); Yield (mg; %) | Target Compound |
|---|---|---|
| H₂N−CH₂CH₂−N(CH₃)− | 21.22; 0.2407; 33 mg; 36% | (LXXXI) |
| H₂N−CH₂−cyclopropyl | 17.12; 0.2407; 59 mg; 66% | (LXXXII) |
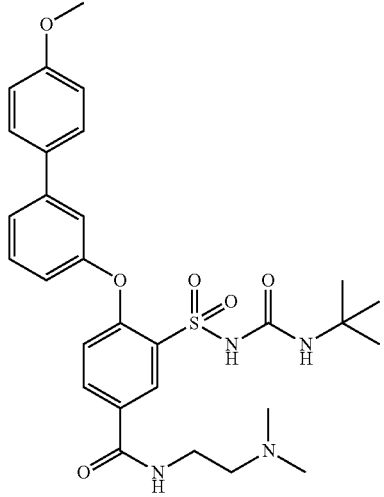
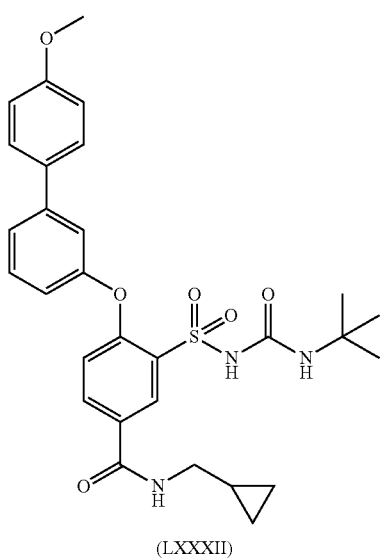 [SMILES: COc1ccc(-c2cccc(Oc3ccc(C(=O)NCC4CC4)cc3S(=O)(=O)NC(=O)NC(C)(C)C)c2)cc1]

TABLE 1.2-continued

| Amide Array: Synthesis of various amides from (LXXV) | | |
|---|---|---|
| Amine | Amount (mg); Amount (mmol); Yield (mg; %) | Target Compound |
| HN⟨azetidine⟩ | 13.74; 0.2407; 12.8 mg; 15% & 23 mg; 27% | (LXXXIII) |
| H₂N–phenyl | 22.42; 0.2407; 28 mg; 30% | (LXXXIV) |

TABLE 1.2-continued
Amide Array: Synthesis of various amides from (LXXV)
| Amine | Amount (mg); Amount (mmol); Yield (mg; %) | Target Compound |
|---|---|---|
| | 26.03; 0.2407; 53 mg; 56% | |
| | 20.24; 0.2407; 16.5 mg; 19% | |
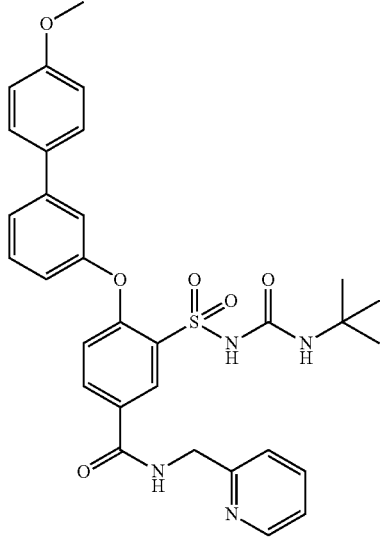
(LXXXV)
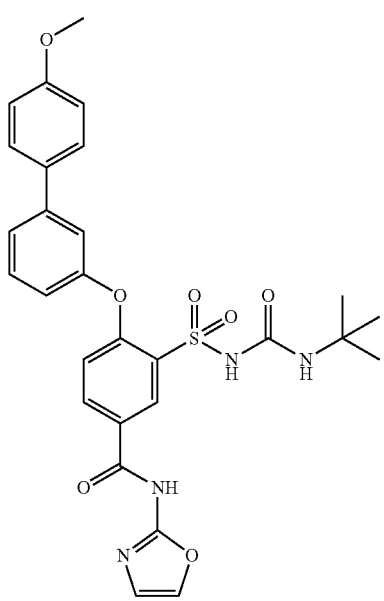
(LXXXVI)

TABLE 1.2-continued

Amide Array: Synthesis of various amides from (LXXV)

| Amine | Amount (mg); Amount (mmol); Yield (mg; %) | Target Compound |
|---|---|---|
| 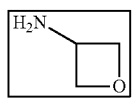 | 17.59; 0.2407; 49 mg; 55% | 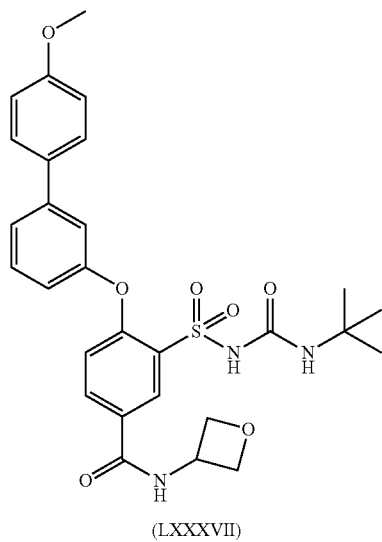 [SMILES: COc1ccc(-c2cccc(Oc3ccc(C(=O)NC4COC4)cc3S(=O)(=O)NC(=O)NC(C)(C)C)c2)cc1]<br>(LXXXVII) |

Generic methods of amide coupling are described.

For each of the target reactions (e.g., Pathway W and Table 2.1), the amine (0.2407 mmol), HATU (114.3 mg, 0.301 mmol) and Hunigs base (167.4 µL) were successively added to a solution of the acid 20 (80 mg, 0.16046 mmol) in DMF (1.5 mL). The resulting mixture was stirred at room temperature for 18 hours. The DMF was removed under high vacuum and the residue was partitioned between EtOAc (20 mL) and H₂O (10 mL). The aqueous phase was acidified using concentrated HCl (to pH~2) and extracted with EtOAc (2×20 mL). The combined organics were dried over MgSO₄, filtered and evaporated to dryness under vacuum. The crude products were re-dissolved in DMSO (1.5 mL), filtered and then purified by preparative HPLC to yield the desired products with formulas (LXXVI), (LXXVII), (LXXVIII), (LXXIX), (LXXX), (LXXXI), (LXXXII), (LXXXIII), (LXXXIV), (LXXXV), (LXXXVI), and (LXXXVII), as shown in Table 2.1.

Pathway X, below, shows the synthesis of N-(tert-butylcarbamoyl)-5-(3-hydroxyazetidine-1-carbonyl)-2-((4'-methoxy-[1,1'-biphenyl]-3-yl)oxy)benzenesulfonamide, formula (LXXXVIII) from compound formula (LXXV).

PATHWAY X

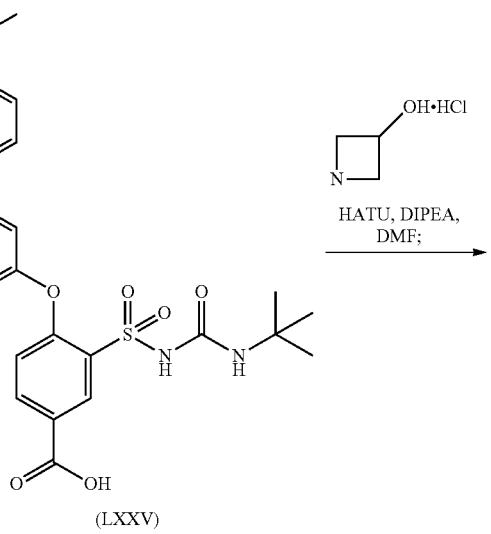

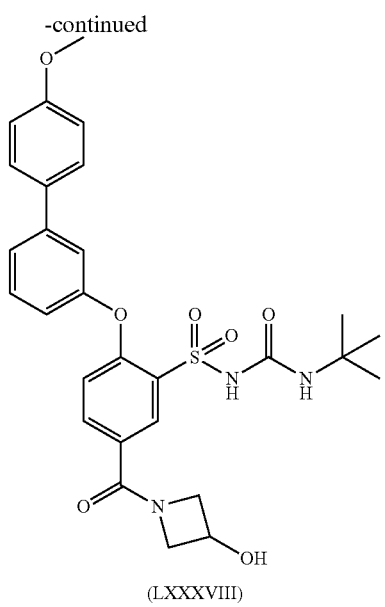

(LXXXVIII)

Azetidin-3-ol hydrochloride (26.4 mg, 0.240 mmol), HATU (67 mg, 0.1767 mmol) and DIPEA (112 µL, 0.642 mmol) were successively added to a solution of acid (Formula (LXXV), 80 mg, 0.161 mmol) in DMF (2 mL). The resulting mixture was stirred at room temperature for 4 hours. The DMF was removed under high vacuum and the residue taken up in EtOAc and H2O. The aqueous phase was acidified using concentrated HCl (to pH~2) and extracted with EtOAc (2×20 mL). The combined organics were dried over MgSO4, filtered and evaporated to dryness under vacuum. The crude product was dissolved in DMSO (~1.5 mL), filtered and then purified by preparative HPLC to yield the title compound as a white solid (Formula (LXXXVIII), 19.2 mg, 21.5%).

Synthesis of various compounds is now shown.

Synthesis of N-(tert-butylcarbamoyl)-2-chloro-5-(trifluoromethyl) benzene-sulfonamide, formula (XC), from (LXXXIX) is shown in Pathway Y.

PATHWAY Y

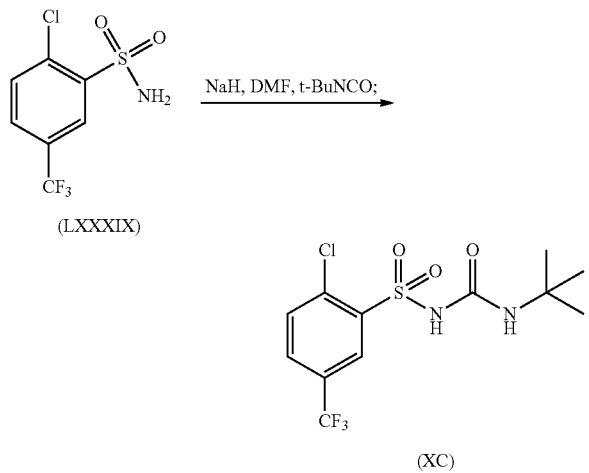

Sodium hydride (60% oil dispersion, 105 mg, 2.6 mmol) was added to a solution of 2-chloro-5-(trifluoromethyl) benzenesulfonamide (Formula (LXXXIX), 612 mg, 2.36 mmol) in DMF (30 mL). The mixture was stirred at room temperature for 10 minutes prior to the addition of tert-butylisocyanate (380 µL, 3.30 mmol). The resulting reaction mixture was stirred overnight at room temperature. The DMF was removed under high vacuum and the crude solid was re-dissolved in EtOAc and H2O, then acidified using 1 N HCl (pH=1). The aqueous phase was extracted with EtOAc and the combined organic phases were dried over MgSO4, filtered and evaporated to dryness under vacuum to yield the desired product (formula (XC)), which was taken to the next step without further purification.

Pathway Z provides N-(tert-butylcarbamoyl)-2-((4'-methoxy-[1,1-biphenyl]-3-yl)oxy)-5-(trifluoromethyl) benzenesulfonamide, formula (XCI).

PATHWAY Z

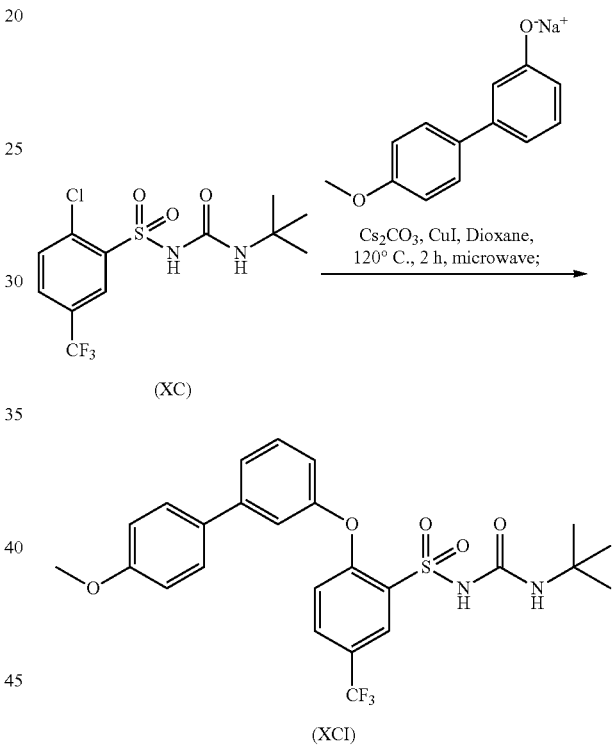

A microwave tube was charged with the sulfonylurea (Formula (XC), 250 mg, 0.7 mmol), the methoxy biphenyl (182 mg, 0.8 mmol), Cs2CO3 (456 mg, 1.39 mmol), CuI (7 mg, 0.036 mmol) and dioxane (1.5 mL). The mixture was heated at 120° C. for 2 hours under microwave irradiation. After cooling to room temperature, the reaction mixture was diluted with EtOAc then water. The reaction was acidified using 1 N HCl to pH 1. The aqueous phase was extracted with EtOAc (×2) and the combined organic phases were dried over MgSO4, filtered and evaporated to dryness. The crude product was dissolved in DMSO (1.5 mL) and then purified by preparative HPLC to yield the desired product as an off white solid (Formula (XCI), 39.1 mg, 11%).

N-(tert-butylcarbamoyl)-2-chloro-5-fluorobenzenesulfonamide, formula (XCIII), is made from (XCII) in Pathway AA.

PATHWAY AA

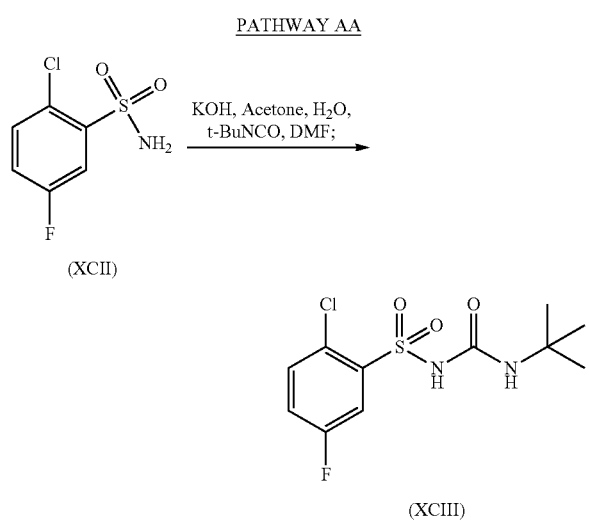

A solution of 2-chloro-5-fluorobenzenesulfonamide (Formula (XCII), 350 mg, 1.69 mmol) in acetone (4 mL) was treated with a solution of potassium hydroxide (95 mg, 1.69 mmol) in H$_2$O (600 µL). The reaction was stirred at room temperature for 15 minutes after which time the solvent was removed under vacuum. The residue was taken up in DMF (4 mL), treated with tert-butylisocyanate (390 µL, 3.39 mmol) and stirred overnight at room temperature. The DMF was removed under high vacuum and the residue was suspended in H$_2$O (5 mL) before addition of 6 N NaOH (5 mL). The reaction was stirred and sonicated, then acidified using 12 N HCl to pH 1. The resulting white solid was collected by filtration, washed with 2 N HCl and dried under suction on a sinter. The solid was dissolved in EtOAc (50 mL) and the combined organic phases were dried over MgSO$_4$, filtered and evaporated to dryness to yield the desired product (Formula (XCIII), 520 mg, 100% yield).

N-(tert-butylcarbamoyl)-5-fluoro-2-((4'-methoxy-[1,1'-biphenyl]-3-yl)oxy)benzene-sulfonamide, formula (XCIV), is prepared from (XCIII) in Pathway AB.

PATHWAY AB

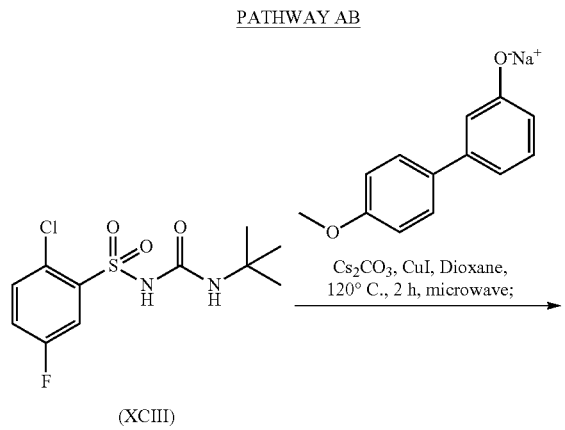

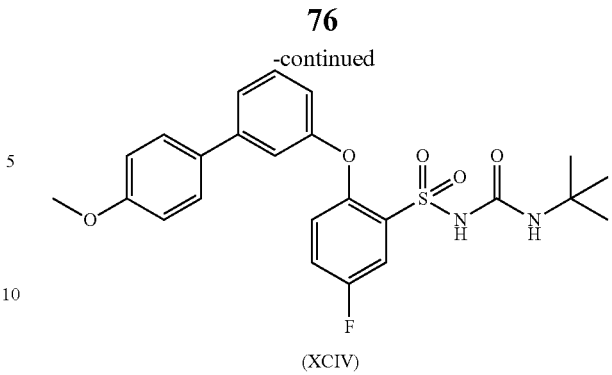

A microwave tube was charged with the sulfonylurea represented by formula (XCIII), 171 mg, 0.55 mmol), the methoxy biphenyl (6, 145 mg, 0.72 mmol), Cs$_2$CO$_3$ (360 mg, 1.1 mmol), CuI (6 mg, 0.031 mmol) and dioxane (1.5 mL). The mixture was heated at 120° C. for 2 hours under microwave irradiation. After returning to room temperature, the reaction mixture was diluted with EtOAc and water. The aqueous phase was acidified using 1 N HCl to pH 1 and then separated, re-extracting with EtOAc (×2). The combined organic phases were dried over MgSO$_4$, filtered and evaporated to dryness under vacuum. The crude product was dissolved in DMSO (1.5 mL) and then purified by preparative HPLC to yield the desired product (Formula (XCIV), 3 mg, 9%).

Pathway AC shows preparation of 2-chloro-5-(methylsulfonyl)benzenesulfonamide, Formula (XCVI) from (XCV).

PATHWAY AC

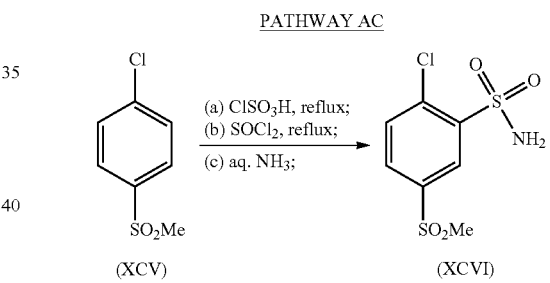

To chlorosulphonic acid (25 mL) cooled on an ice-salt bath, 4-chloro-1-methylsulphonylbenzene (Formula (XCV), 5 g, 26.2 mmol) was carefully added and the mixture was heated to reflux (160° C.) for 1 hour. The reaction was cooled to room temperature and then SOCl$_2$ (1.5 mL) was added. The mixture was heated to reflux for a further 2 hours and then allowed to cool to room temperature before pouring onto ice under stirring. A precipitate was collected by filtration and washed with cold water. The solid was then added to a solution of NH$_4$OH (150 mL, 10% w/v) and stirred overnight at room temperature. The reaction was acidified to pH 4-5 using concentrated HCl and the resulting solid was collected and dried. The crude product was dissolved with the aid of sonication in EtOAc (100 mL) and then dried over magnesium sulfate and filtered before concentrating to dryness under vacuum to yield the desired product as an off white solid (Formula (XCVI), 360 mg, 5.1%). The 2-chloro-5-(methylsulfonyl)benzenesulfonamide (XCVI) was taken on to the next step without further purification.

In Pathway AD, N-(tert-butylcarbamoyl)-2-chloro-5-(methylsulfonyl) benzene-sulfonamide, Formula (XCVIII) is made from (XCVII).

PATHWAY AD

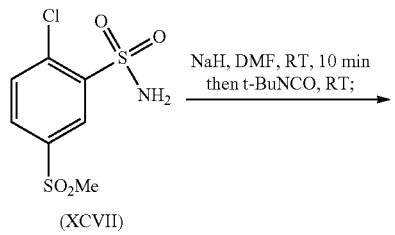
(XCVII)

NaH, DMF, RT, 10 min
then t-BuNCO, RT;

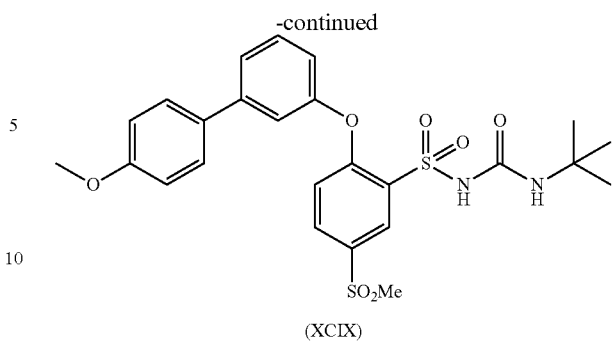
(XCIX)

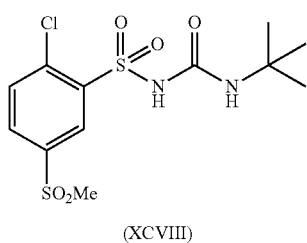
(XCVIII)

Sodium hydride (60% in oil dispersion, 60 mg, 1.46 mmol) was added to a solution of 2-chloro-5-(methylsulfonyl) benzenesulfonamide (33, 360 mg, 1.33 mmol) in DMF (10 mL) at room temperature. The mixture was stirred at room temperature for 15 minutes before tert-butylisocyanate (212 μL, 1.862 mmol) was added. The resulting mixture was stirred overnight at room temperature. The reaction was quenched with water and then the DMF was removed under high vacuum. The residue was diluted with EtOAc and H$_2$O, then acidified using 1 N HCl to pH 1. The product was extracted with EtOAc and the combined organic phases were washed with brine, dried over MgSO$_4$, filtered and evaporated to dryness. The crude product was sonicated for 10 minutes with DCM/MeOH (1:1, 40 mL), then filtered to yield as a white solid (Formula (XCVIII), 0.3 g, 56%) which was used in, e.g., Pathway AE, without further purification.

Pathway AE synthesizes N-(tert-butylcarbamoyl)-2-((4'-methoxy-[1,1'-biphenyl]-3-yl)oxy)-5-(methylsulfonyl) benzenesulfonamide, Formula (XCIX) from (XCVIII).

PATHWAY AE

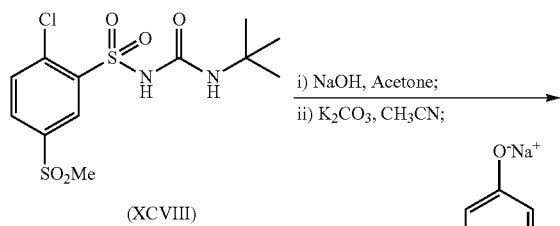
(XCVIII)

i) NaOH, Acetone;
ii) K$_2$CO$_3$, CH$_3$CN;

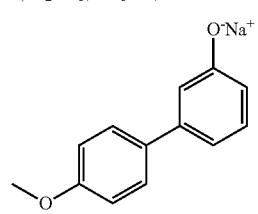

An aqueous solution of NaOH (10% w/v, 80 mg; 2.0 mmol) was added to a solution of the phenol (6, 366 mg; 1.82 mmol) in acetone (10 mL). The solvents were removed under vacuum to afford the sodium salt, which was added to a solution of sulfonamide (34, 135 mg g; 0.367 mmol) in acetonitrile (20 mL). The mixture was heated to reflux and then potassium carbonate (35 mg, 0.257 mmol) was added, maintaining this temperature for 18 hours. The solvents were removed under vacuum and the residue was re-dissolved in DMSO (1.5 mL) and then purified by preparative HPLC to yield an off-white solid (Formula (XCIX), 57 mg, 29%).

The synthesis of modified nitriles is shown.

In Pathway AF, 5-bromo-2-((4'-methoxy-[1,1-biphenyl]-3-yl)oxy)-4-methyl-benzene-sulfonamide, formula (CI), is synthesized from Formula (C).

PATHWAY AF

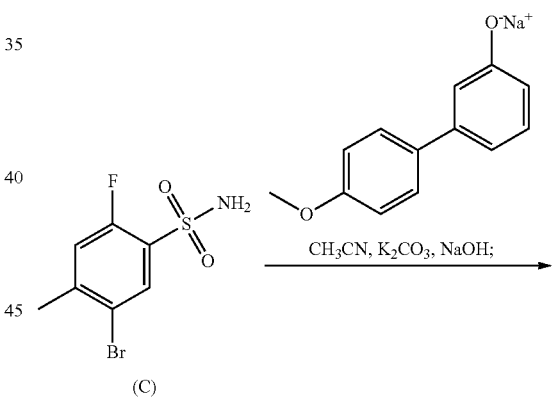
(C)

CH$_3$CN, K$_2$CO$_3$, NaOH;

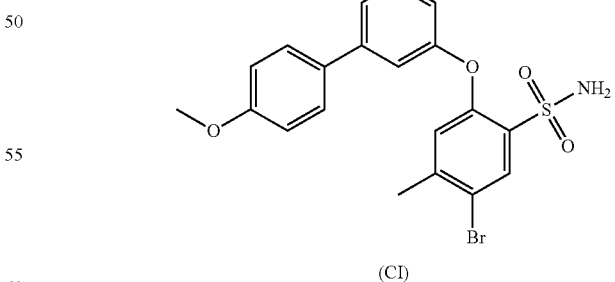
(CI)

A 10% w/v aqueous solution of NaOH (10.23 mmol) was added to a solution of phenol (1.12 g, 5.58 mmol) in acetone (50 mL). The reaction was evaporated under reduced pressure to afford the sodium salt. The 5-bromo-2 fluoro-4-methylbenzene sulfonamide (Formula (C), 0.5 g, 1.86 mmol) was dissolved in acetonitrile (20 mL) and added to the sodium salt, dissolved in acetonitrile (30 mL). The resulting reaction mixture was heated to reflux. Potassium carbonate (180 mg, 1.302 mmol) was added after 30 minutes and the reaction left to reflux for 18 hours, after which time LC-MS analysis showed starting material only. The reaction mixture was then heated in the microwave for 4 hours at 140° C., after which time LC-MS analysis showed approximately 25% conversion. The acetonitrile was removed under reduced pressure and the residue was taken up in ethyl acetate/$H_2O$. The aqueous layer was acidified using concentrated HCl (pH=1) and the organics were separated and the aqueous re-extracted with ethyl acetate (×2). The combined organics were dried and evaporated to give a brown oil (~2 g). The oil was re-dissolved in DCM and loaded onto 100 g Biotage silica cartridge and purified by Biotage chromatography (eluting with iso-hexane/ethyl acetate, gradient 20-80%). The fractions containing product were combined and evaporated to give an orange oil (~0.6 g). LC-MS analysis showed 77.4% purity, and therefore, the oil was re-purified by loading onto 50 g Biotage silica cartridge and purified by Biotage chromatography (eluting with iso-hexane/ethyl acetate, gradient 0-50%) and dried to give the final product (Formula (CI), 361 mg).

In Pathway AG, 5-cyano-2-((4'-methoxy-[1,1'-biphenyl]-3-yl)oxy)-4-methylbenzenesulfonamide, Formula (CII), is prepared.

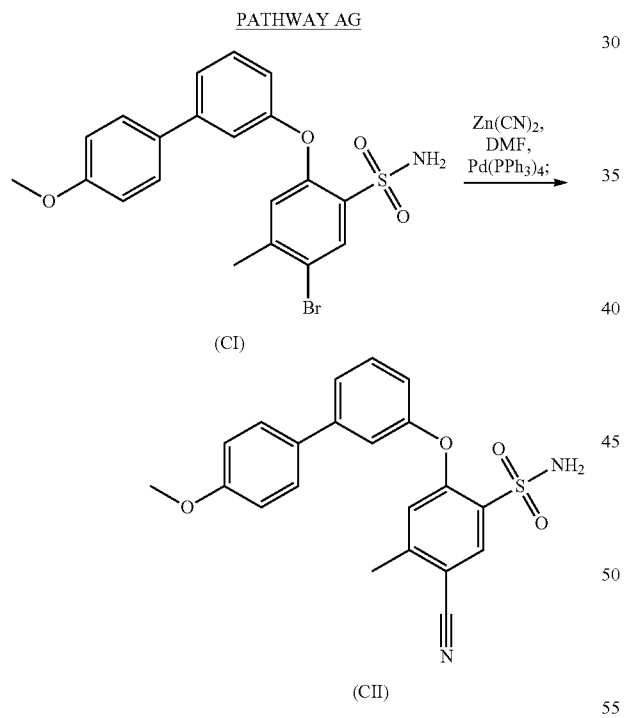

The sulfonamide (Formula (CI), 480 mg, 1.071 mmol) was dissolved in DMF (4 mL) and $Zn(CN)_2$ (189 mg, 1.606 mmol) was added. The reaction mixture was flushed with nitrogen before the addition of $Pd(PPh_3)_4$ (124 mg, 0.107 mmol). The vial was sealed and heated to 80° C. for 72 hours. The solid was filtered off and the DMF removed under high vacuum. The resulting crude solid was taken up in DCM and $H_2O$ and the organics separated, dried and evaporated to give a pale yellow oil (~550 mg). The oil was dissolved in DCM and loaded onto 50 g Biotage silica cartridge and purified using Biotage chromatography (eluting with iso-hexane/ethyl acetate, gradient 20-75%) and the product containing fractions were concentrated to dryness under vacuum to give an off white solid (Formula (CII), 175 mg, 41.4%).

Pathway AH produces N-(tert-butylcarbamoyl)-5-cyano-2-((4'-methoxy-[1,1'-biphenyl]-3-yl)oxy)-4-methyl benzenesulfonamide, Formula (LVIII), from (CII).

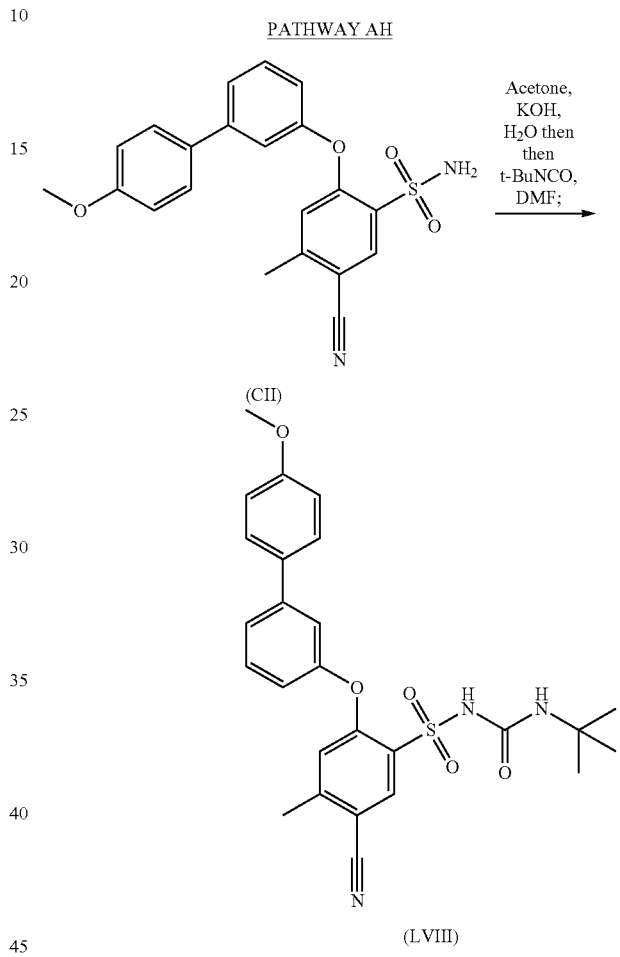

A solution of the sulfonamide (Formula (CII), 175 mg, 0.444 mmol) in acetone (2 mL) was treated with a solution of KOH (24.9 mg, 0.444 mmol) in H2O (100 μL). The reaction was stirred at room temperature for 30 minutes. The solvent was removed under high vacuum and the resulting residue was dissolved in DMF (2 mL). tert-Butylisocyanate (101 μL, 0.888 mmol) was added and the reaction was stirred for 18 hours at room temperature. The reaction mixture was evaporated to dryness under high vacuum and the residue re-dissolved in mixture of MeOH and DCM and loaded on to silica. The crude product was purified by Biotage chromatography on a 50 g Biotage Silica cartridge (elution with iso-hexane/ethyl acetate, gradient 0-75%), then triturated with diethyl ether/iso-hexane and dried under vacuum to give as a white solid (Formula (LVIII), 131 mg, 60%).

In Pathway AI, 5-bromo-2-((4'-methoxy-[1,1'-biphenyl]-3-yl)oxy)pyridine-3-sulfonamide, Formula (CIV), is made.

PATHWAY AI

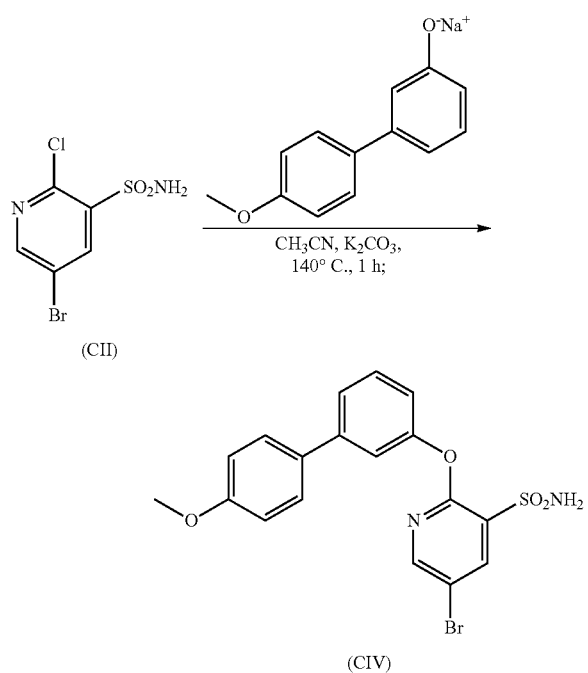

A solution of 5-bromo-2-chloropyridine-3-sulfonamide (Formula (CIII), 1 g, 3.63 mmol) and the methoxy biphenol (1.45 g, 7.26 mmol) in acetonitrile (40 mL) was heated at reflux overnight in the presence of K$_2$CO$_3$ (1.03 g, 7.260 mmol). LC-MS showed ~40% conversion. The reaction mixture was then heated to 140° C. for 1 hour, after which time LC-MS showed complete conversion. The solvents were removed under vacuum and the residue was diluted with water, and then extracted with DCM (50 mL). The organic phases were combined, dried over MgSO$_4$ and then concentrated to dryness directly onto silica. The crude product was purified by Biotage chromatography using a 100 g Biotage silica cartridge (eluting with iso-hexane/ EtOAc, gradient 0 to 50%) and the product containing fractions were concentrated to dryness under vacuum to give as a white solid (Formula (CIV), 0.92 g, 58%) which was used directly in the next step without further purification.

Using Pathway AJ, (CV) as a reactant yields 5-cyano-2-((4'-methoxy-[1,1'-biphenyl]-3-yl)oxy)pyridine-3-sulfonamide, Formula (CVI).

PATHWAY AJ

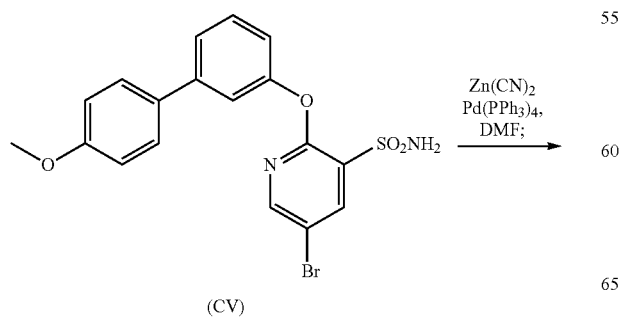

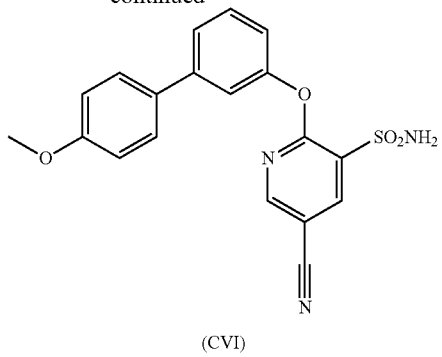

The pyridine sulfonamide (Formula (CV), 250 mg, 0.575 mmol), Zn(CN)$_2$ (101 mg, 0.862 mmol), Pd(PPh$_3$)$_4$ (66 mg, 0.0575 mmol) and DMF (3 mL) were charged to a stem tube. The mixture was de-oxygenated by purging with nitrogen and then sealed under nitrogen. The reaction was heated to 80° C. for 72 hours. The solvents were removed under vacuum, loading directly onto silica before purification by Biotage chromatography (50 g cartridge, eluting with DCM/ MeOH gradient 0-5%). The product containing fractions were concentrated to dryness under vacuum to give a solid that was triturated with diethyl ether (4 mL), filtered and then dried to provide as a white powder (Formula (CVI), 160 mg, 73%).

To prepare N-(tert-butylcarbamoyl)-5-cyano-2-((4'-methoxy-[1,1'-biphenyl]-3-yl)oxy)benzene-sulfonamide, Formula (LIX), from (CVI), Pathway AK is used.

PATHWAY AK

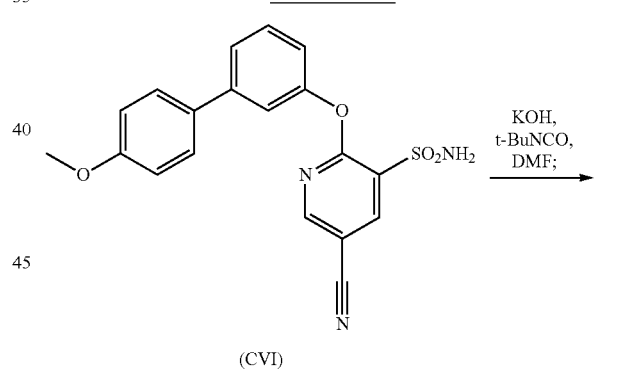

KOH (33 mg, 0.5879 mmol) in water (0.4 mL) was added to a solution of the pyridine sulphonamide (Formula (CVI), 160 mg, 0.412 mmol) in acetone (8 mL). The mixture was stirred for 2 minutes and then concentrated to dryness under vacuum. The residue was dissolved in DMF (1 mL) before the addition of tert-butylisocyanate (96 μL, 0.840 mmol) and stirred for 3 hours. The reaction was concentrated to dryness. The crude product was re-dissolved in a mixture of DCM/MeOH and then loaded onto silica. The crude product was purified by Biotage chromatography (50 g cartridge, eluting with DCM/MeOH, gradient 0-5%). The product fractions were combined and concentrated to dryness to give as an off-white solid (Formula (LIX), 149 mg, 74%).

Synthesis of a pyridyl compound is described.

In Pathway AL, 4-((4'-methoxy-[1,1'-biphenyl]-3-yl)oxy)pyridine-3-sulfonamide, formula (CVIII) is made.

Pathway AM shows the preparation of N-(tert-butylcarbamoyl)-4-((4'-methoxy-[1,1'-biphenyl]-3-yl)oxy)pyridine-3-sulfonamide, represented by formula (LVII).

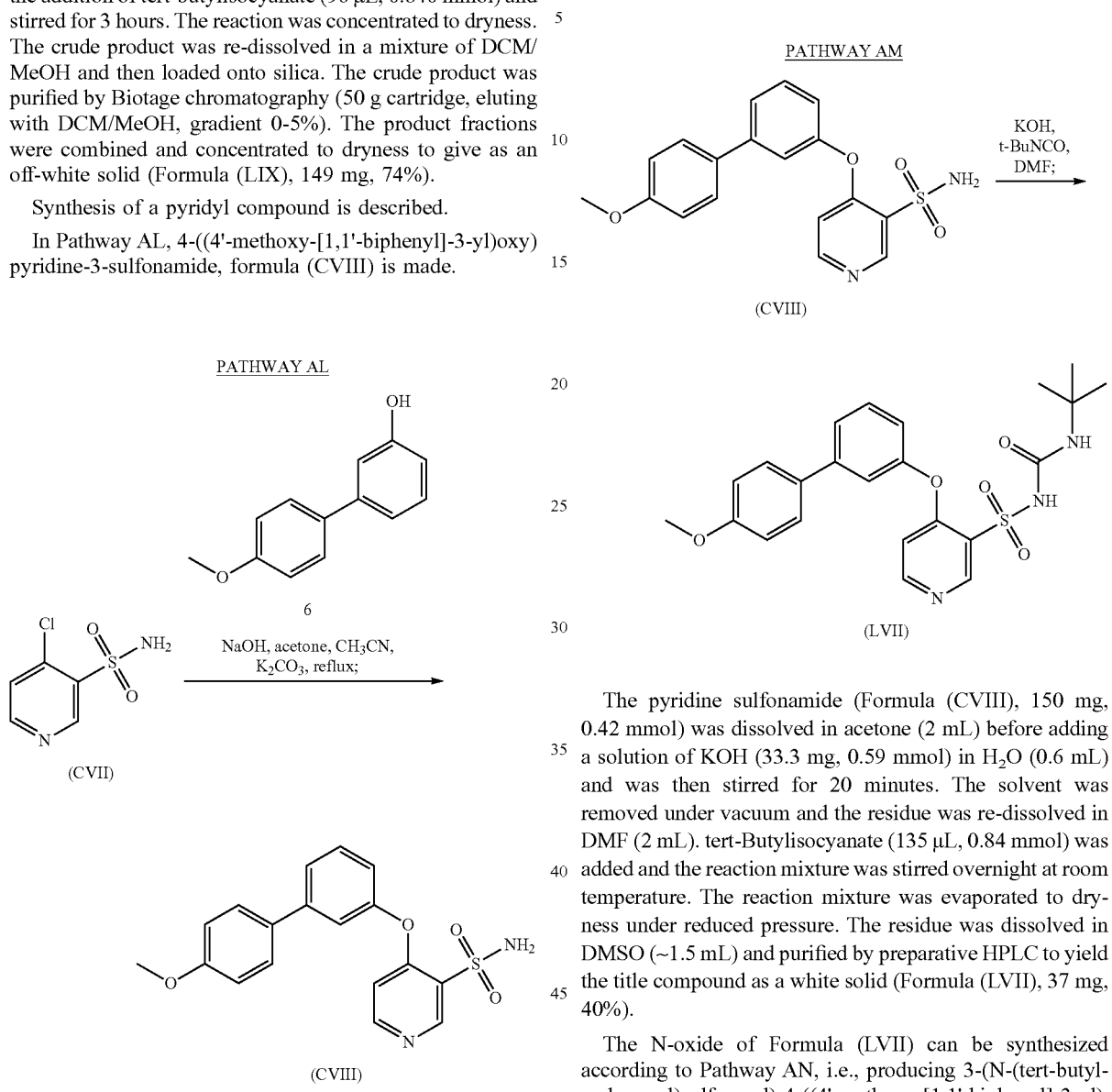

For pathway AL, an aqueous solution of NaOH (330 mg, 8.25 mmol, 10% w/v,) was added to a solution of the 4'-methoxy-[1,1'-biphenyl]-3-ol (1.5 g, 7.5 mmol) in acetone (45 mL). The solvents were removed by evaporation to afford the sodium salt which was added to a solution of the 4-chloropyridine-3-sulfonamide (Formula (CVII), 723 mg, 1.5 mmol) in MeCN (45 mL). The reaction mixture was heated under reflux for 1 hour. The reaction was cooled, K₂CO₃ (364 mg, 2.63 mmol) was added and the reaction heated to reflux for 72 hours. A solid product was obtained when DCM (50 mL) and H₂O (30 mL) were added. The crude product was collected by filtration, washed with aqueous 10% K₂CO₃ (4×10 mL) to yield the target compound (Formula (CVIII)) which may be taken through to Pathway AM without further purification.

The pyridine sulfonamide (Formula (CVIII), 150 mg, 0.42 mmol) was dissolved in acetone (2 mL) before adding a solution of KOH (33.3 mg, 0.59 mmol) in H₂O (0.6 mL) and was then stirred for 20 minutes. The solvent was removed under vacuum and the residue was re-dissolved in DMF (2 mL). tert-Butylisocyanate (135 μL, 0.84 mmol) was added and the reaction mixture was stirred overnight at room temperature. The reaction mixture was evaporated to dryness under reduced pressure. The residue was dissolved in DMSO (~1.5 mL) and purified by preparative HPLC to yield the title compound as a white solid (Formula (LVII), 37 mg, 40%).

The N-oxide of Formula (LVII) can be synthesized according to Pathway AN, i.e., producing 3-(N-(tert-butylcarbamoyl)sulfamoyl)-4-((4'-methoxy-[1,1'-biphenyl]-3-yl)oxy)pyridine 1-oxide, Formula (LX).

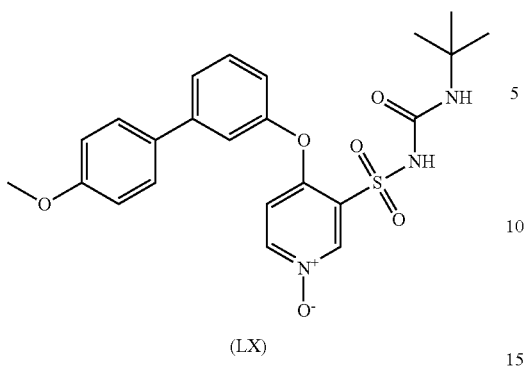
(LX)

In Pathway AN, tert-butylperoxide (12 μL, 0.0594 mmol) was added to a solution of pyridyl (Formula (LVII), 16 mg, 0.0396 mmol) in DCM (1 mL) and the reaction was stirred for 18 hours. LC-MS analysis showed no conversion. A further aliquot of tert-butylperoxide (24 μL, 0.119 mmol) was added and after a further 4 hours of stirring there was still no reaction, as confirmed by LC-MS. m-CPBA (15 mg, 0.0869 mmol) was added and the reaction was stirred for 18 hours. LC-MS analysis confirmed complete conversion to the desired product. The solvents were removed under vacuum and the crude product was re-dissolved in DMF (1.5 mL) and then purified by preparative HPLC to give the desired product (Formula LX, 6.8 mg, 36%).

The foregoing pathways are illustrative of possible ways to prepare compounds of the invention and are not limiting. Using pathways such as those described above, compounds of the invention can be synthesized, such as those described by the formulas (LII), (LXXV), (XCI), (LXII), (LXXIV), (LXIII), (LXI), (XCIV), (LXX), (LXXVI), (LXXXV), (LXXXVII), (LXXVIII), (LXXX), (LXXXI), (LXXXII), (LXXXIII), (LXIV), (LXV), (LXVI), (LXVII), (LXXIX), (LXXXVIII), (LXXXVI), (LXXXIV), (CIX), (XCIX), (LXXVII), (LXVIII), (CX), (LVII), (LVIII), (LIX), and (LX).

(LII)

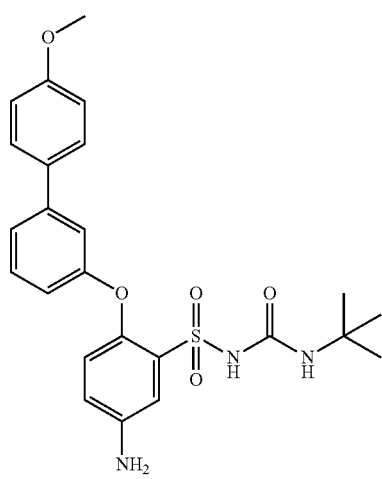

Mw - 469.56

(LXXV)

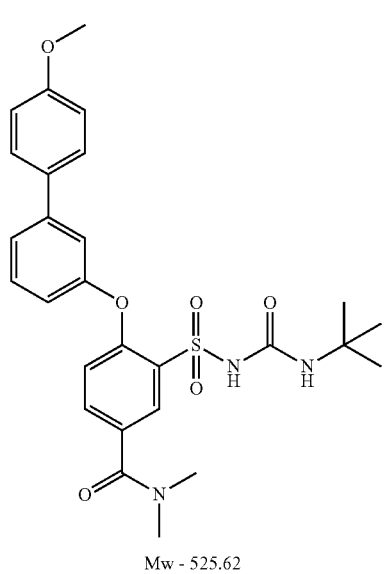

Mw - 525.62

(XCI)

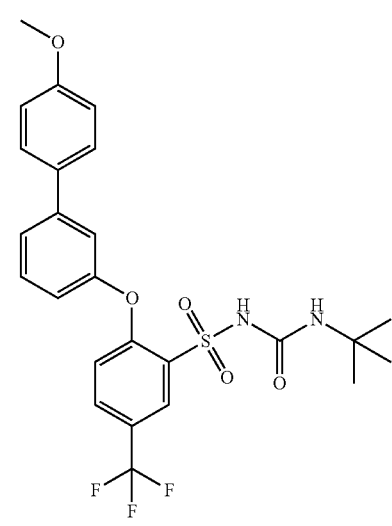

Mw - 522.54

(LXII)

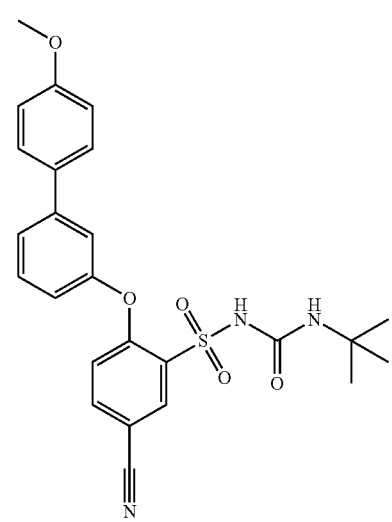

Mw - 479.55

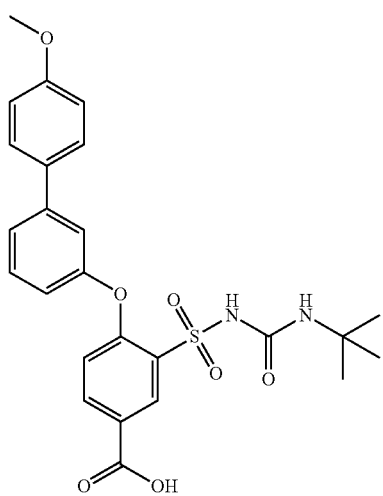
(LXXIV)
Mw: 498.55
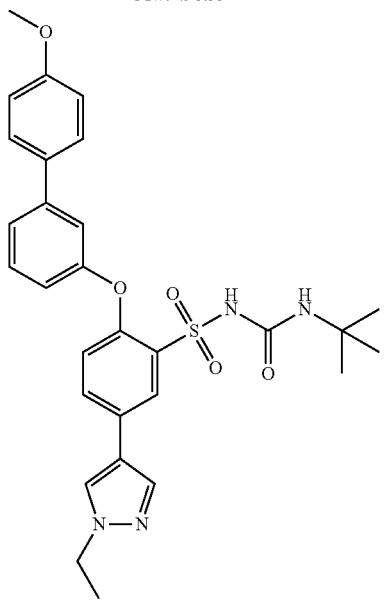
Mw: 548.66
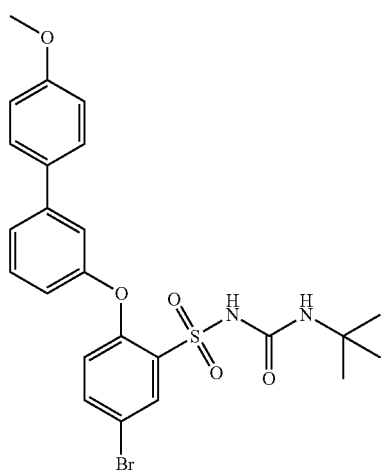
Mw: 533.45
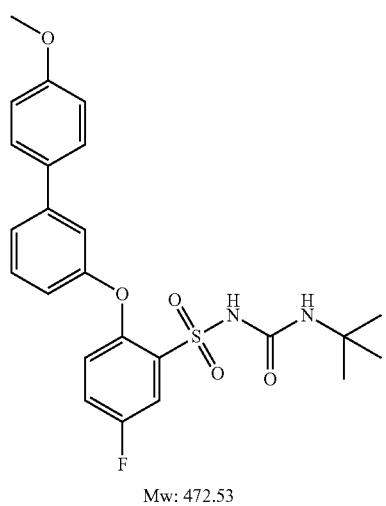
(XCIV)
Mw: 472.53
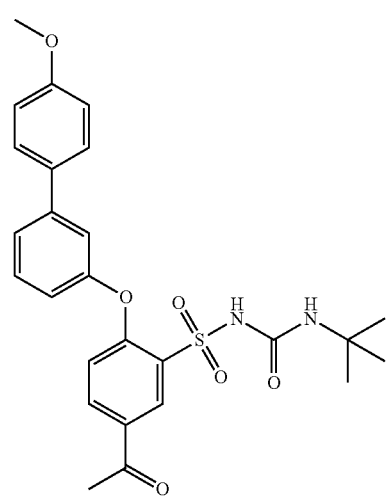
(LXX)
Mw: 496.58
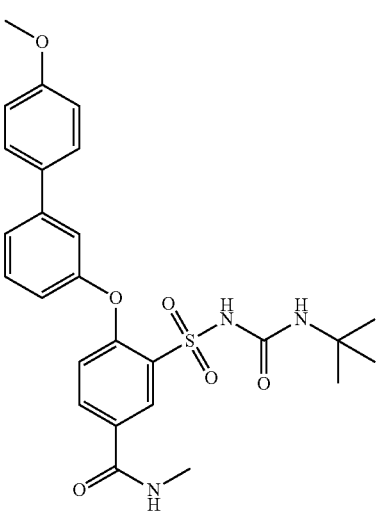
(LXXVI)
Mw: 511.60

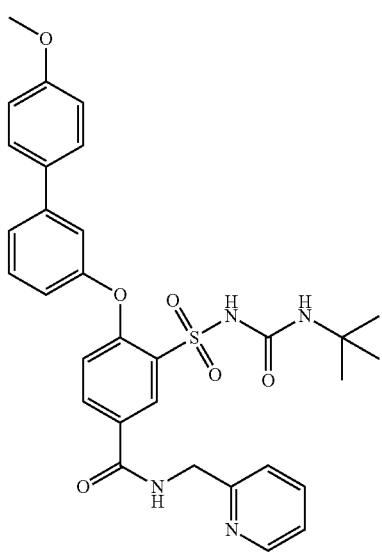
(LXXXV)
Mw: 588.68
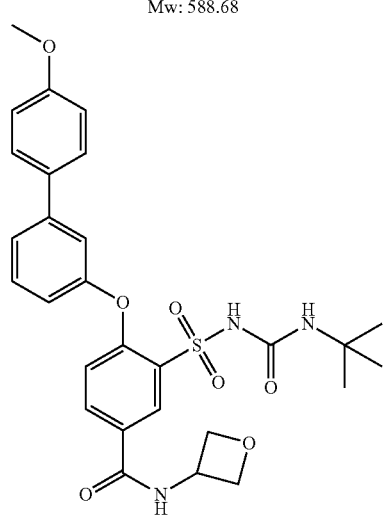
(LXXXVII)
Mw: 553.63
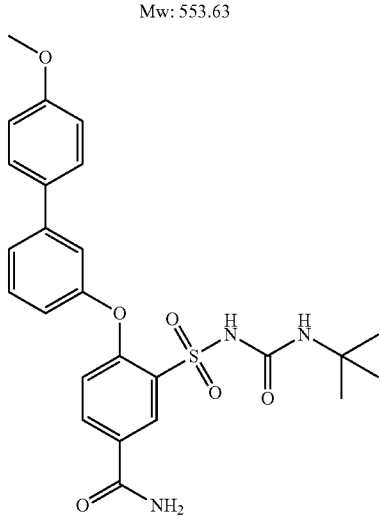
(LXXVIII)
Mw: 497.57
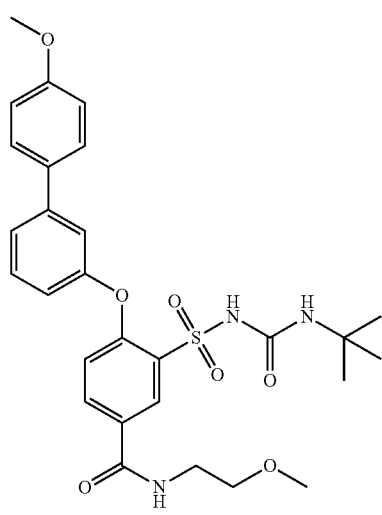
(LXXX)
Mw: 555.65
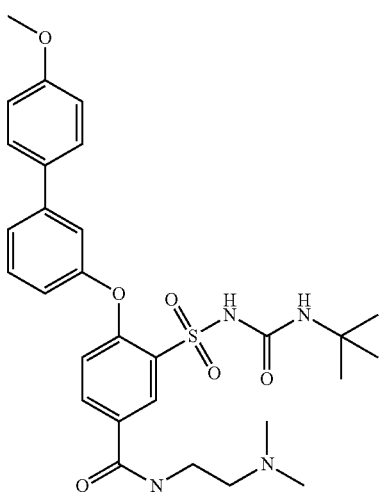
(LXXXI)
Mw: 568.69
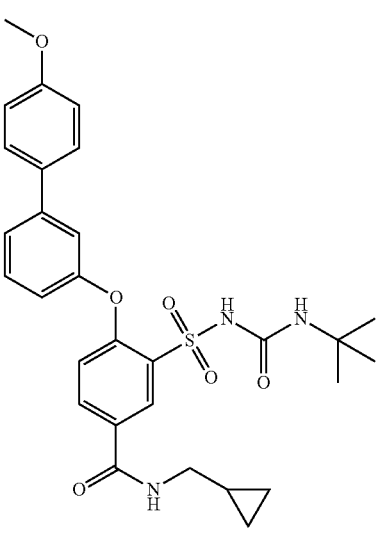
(LXXXII)
Mw: 551.66

91 92
-continued -continued
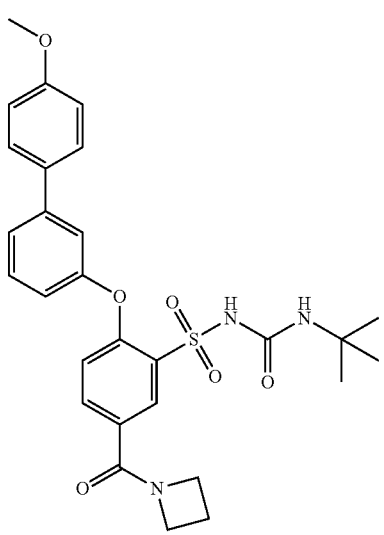
(LXXXIII)
Mw: 537.63
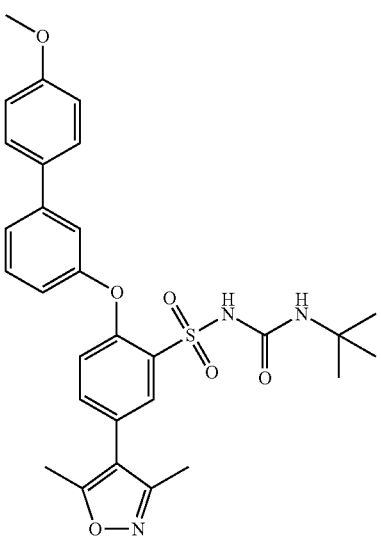
(LXV)
Mw: 549.65
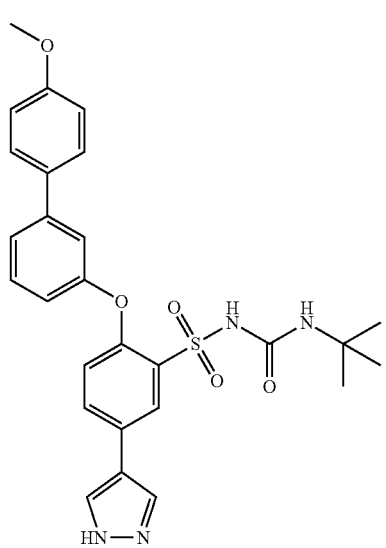
(LXIV)
Mw: 520.61
(566.61, as formate salt)
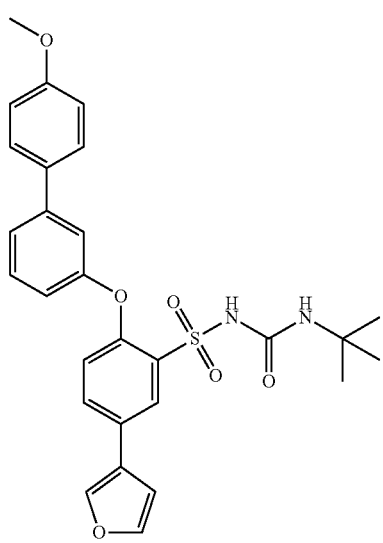
(LXVI)
Mw: 520.60

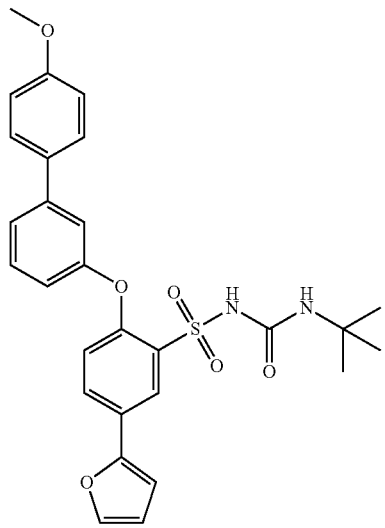
(LXVII)
Mw: 520.60
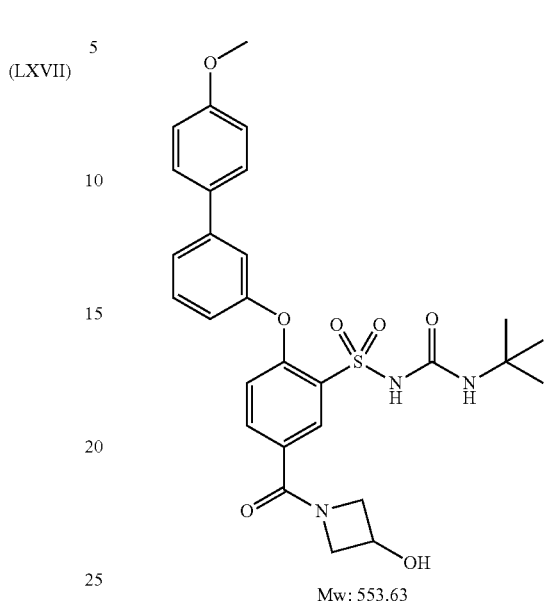
(LXXXVIII)
Mw: 553.63
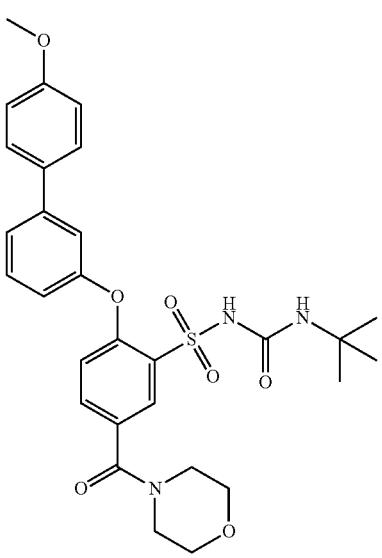
(LXXIX)
Mw: 567.66
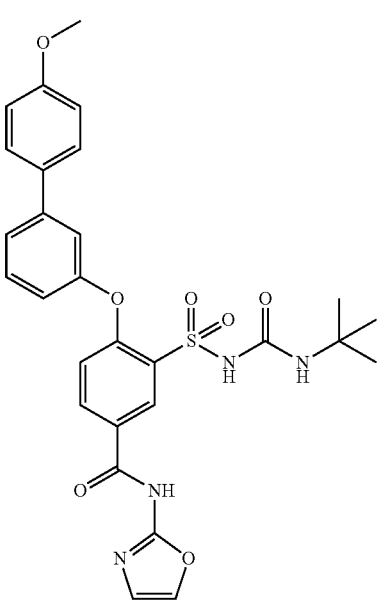
(LXXXVI)
Mw: 564.62

(LXXXIV)
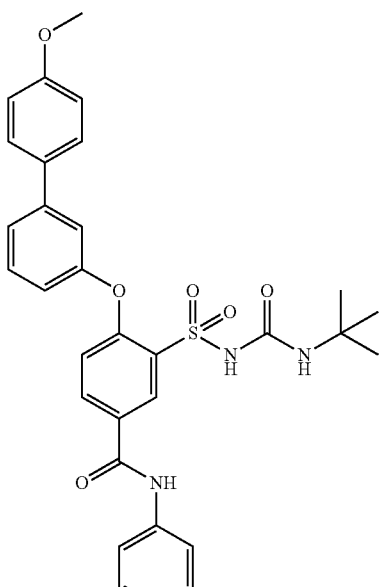
Mw: 573.67
(XCIX)
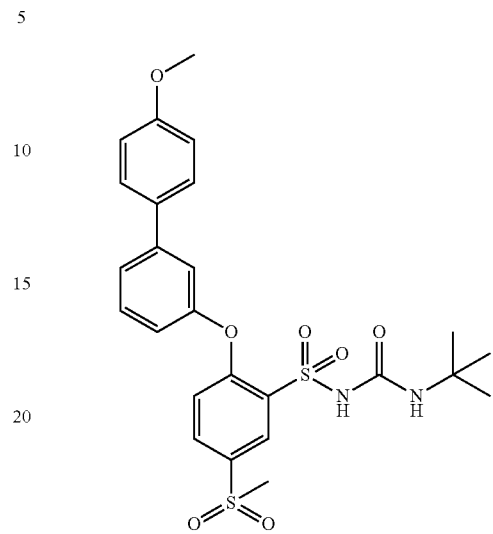
Mw: 532.63
(CIX)
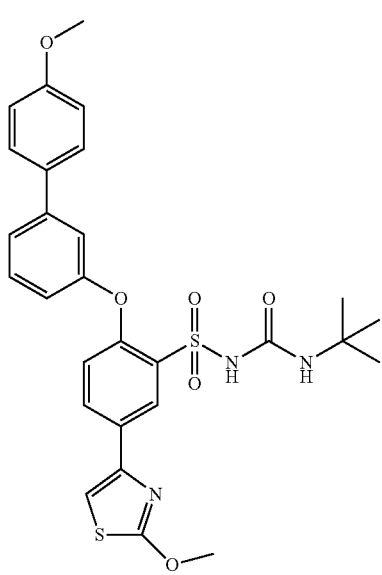
Mw: 567.68
(LXXVII)
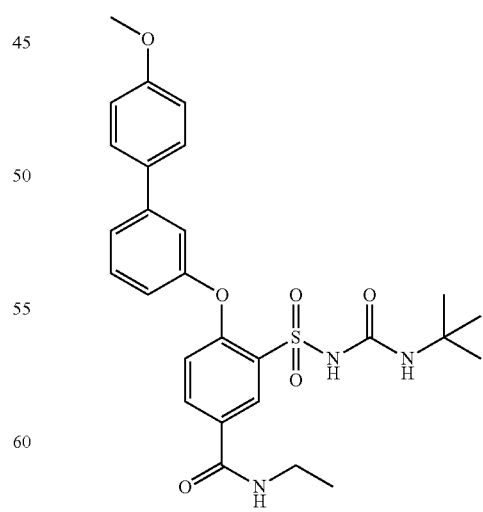
Mw: 525.62

(LXVIII)
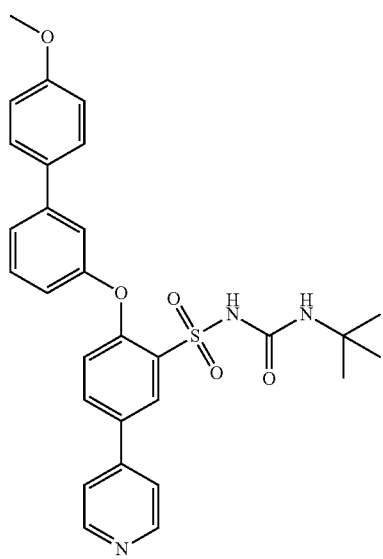
Mw: 531.63
(CX)
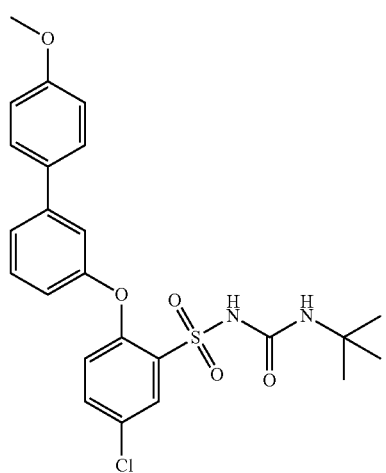
Mw: 488.99
(LVII)
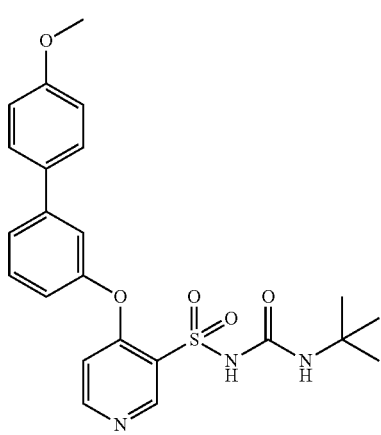
Mw: 493.58
(LVIII)
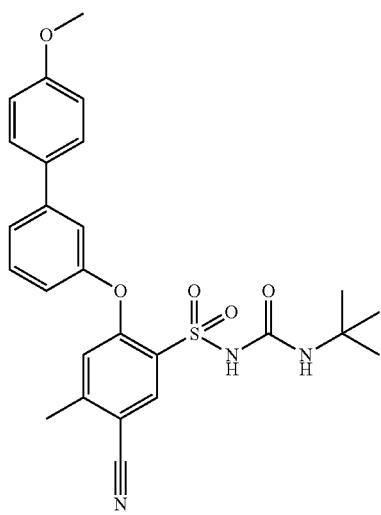
Mw: 480.54
(LIX)
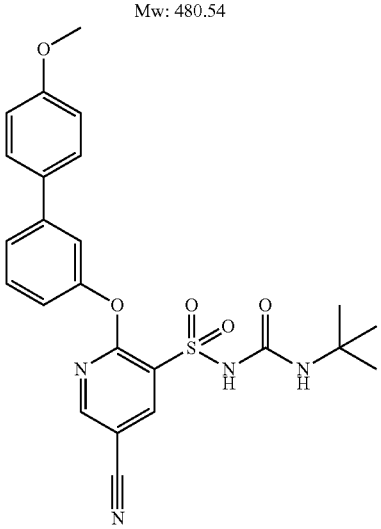
Mw: 479.55
(LX)
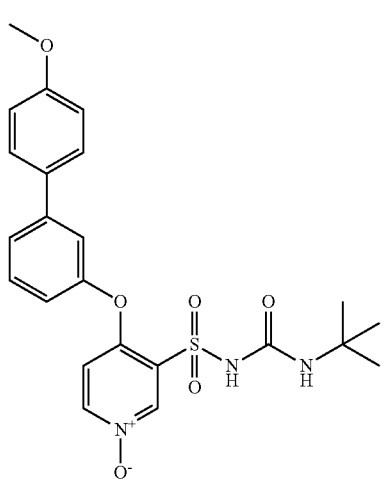
Mw: 471.53

Compounds of the invention can be in a pharmaceutically acceptable salt form or as the free base. Suitable routes of administration include oral, buccal, topical (including transdermal), injection, intravenous, nasal, pulmonary, and with or on an implantable medical device (e.g., stent or drug-eluting stent or balloon equivalents).

The effective dosage of each agent can readily be determined by a skilled person, having regard to typical factors such as the age, weight, sex and clinical history of the patient. A typical dosage could be, for example, 1-1,000 mg/kg, preferably 5-500 mg/kg per day, or less than about 5 mg/kg, for example administered once per day, every other day, every few days, once a week, once every two weeks, or once a month, or a limited number of times, such as just once, twice or three or more times.

A pharmaceutical composition containing each active ingredient may be in a form suitable for oral use, for example, as tablets, troches, lozenges, fast-melts, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration in the stomach and absorption lower down in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452 and 4,265,874, to form osmotic therapeutic tablets for control release. Preparation and administration of compounds is discussed in U.S. Pat. No. 6,214,841 and U.S. Pub. 2003/0232877, incorporate by reference herein in their entirety.

Formulations for oral use may also be presented as hard gelatin capsules in which the active ingredient is mixed with an inert solid diluent, for example calcium carbonate, calcium phosphate or kaolin, or as soft gelatin capsules in which the active ingredient is mixed with water or an oil medium, for example peanut oil, liquid paraffin or olive oil.

An alternative oral formulation, where control of gastrointestinal tract hydrolysis of the compound is sought, can be achieved using a controlled-release formulation, where a compound of the invention is encapsulated in an enteric coating.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Each active agent, including the inventive compound, may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Examples of such materials are cocoa butter and polyethylene glycols.

For topical use, creams, ointments, jellies, fast melt tablets, solutions or suspensions are suitable as are nebulized forms for pulmonary delivery. Topical application includes the use of mouth washes and gargles.

The invention further also generally relates to devices such as implantable medical devices including an antithrombotic compound. In certain aspects, the invention provides a stent (e.g., a drug-eluting stent) or balloon comprising a compound of the invention or a compound of the invention along with other complementary drugs such as sirolimus, paclitaxel, tPA, urokinase etc. A device of the invention may be a drug-eluting aortic valve prosthesis or a drug-eluting mitral valve prosthesis. Accordingly, the invention provides administration of a compound of the invention via delivery from a stent, aortic valve, or mitral valve. In some embodiments, the invention provides a drug-eluting aortic valve or drug-eluting mitral valve.

In certain embodiments, the invention provides an implantable medical device or balloon comprising a compound of the invention for use in percutaneous cardiovascular intervention (PCI). A device of the invention can be a stent or a balloon. The invention also provides methods of using devices comprising antithrombotic compounds. Devices and methods of the invention can provide a TP antagonist compound in a stent (e.g., DES), balloon, implantable device, or surgical device or a compound of the invention along with other complementary drugs such as tPA, urokinase etc. In a preferred embodiment, the compound has formula (X). Devices and antithrombotic compounds are discussed in U.S. Pat. No. 7,947,302; U.S. Pat. No. 7,618,949; and U.S. Pub. 2006/0122143, the contents of which are hereby incorporated by reference in their entirety.

A stent according to the invention can comprise a mesh tube-like structure, for example, to be used in conjunction with angioplasty to permanently hold open an artery at the narrowed site in the blood vessel, allowing for unrestricted blood flow, or to support a weakness or "aneurysm" in the blood vessel artery wall. Stents are discussed in U.S. Pat. No. 6,796,998; U.S. Pat. No. 6,352,552; U.S. Pub. 2005/0015136; U.S. Pub. 2005/0010279; and U.S. Pub. 2007/0168015, the contents of each of which are herein incorporated by reference in their entirety.

Compounds of the invention, such as the compound having formula (X), provide coating agents for stents, drug-eluting stents (DESs), bifurcation stents, by-pass graft vessel stents, balloons, medical devices, or surgical devices used, for example, to treat stroke or other thrombotic events. By antagonizing the TP receptor on platelets and macrophages, these compounds will prevent platelet aggregation and secretion at sites of local vessel damage and counteract the inflammatory effects of elevated levels of $TXA_2$ at sites of local vessel damage. By antagonizing the TP on smooth muscle cells (SMCs), the compounds will prevent $TXA_2$-induced SMC proliferation, neo-intima thickening and restenosis. Furthermore, as the TP also mediates the adverse actions of the isoprostane 8-iso-prostaglandin $(PG)F_{2\alpha}$, generated in abundance from arachidonic acid non-enzymatically from free radicals in situations of oxidative stress/injury, including in ischemia, compounds of the invention may also inhibit the undesirable actions of 8-iso-$PGF_{2\alpha}$ within the damaged blood vessel. The combination of these compounds with very low levels of sirolimus and/or paclitaxel may be synergistic in further preventing restenosis while at the same time in eliminating/reducing the adverse effects associated with local, high levels of sirolimus or paxlitaxol. The combination of these compounds along with clot lysing drugs such as tPA, urokinase or related type of drug can both lyse clots at sites of occlusion and prevent new thrombus formation, such as in the treatment of atherothrombosis, ischemic or cerebral stroke etc. DESs are discussed in U.S. Pat. No. 7,135,038; U.S. Pat. No. 5,697,967; U.S. Pub. 2011/0099785; U.S. Pub. 2010/0023115; and U.S. Pub. 2005/0043788, the contents of each of which is herein incorporated by reference in their entirety. Coating of stents is discussed in U.S. Pat. No. 7,833,544 and U.S. Pub. 2009/0062904, the contents of which are herein incorporated by reference in their entirety.

In certain embodiments, the invention provides TP antagonists with novel applications as a coating or a component of a device either used alone or in combination with very low levels of sirolimus and/or paxlitaxol. The release profile and timing of the release profile of both the compound of the invention (e.g., formula (X)) along with either sirolimus and/or paxlitaxol can be optimized to maximize the anti-thrombotic and anti-restenosis effects. This can result in the prevention of signaling by the elevated levels of $TXA_2$, and of the isoprostane 8-iso-$PGF_{2\alpha}$, found in vicinity of damaged blood vessels post angioplasty and stenting. Prevention of this signaling prevents or reduces the impairment of the host immune response which arise due to elevated levels of $TXA_2$, and the isoprostane 8-iso-$PGF_{2\alpha}$, in the vicinity of damaged blood vessels post angioplasty and stenting. Compounds of the invention may further prevent restenosis, for example, by antagonizing TP on smooth muscle cells. Compounds of the invention could also be coated onto aortic or mitral valves which are used in TAVI (trans-catheter aortic valve intervention) to treat aortic stenosis. Such coating with the compounds onto aortic or mitral valves may prevent thrombus or stroke occurrence after TAVI surgery.

The invention provide compounds which can be used as a coating on bare metal stents, interwoven stents, drug-eluting stents and balloons, bifurcation stents and by-pass graft stents, namely for use as: (a) an anti-restenosis agent, (b) an anti-thrombotic agent and (c) a pro re-endothelialization agent. Compounds of the invention would be released from such coated medical devices used in the treatment of various diseases of the vasculature including coronary arterial disease (CAD) and peripheral arterial disease (PAD) in a pre-defined manner including zero order release, first order release and/or a combination of initial burst release followed by controlled release over a defined time period (e.g., 12 months). Compounds of the invention may be particularly beneficial in Aspirin resistant patients (~30% of the general population) who are even more vulnerable to acute coronary stent thrombosis and who develop elevated levels of prostanoids such as $TXA_2$ post stenting (Ruef & Kranzhofer, 2006, J Inter. Cardiol. Vol 19, pages 507-509). Other applications of the new small molecule drug as a coating on medical devices include applications on (a) bifurcation stents or by-pass graft lesion stents, (b) clot dissolvers on medical devices used to treat stroke and further prevention of clot formation on medical devices for neurological applications, (c) as well as a coating on inferior vena cava filters (IVCFs) used to treat severe deep vein thrombosis (DVT) or pulmonary embolism (PE) in various types of patients including those subject to various surgical interventions such as bariatric surgery, orthopedic surgery, trauma patients and diabetic patients undergoing surgical intervention. Drug delivery from devices is discussed in U.S. Pat. No. 7,713,538; U.S. Pub. 2004/0213818 and U.S. Pub. 2009/0311299, incorporated by reference herein in their entirety.

As various compounds of the invention do not require liver metabolism to achieve an active therapeutic form, they provide the benefit of immediate therapeutic effect within the vasculature at the site of release or immediate local environment of the coated medical device. This drug coating on medical devices has applications as prophylaxis and/or as therapeutic treatment.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

Examples

Example 1: Calcium Mobilization

The appropriate functional test for the evaluation of the agonistic and/or antagonistic potency of the compounds of the invention is the determination of calcium flux. Both TPα and TPβ are coupled to the G-protein Gαq. Therefore, stimulation of these receptors ultimately leads to a release of intracellular calcium ($[Ca^{2+}]_i$) from intracellular stores. Consequently, the determination of $[Ca^{2+}]_i$ flux represents an appropriate functional test for the evaluation of the agonistic/antagonistic potency of compounds of the invention. Calcium can be measured using a molecule characterized by the covalent combination of a $Ca^{2+}$ chelating group and a fluorophore group. The $Ca^{2+}$ binding properties of these indicators are formed by the presence of a tetracarboxylic acid core as found for example in EGTA (ethylene glycol bis(2-aminoethyl) tetraacetic acid). Binding of $Ca^{2+}$ produces a wavelength shift in either the excitation or emission fluorescence spectra or a change in the emission intensity. Whereas the $Ca^{2+}$ binding to EGTA is pH dependent, recent dyes are designed from an EGTA derivative, BAPTA (1, 2-Bis(2-Aminophenoxy)ethane-N, N, N', N'-Tetraacetic Acid). Loading of these dyes inside cells commonly uses esterified forms (acetoxymethyl ester), which are able to cross the cell membranes and are subsequently hydrolyzed by esterases inside the cell.

Estimation of $[Ca^{2+}]_i$ flux is calculated from the fluorescence signal (F). For calibration, the maximal fluorescence ($F_{max}$, $Ca^{2+}$-saturated form of the dye) as well as minimal fluorescence ($F_{min}$, $Ca^{2+}$-free form of the dye) must be determined. These parameters are determined usually in situ after the experiment, for example by subsequent addition to the mixture of a cell-disrupting agent that releases all $Ca^{2+}$ such as Triton X100 and a potent $Ca^{2+}$-chelating agent such as EGTA. After subtraction of background fluorescence, $[Ca^{2+}]_i$ flux can be calculated for non-ratiometric indicators.

Intracellular $[Ca^{2+}]_i$ fluxes were measured using a fluorescence plate reader following a modified protocol of Kassack et al., Quantitative comparison of functional screening by measuring intracellular $Ca^{2+}$ with radioligand binding at recombinant human dopamine receptors. AAPS Pharmsci, 2002, 4(4); 102-111, in cell lines (e.g. HEK293 or other cell type) endogenously-expressing or over-expressing either TPα, TPβ or any other receptor or protein to be screened.

By way of example, HEK 293 cells which have been grown for 3-4 days in normal growth media (minimum essential media containing 10% FBS and 2 mmol/l L-glutamine), under normal growth conditions (37° C., in humidified 5% $CO_2$ atmosphere) are washed and harvested in KREBs-HEPES buffer (118 mM NaCl, 4.7 mM KCl, 1.2 mM $MgSO_4$, 1.2 mM $KH_2PO_4$, 4.2 mM $NaHCO_3$, 11.7 mM D-glucose, 1.3 mM $CaCl_2$, 10 mM HEPES, pH 7.4). Cells are then incubated with 3 M Fluo-4 in KREBs-HEPES buffer containing 1% Pluoronic F-127, for 1 hr at 25° C. with agitation. Thereafter, cells are washed in KREBs-HEPES buffer containing 0.5% bovine serum albumin and resuspended at a final concentration of $3×10^5$ cells/ml. Approximately, $5.4×10^4$ cells per well are plated in a 96-well plate and pre-incubated with test compounds for 10 min prior to measuring the fluorescence intensity at 520 nm for 25 seconds at 1 second intervals to monitor baseline using the Fluoroskan Ascent. Agonist (e.g., 1 μM U46619) is injected into separate wells by the automatic pipettor and fluorescence intensity is monitored at 520 nm for 75 seconds at 1 second intervals. Thereafter, Triton X100 and EGTA are added sequentially where $F_{max}$ refers to maximal fluorescence intensity measured after permeabilization of the cells with 2% Triton X100 and $F_{min}$ refers to fluorescence intensity measured after addition of 1 mM EGTA. Changes in mobilization of intracellular $[Ca^{2+}]$ concentration are calculated as follows:

$$\Delta[Ca^{2+}]_i(nM) = Kd \times (F-F_{min})/(F_{max}-F)$$

where an equilibrium constant (Kd) of 345 nM is used for Fluo-4.

The dye Fluo-4 has its excitation peak at 480 nm, in the visible spectra, which spare cells to be damaged by UV (340-360 nm) stimulation and reduces auto-fluorescence of cells. It is not necessary to determine the precise $[Ca^{2+}]_i$, but rather variations in concentrations.

The method allows the detection of $[Ca^{2+}]_i$ mobilization upon stimulation by U46619 in human TP platelets. Similarly, the $[Ca^{2+}]_i$ mobilization in response to U46619 stimulation (1 M) in the HEK293 cell lines is assessed. Both TPα and TPβ transfected cells responded in a comparable fashion. The $[Ca^{2+}]_i$ mobilization in response to other agonists in HEK 293 and other cell types either endogenously-expressing or over-expressing other receptors or proteins is assessed.

As reference compounds for screening assays, compounds 9h and 9ag, previously described by Dogne and Hanson et al., (Hanson, J. S., S. Rolin, et al. (2005). JPET 313(1):293-301; Hanson et al. (2006). J Med Chem 49(12): 3701-3709; Hanson et al. (2007). J Med Chem 50(16):3928-3936), or SQ29,548, previously described by Ogletree, M. L., Harris, D. N., Greenberg, R., et al. Pharmacological actions of SQ 29,548, a novel selective thromboxane antagonist. J Pharmacol Exp Ther 234 435-441 (1985), were used. SQ29,548 and compound 9ag is commercially available from Cayman (CAY10535) while compound 9h was synthesized based on published methodology.

TABLE 2.1

Reference Compounds

SQ29,548

[Structure of SQ29,548]

Compound 9h

[Structure of Compound 9h]

Compound 9ag

[Structure of Compound 9ag]

Selected reference compounds (e.g. SQ29,548, 9h or 9ag) and compounds of the invention were tested for their ability to inhibit $[Ca^{2+}]_i$ mobilization induced by U46619 (1 μM) in a concentration-dependent manner. Examples of calculated $IC_{50}$ values, defined as the concentration able to inhibit 50% of $[Ca^{2+}]_i$ mobilization, obtained for certain reference or invention compounds when tested in HEK293 cells stably overexpressing TPα (HEK.TPα cells) or TPβ (HEK.TPβ cells) are given in Table 2.2. When such effects of the selected reference and compounds of the invention were tested for antagonism of agonist (U46619)-induced $[Ca^{2+}]_i$ mobilization by the TPα and TPβ isoforms, a selectivity ratio was also determined as the $IC_{50}$ TPα/$IC_{50}$ TPβ. Results collected in this evaluation are presented in Table 2.2.

TABLE 2.2

Effect of TP antagonists on U46619-induced calcium mobilization in HEK.TPα & HEK.TPβ cell lines.

| | $IC_{50}$ data for U46619-mediated $[Ca^{2+}]_i$ mobilization (nM) | | |
|---|---|---|---|
| TP Antagonist | TPα | TPβ | TPα:TPβ Selectivity Ratio |
| Compound 9ag | 1746 | 379 | 4.5 |
| Compound 9h | 612 | 270 | 2.3 |
| XXXVIII | 4006 | 1991 | 2 |
| IX | 11,620 | 1545 | 7.5 |
| XLI | 106 | 16.5 | 6.4 |
| XLIII | 13,020 | 9325 | 1.4 |
| X | 119 | 7.33 | 16.2 |
| XLVI | 114 | 36.5 | 3 |
| XLV | 185.6 | 33.7 | 5.5 |
| XII | 89.8 | 86 | 1 |

Example 2: Ex Vivo Platelet Aggregation

The effects of selected compounds of the invention on agonist-(U46619)-induced platelet aggregation ex vivo was examined.

A modification of the turbidimetric method originally developed by Born & Cross (Born, G. V. and Cross, M. J., The Aggregation of Blood Platelets, J Physiol, 1963, 168: 178-95) is used. The principle is based on the diffraction of the light by particles. When a light beam passes through a suspension of particles, it is diffracted, depending on the number and the size of the particles in suspension.

In the Born & Cross method, a light beam passes through a platelet suspension and the quantity of light is measured by a detector placed after the sample. Upon platelet aggregation, the size of platelet aggregates will increase while the total number of free platelets will decrease. Consequently, less light will be diffracted and the detector will record an increase in light intensity. The aggregometer has been developed based on these concepts. Variations in light transmission recorded by this device reflects the platelet physiology. When an agonist of platelet aggregation is added to a platelet suspension, platelets undergo activation and shape change. This step is characterized by an increase in platelet's apparent volume and thus a decrease of transmitted light. Subsequent platelet aggregation gradually forms aggregates of increasing size. Transmitted light slightly increases until a plateau is reached. The aggregation of platelet can be confirmed after the experiment by visual direct inspection of the test tube.

Preparation of platelet suspension is achieved by blood centrifugation. After the blood is withdrawn from healthy volunteers, it is centrifuged at 160 g for 10 minutes. The platelets rich plasma (PRP) is re-centrifuged at 160 g for 10 min to remove contaminating red and white blood cells. The supernatant which is collected contains the PRP. The remaining blood is subsequently centrifuged at 900 g for 15 min in order to retrieve plasma (platelets poor plasma, PPP). PRP is diluted with PPP to reach a final concentration of $150\times10^3$ platelets/μl. PRP is kept warmed at 37° C. in the aggregometer and the adequate dilution of drug to test is introduced in the sample. Platelet aggregation is induced after 10 minutes incubation.

Light transmission (T) is measured throughout all the experiment, which is ended 8 minutes after induction of aggregation. Maximal light transmission (Tmax) is determined in the sample without drugs. Minimal light transmission (Tmin) is measured in PRP without inducer.

Percentage of platelet aggregation inhibition reflects the drug potency and is given by the following equation:

%=100×(1−((T−Tmin)/(Tmax−Tmin)))

Results are expressed as $IC_{50}$, which is defined as the drug concentration required to inhibit 50% of platelet aggregation. By way of example, the ability of XLI, X, XLVI, XLV and XII compared to the reference compounds is shown in Table 2.3.

Compounds XLI, X, XLVI, XLV and XII have improved efficacy over the reference compounds (see Table 2.3 for summary data) previously identified by Hanson et al. (2007). J Med Chem 50(16):3928-3936).

TABLE 2.3

Effect of TP antagonists on U46619-induced human platelet aggregation ex vivo.

| TP Antagonist | $IC_{50}$ data for inhibition of U46619-induced platelet aggregation (nM) |
|---|---|
| SQ29,548 | 8.33 |
| Compound 9ag | 985 |
| Compound 9h | 513 |
| XLI | 230 |
| X | 4.71 |
| XLVI | 4.12 |
| XLV | 159 |
| XII | 129 |

The method of assessing platelet aggregation also allows evaluation of the effect of the compounds of the invention on platelet aggregation upon stimulation by other agonists, e.g., adenosine diphosphate (ADP) and thrombin. By way of example, the ability of XLI, X, XLVI, XLV and XII to affect ADP and thrombin-induced platelet aggregation of human platelets ex vivo and all compounds of the invention tested did not affect ADP- or Thrombin-induced aggregation.

Example 3: Screening of Compounds

The effects of selected compounds of the invention on agonist-(U46619)-induced platelet aggregation ex vivo was examined.

Figure 1B:
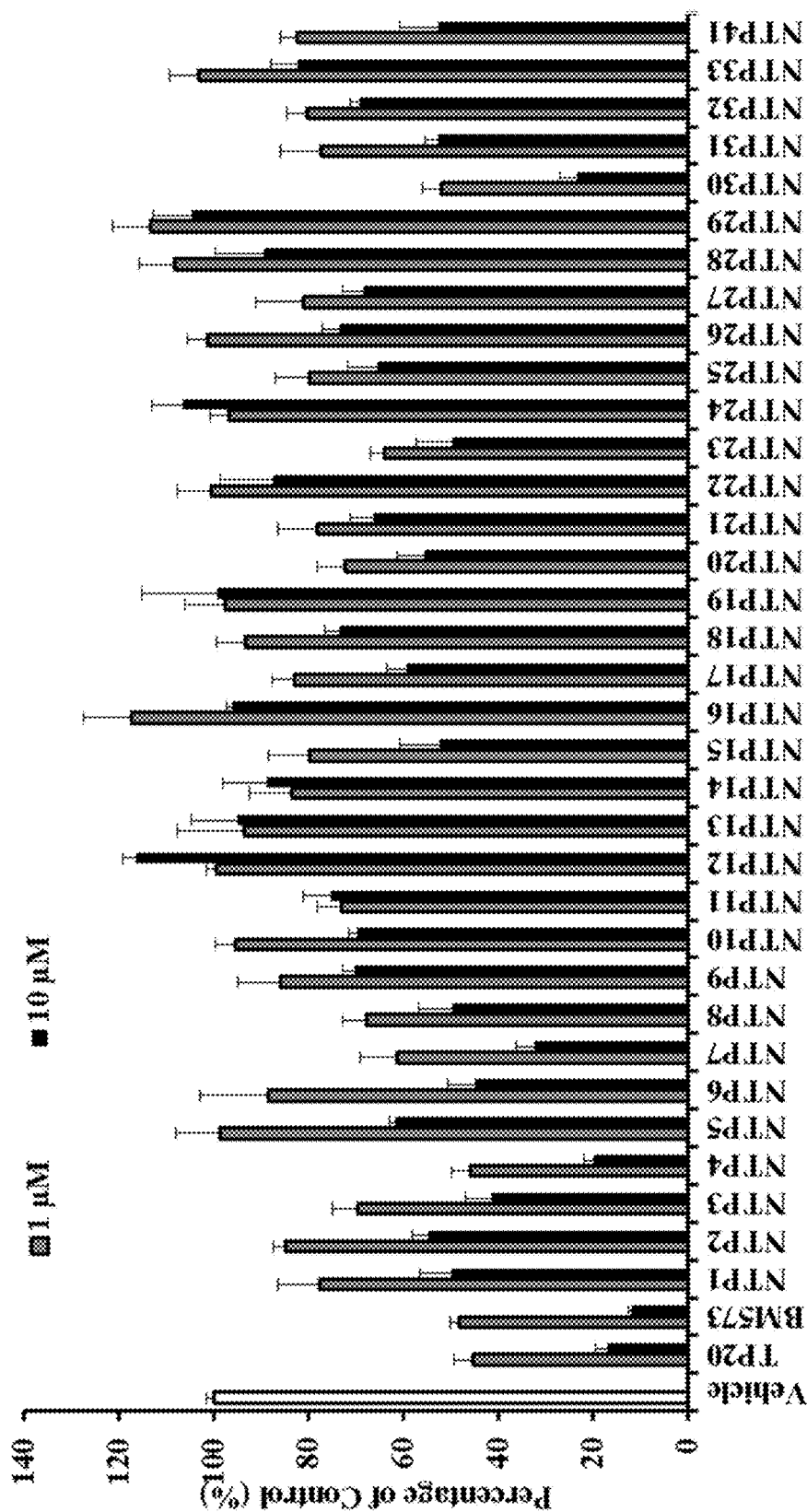

Compounds listed in Table 2.4 were initially screened through calcium mobilisation assays using HEK 293 cells over-expressing the thromboxane (TX)$A_2$ receptor, β isoform (TP3), referred to as HEK.TPβ cells and thereafter, activity was confirmed in HEK.TPα cells over-expressing the αisoform (TPα). The screening involved examining the effect of the compounds, used at 1 and 10 μM concentrations, on calcium mobilised in response to the $TXA_2$ mimetic U46619 (1 μM). The data was compared to compound Formula (X) (i.e., TP20) and the reference TP antagonist BM573 (1) where the results are shown in FIGS. 1A-1B and Table 2.5 (n≥3). Table 2.4 gives the names used in the study for the compounds by formula reference.

TABLE 2.4

Names in study

| Formula | Name |
|---|---|
| XXI | TP1 |
| XIV | TP2 |
| XV | TP3 |
| XVI | TP4 |
| XVII | TP5 |
| XXIV | TP6 |
| XVIII | TP7 |

TABLE 2.4-continued

Names in study

| Formula | Name |
|---|---|
| XIX | TP8 |
| XXVI | TP9 |
| III | TP10 |
| VIII | TP11 |
| XXX | TP12 |
| XXXII | TP13 |
| XXXIV | TP14 |
| XXXVI | TP15 |
| XXXVIII | TP16 |
| IX | TP17 |
| XLI | TP18 |
| XLIII | TP19 |
| X | TP20 |
| XLVI | TP21 |
| XLVII | TP22 |
| XXV | TP23 |
| XXVII | TP24 |
| XXVIII | TP25 |
| XXIX | TP26 |
| XXXI | TP27 |
| XXXIII | TP29 |
| XXXV | TP30 |
| XXXVII | TP31 |
| XXXIX | TP32 |
| XL | TP33 |
| XLII | TP34 |
| L | TP35 |
| LII | TP36 |
| XLIV | TP37 |
| XLV | TP38 |
| XX | TP39 |
| LIV | TP40 |
| LVI | TP41 |
| XLVIII | TP42 |
| XLIX | TP43 |
| LI | TP44 |
| LIII | TP45 |
| XII | TP46 |
| LV | TP47 |
| XI | TP48 |
| LII | NTP1 |
| LXXV | NTP2 |
| XCI | NTP3 |
| LXII | NTP4 |
| LXXIV | NTP5 |
| LXIII | NTP6 |
| LXI | NTP7 |
| XCIV | NTP8 |
| LXX | NTP9 |
| LXXVI | NTP10 |
| LXXXV | NTP11 |
| LXXXVII | NTP12 |
| LXXVIII | NTP13 |
| LXXX | NTP14 |
| LXXXI | NTP15 |
| LXXXII | NTP16 |
| LXXXIII | NTP17 |
| LXIV | NTP18 |
| LXV | NTP19 |
| LXVI | NTP20 |
| LXVII | NTP21 |
| LXXIX | NTP22 |
| LXXXVIII | NTP23 |
| LXXXVI | NTP24 |
| LXXXIV | NTP25 |
| CIX | NTP26 |
| XCIX | NTP27 |
| LXXVII | NTP28 |
| LXVIII | NTP29 |
| CX | NTP30 |
| LVII | NTP31 |
| LVIII | NTP32 |
| LIX | NTP33 |
| LX | NTP41 |
| XXIII | Cay10535 |

CONCLUSIONS

Using the definition of activity as an "Antagonist, when used at 1 µM, that leads to greater than 50% inhibition of TP (1 µM U46619)-induced activity (e.g. $[Ca^{2+}]_i$ mobilization)", a number of compounds were ACTIVE in HEK.TPβ cells, including NTP3 (—$CF_3$), NTP4 (—C≡N), NTP27 (—$SO_2ME$) and the halide variants NTP7 (—Br), NTP8 (—F) & NTP30 (—Cl). Hence, key findings of the SAR that resulted from the synthesis of NTP1-NTP33 & NTP41 are presented here.

In terms of inhibition of TPα/TPβ-induced calcium mobilization in HEK.TPα/HEK.TPβ cell lines, the smaller nitro group replacements, such as —C≡N, the halides (—Br, —Cl & —F), —$CF_3$ and —$SO_2Me$ exhibited good ability to antagonise the TPα/TPβ-mediated calcium responses;

A number of other NTP compounds showed limited efficacy in the calcium mobilisation assays in the HEK.TPα/HEK.TPβ cell lines, i.e., ability to inhibit TP-mediated calcium responses, while others showed no affect. Hence, it was possible to group the NTPs into Active and Inactive compounds. With regard to the ACTIVE NTPs, it was also possible to rank them; however, it remains that the smaller substituents are most effective;

NTP4 (—C≡N), when used at 0.1 µM, showed an ability to inhibit TP-mediated platelet aggregation (in response to the TP agonist U46619) in whole blood platelet aggregation assays.

Determination of $IC_{50}$ values of NTP4 in side-by side comparison in (1) the HEK.TPα/HEK.TPβ cell lines and (2) platelets confirmed that while NTP4 is a potent TP antagonist in terms of its ability to inhibit TP-mediated responses.

While NTP4 (—C≡N) is the most active of the nitro replacements synthesised, substitution of the cyanobenzene ring, as in NTP32 (-methyl group) and NTP33 (pyridyl ring), to change the electrophilicity of the cyano group resulted in loss of activity compared to the cyano compound NTP4 and to the key lead TP20.

(1) Calcium Mobilisation Assays: Screening of NTP compounds in HEK.TPβ & HEK.TPα cells FIG. 1 shows the effect of the TP antagonist compounds of the invention on U46619-mediated calcium mobilization in HEK.TPα and HEK.TPβ cells. HEK.TPβ (FIG. 1A) and HEK.TPα (FIG. 1B) cells, preloaded with Fluo-4, were incubated with the TP20 (Batch#4), BM573, NTP1-NTP33 and NTP 41 where each antagonist was used at 1 & 10 µM, as indicated, prior to stimulation with 1 µM U46619. Data is presented as the mean (±S.E.M.) percentage of the agonist-induced response in vehicle-treated cells (Percentage of Control; %) and represents data from at least 3 independent experiments were cells were treated in duplicate.

TABLE 2.5

Summary of Calcium Data from Screening Assays.

| TP Antagonist | TPα 1 µM | TPα 10 µM | TPβ 1 µM | TPβ 10 µM |
|---|---|---|---|---|
| TP20 | 45.4 ± 4.07 | 17.1 ± 2.46 | 12.6 ± 1.46 | 9.96 ± 1.70 |
| BM573 | 48.5 ± 1.77 | 12.0 ± 0.76 | 23.8 ± 0.68 | 9.90 ± 1.80 |
| NTP1 | 77.8 ± 8.71 | 50.2 ± 6.39 | 101 ± 4.75 | 102 ± 4.15 |
| NTP2 | 85.0 ± 2.71 | 54.9 ± 3.32 | 102 ± 3.59 | 90.1 ± 2.78 |
| NTP3 | 69.6 ± 5.92 | 41.6 ± 5.45 | 46.0 ± 5.92 | 14.8 ± 2.44 |
| NTP4 | 46.1 ± 3.87 | 19.9 ± 2.13 | 22.5 ± 3.70 | 10.2 ± 0.95 |
| NTP5 | 98.7 ± 9.29 | 61.7 ± 1.42 | 88.3 ± 5.27* | 72.0 ± 3.87* |
| NTP6 | 88.6 ± 14.5 | 45.1 ± 5.75 | 94.4 ± 7.70 | 57.4 ± 6.86 |
| NTP7 | 61.5 ± 7.70 | 32.5 ± 3.95 | 49.0 ± 4.41 | 12.2 ± 1.93 |

TABLE 2.5-continued

Summary of Calcium Data from Screening Assays.

| TP Antagonist | TPα 1 µM | TPα 10 µM | TPβ 1 µM | TPβ 10 µM |
|---|---|---|---|---|
| NTP8 | 68.0 ± 5.05 | 49.9 ± 6.91 | 5.94 ± 1.85 | 14.6 ± 2.72 |
| NTP9 | 85.9 ± 9.13 | 70.4 ± 2.47 | 46.3 ± 7.33 | 12.2 ± 1.03 |
| NTP10 | 95.5 ± 4.25 | 69.8 ± 1.73 | 96.0 ± 0.94 | 54.7 ± 8.10 |
| NTP11 | 73.1 ± 5.28 | 75.4 ± 5.83 | 49.8 ± 1.86 | 20.7 ± 2.81 |
| NTP12 | 99.7 ± 2.13 | 77.9 ± 2.69 | 84.2 ± 7.51 | 34.4 ± 2.85 |
| NTP13 | 93.8 ± 13.9 | 95.2 ± 9.57 | 74.0 ± 3.66 | 36.2 ± 0.52 |
| NTP14 | 83.5 ± 9.26 | 89.1 ± 9.10 | 86.4 ± 7.06 | 59.4 ± 7.67 |
| NTP15 | 79.8 ± 8.81 | 52.6 ± 8.42 | 87.6 ± 8.28 | 86.1 ± 5.64 |
| NTP16 | 117 ± 10.2 | 96.3 ± 1.24 | 83.0 ± 7.62 | 34.0 ± 3.88 |
| NTP17 | 83.1 ± 4.85 | 59.5 ± 4.07 | 51.1 ± 1.13 | 13.3 ± 5.91 |
| NTP18 | 93.4 ± 6.17 | 73.6 ± 2.98 | 45.0 ± 4.34 | 22.6 ± 2.28 |
| NTP19 | 97.6 ± 8.60 | 99.4 ± 16.0 | 77.7 ± 3.24 | 64.5 ± 4.65 |
| NTP20 | 72.4 ± 5.97 | 55.7 ± 5.84 | 42.5 ± 2.32 | 18.5 ± 3.53 |
| NTP21 | 78.3 ± 8.28 | 66.4 ± 4.95 | 51.0 ± 1.62 | 32.2 ± 2.89 |
| NTP22 | 101 ± 7.28 | 87.6 ± 11.3 | 85.1 ± 4.38 | 50.1 ± 4.06 |
| NTP23 | 64.2 ± 2.89 | 49.9 ± 7.61 | 4.84 ± 2.75 | 20.4 ± 1.94 |
| NTP24 | 96.8 ± 3.94 | 107 ± 6.48 | 87.7 ± 8.18 | 37.9 ± 2.61 |
| NTP25 | 80.0 ± 7.15 | 65.5 ± 6.32 | 61.6 ± 1.93 | 14.8 ± 2.03 |
| NTP26 | 101 ± 4.30 | 73.7 ± 3.56 | 68.6 ± 3.30 | 41.0 ± 3.88 |
| NTP27 | 81.1 ± 10.2 | 68.4 ± 4.56 | 36.4 ± 3.80 | 16.3 ± 2.39 |
| NTP28 | 108 ± 7.64 | 89.5 ± 10.3 | 110 ± 1.85 | 62.3 ± 4.30 |
| NTP29 | 113 ± 8.15 | 105 ± 8.03 | 100 ± 4.69 | 94.6 ± 3.58 |
| NTP30 | 52.2 ± 3.90 | 23.3 ± 3.63 | 46.5 ± 5.86 | 9.31 ± 1.57 |
| NTP31 | 77.3 ± 8.72 | 52.7 ± 2.89 | 74.8 ± 5.49 | 27.7 ± 4.21 |
| NTP32 | 80.3 ± 4.21 | 69.3 ± 2.07 | 93.6 ± 4.06 | 46.2 ± 4.83 |
| NTP33 | 103 ± 6.25 | 82.4 ± 5.86 | 75.6 ± 6.46 | 34.5 ± 1.56 |
| NTP41 | 82.6 ± 3.41 | 52.8 ± 8.03 | 72.2 ± 5.66 | 18.8 ± 1.77 |

Note that reference compound BM573 is shown by Formula (CXI). Also see Rolin, S., Dogne, J. M., Michaux, C., Delarge, J., and Masereel, B. (2001) Prostaglandins Leukot Essent Fatty Acids 65, 67-72.

(CXI)

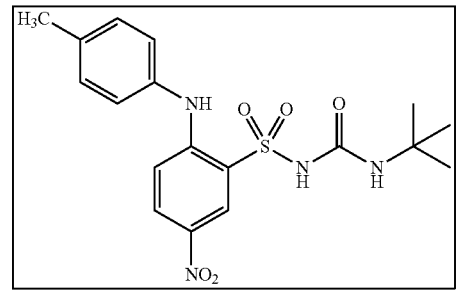

TP20 has been identified as a key lead compound. Consistent with this, at 1 & 10 µM concentrations, TP20 potently inhibited U46619-mediated calcium mobilization in HEK.TPβ cells, where responses were reduced by approx. 90%. Likewise, the reference compound BM573, potently inhibited U46619-mediated responses at the concentrations tested. Of the NTP compounds NTP1-NTP33 & NTP41, a number showed good antagonist activity, including NTP3 and NTP4.

Active compounds that showed ≥50% inhibition of U46619-mediated responses in HEK.TPβ cells were subject to further characterization through both calcium and platelet aggregation assays. These compounds include NTP3 (—CF3), NTP4 (—C≡N), NTP7 (—Br), NTP8 (—F), NTP9 (—COMe), NTP11 (amide), NTP17 (amide), NTP18 (C-linked palladium chemistry), NTP20 (C-linked palladium chemistry), NTP21 (C-linked palladium chemistry), NTP23 (amide), NTP25 (amide) and NTP27 (—SO2Me).

111

Initially, the ability of the selected ACTIVE compounds listed above to inhibit U46619-mediated calcium responses in HEK.TPβ cells was examined, where the concentration were reduced to 0.5 μM and 1 μM, such that the compounds could be ranked in terms of activity.

Figure 2:
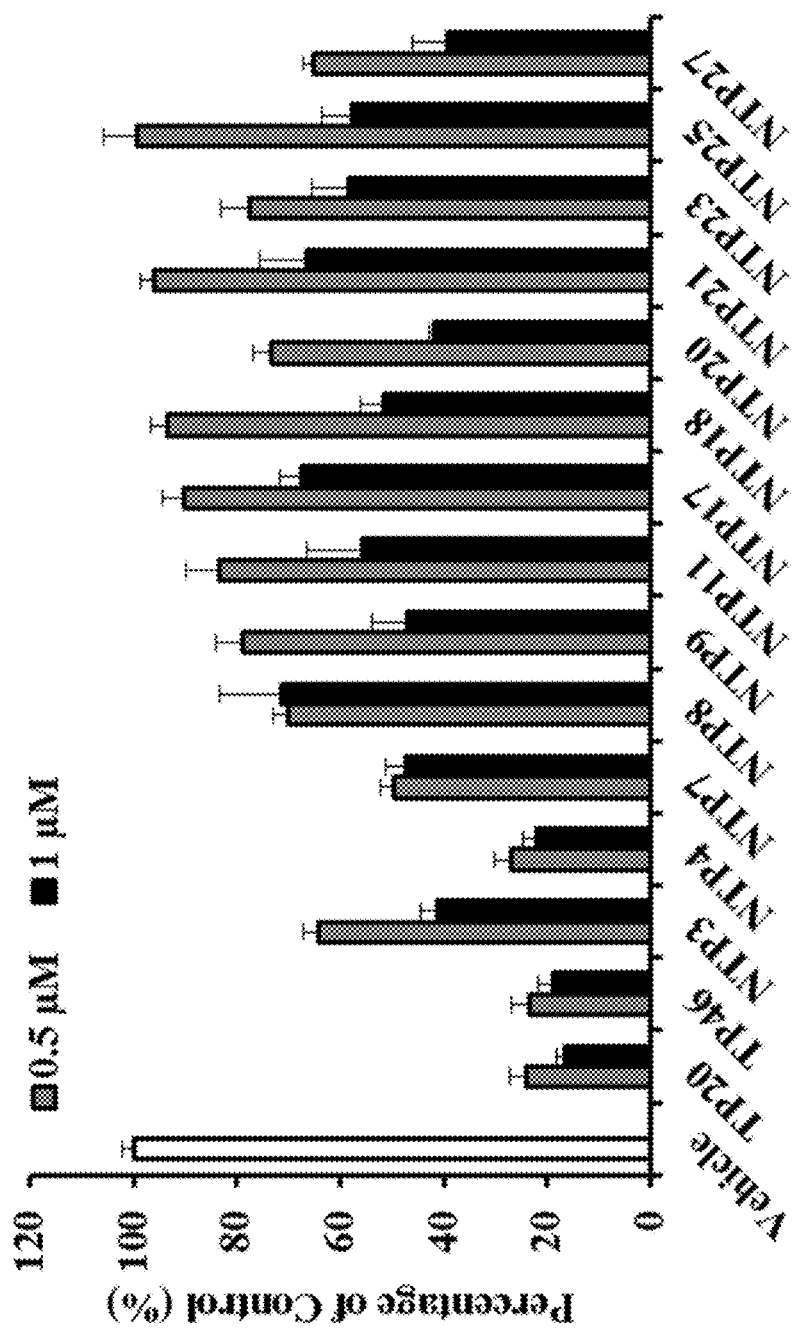
FIG. 2 shows the effect of the TP antagonists on U46619-mediated calcium mobilization in HEK.TPβ cells.

FIG. 2 shows the effect of the TP antagonists on U46619-mediated calcium mobilization in HEK.TPβ cells. HEK.TPβ cells, preloaded with Fluo-4, were incubated with the TP20 and the selected ACTIVE NTP compounds, where each antagonist was used at 0.5 or 1 μM, as indicated, prior to stimulation with 1 μM U46619. Data is presented as the mean (±S.E.M.) percentage of the agonist-induced response in vehicle-treated cells (Percentage of Control; %) and represents data from 4 independent experiments were cells were treated in duplicate.

The selected NTP compounds were ranked based on the data from the calcium responses in HEK.TPβ cells where cells were treated with 0.5 μM of the compound. The compounds, in order in decreasing potency, include NTP4>NTP7>NTP3>NTP27>NTP8>NTP20>NTP23>NTP9>NTP11>NTP17>NTP18>NTP21>NTP25.

It is noteworthy that the smaller nitro group replacements, such as —C≡N, —Br, —CF3, —SO2Me and —F exhibit the greatest ability to antagonize the TPβ-mediated calcium responses. NTP4 exhibited greater than 50% inhibition of U46619-mediated responses when used at 0.5 μM, similar to the previously identified TP20 and TP46. Hence, IC50 value for inhibition of U46619-mediated responses was determined in side-by-side comparison with TP20.

Example 4: Determination of IC50 Values for Inhibition of TP-Mediated [Ca2+]i Mobilization Determination of IC50 values for NTP4 and TP20, in side-by-side comparison, has been performed in both HEK.TPα and HEK.TPβ cells. Table 2.6 shows the results, where n=5 and n=6 for HEK.TPα and HEK.TPβ, respectively.

TABLE 2.6

$IC_{50}$ values for inhibition of U46619-mediated calcium mobilization in HEK.TPα and HEK.TPβ cells.

| TP Antagonist | $IC_{50}$ values for inhibition of U46619-mediated $[Ca^{2+}]_i$ (nM) | |
|---|---|---|
| | TPα | TPβ |
| TP20 (—NO$_2$) | 240 ± 29.8 | 9.61 ± 1.46 |
| NTP4 (—C≡N) | 593 ± 83.6 | 60.4 ± 8.00 |

NTP4 and TP 20 are potent compounds.

Example 5: (2) Ex Vivo Platelet Aggregation Assays (A) Screening of ACTIVE NTP Antagonists: Whole Blood Aggregation Assays In order to evaluate the NTP compounds in a second independent assay, the effect of the ACTIVE NTP compounds (i.e., those compounds, when used at 1 μM, that exhibited ≥50% inhibition of TP (1 μM U46619)-induced activity in the initial screening calcium mobilization assays) on U46619-mediated platelet aggregation assays was examined. From an efficacy point of view, this is an important assay and, physiologically, relevant with respect to the therapeutic target.

Initially, the Sysmex haematological analyzer was used to examine the effect of the TP antagonists at a single concentration (0.1 μM) on U46619 (1 μM)-mediated platelet aggregation in whole blood.

112

Figure 3:
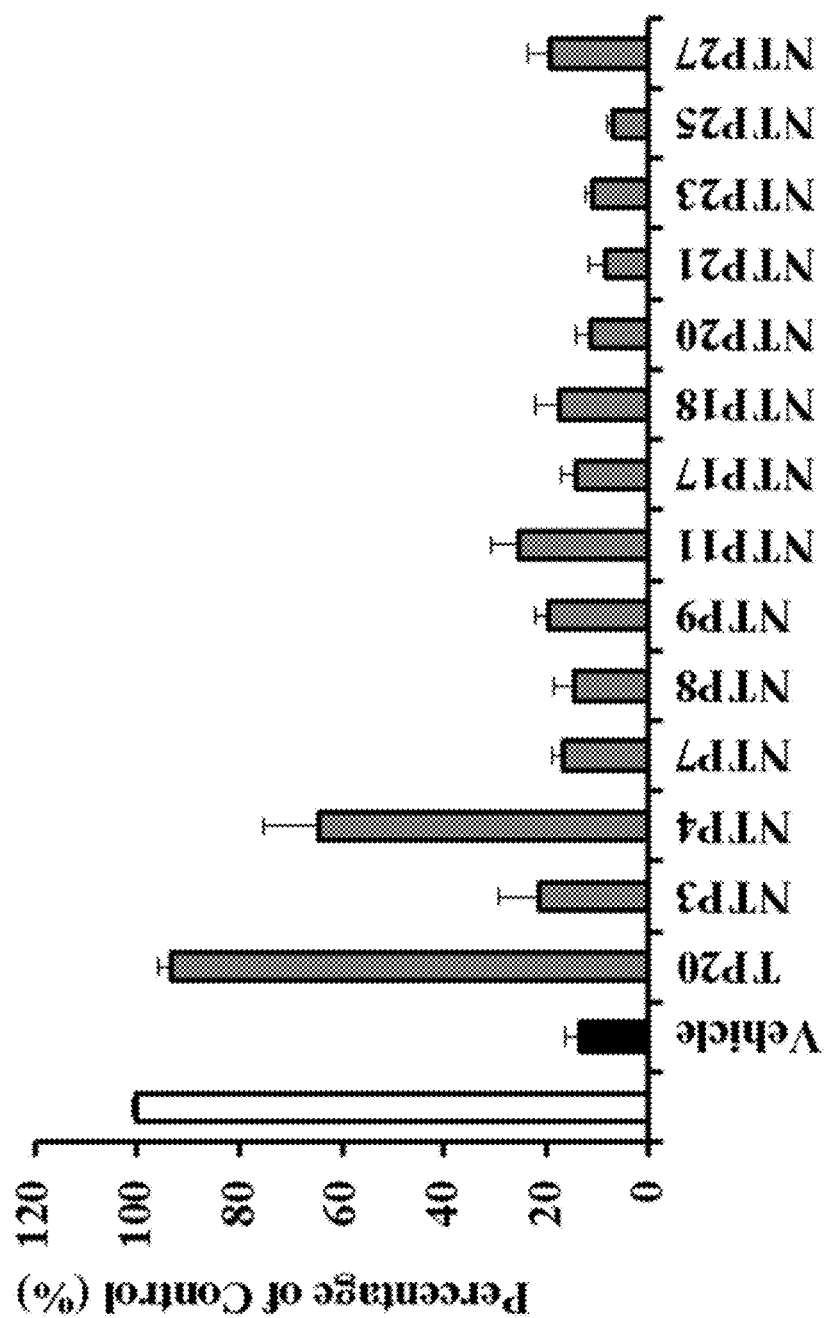
FIG. 3 illustrates effects of the TP antagonist compounds on U46619-mediated platelet aggregation.

FIG. 3 illustrates effects of the TP antagonist compounds on U46619-mediated platelet aggregation. Blood was taken form healthy volunteer by venupuncture into syringes containing 3.8% sodium citrate, 10 μM Indomethacin, such that the ratio of anticoagulant: blood was 1:9. The blood was aliquoted and incubated for 10 min with TP20 and selected NTP compounds, as indicated, where the antagonist were used at 0.1 μM prior to stimulation with 1 μM U46619 for 3 min. The blood was fixed with formaldehyde and platelet numbers counted using the Sysmex haematological analyzer. Data is presented as the mean percentage of control or non-treated blood sample (Percentage of Control; %) and represent data from 3 independent experiments were samples were treated in duplicate.

Consistent with previous data, the identified lead compound TP20, at 0.1 μM, almost completely inhibited the reduction in platelet numbers caused by U46619-mediated platelet aggregation. NTP4 (0.1 μM) in some cases consistently inhibited the U46619-mediated reduction in platelet number by approx. 50%.

(B) Determination of IC50 Values for Inhibition of TP-Mediated Platelet Aggregation The effect of NTP4 and the previously identified lead TP antagonist, TP20, on U46619-mediated platelet aggregation in side-by-side comparisons was performed in platelet rich plasma (PRP) using the PAP-8E platelet aggregometer.

Table 2.7 shows the effect of TP Antagonists on U46619-mediated platelet aggregation and gives a summary of IC50 values for inhibition of U46619-mediated platelet aggregation.

TABLE 2.7

Effect of TP Antagonists on U46619-Mediated Platelet Aggregation: Summary of $IC_{50}$ Values for Inhibition of U46619-Mediated Platelet Aggregation.

| TP Antagonist | $IC_{50}$ Value for Inhibition of U46619-Mediated Platelet Aggregation (Mean ± S.E.M.; nM) |
|---|---|
| TP20 (Batch #4) | 4.62 ± 0.72 |
| NTP4 (Batch #2) | 40.3 ± 7.08 |

Note figures are based on data from >6 independent experiments.

Figure 4A:
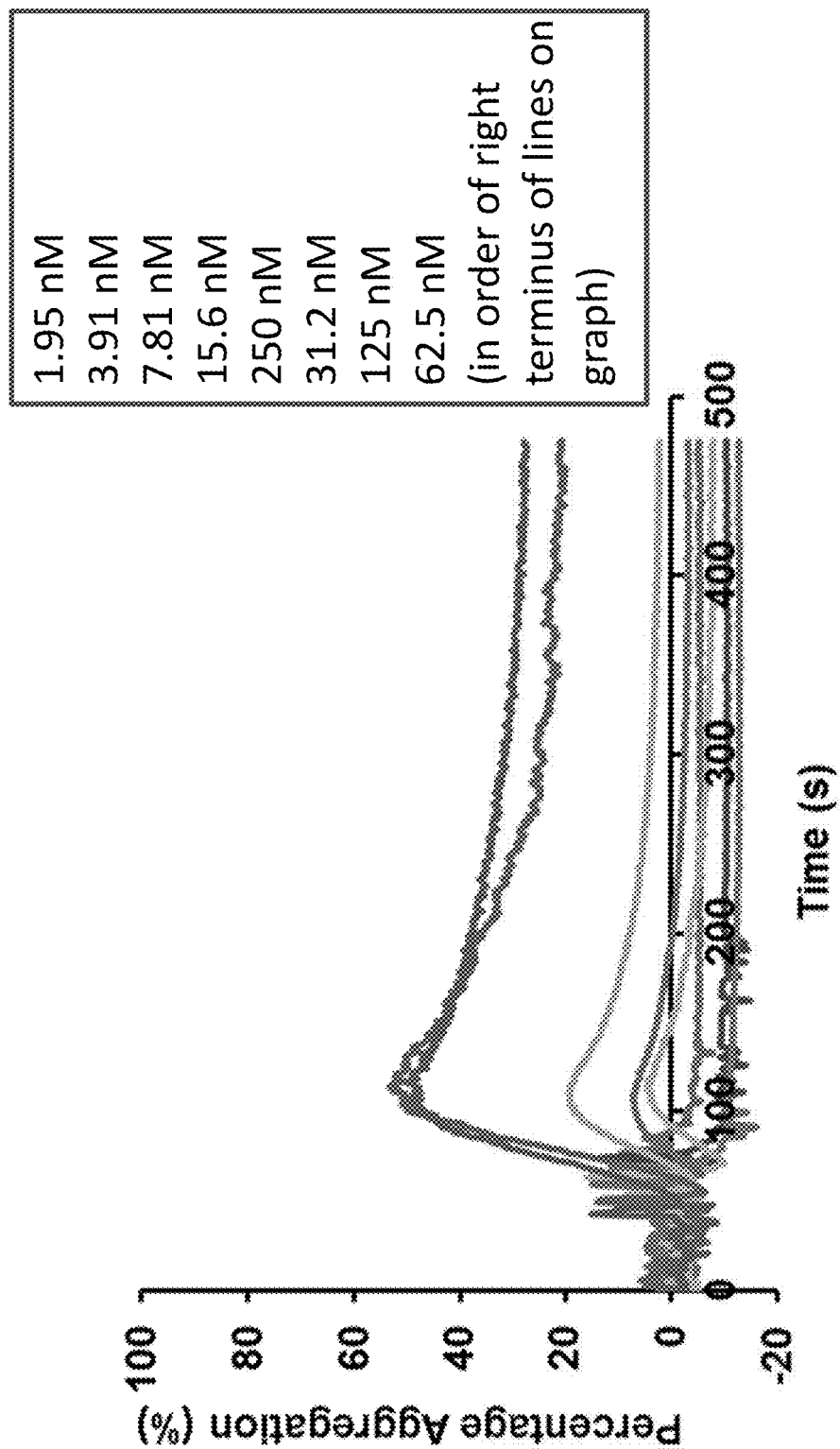
FIGS. 4A-4C show the effect of TP20 & NTP4 on U46619-mediated platelet aggregation
Figure 4B:
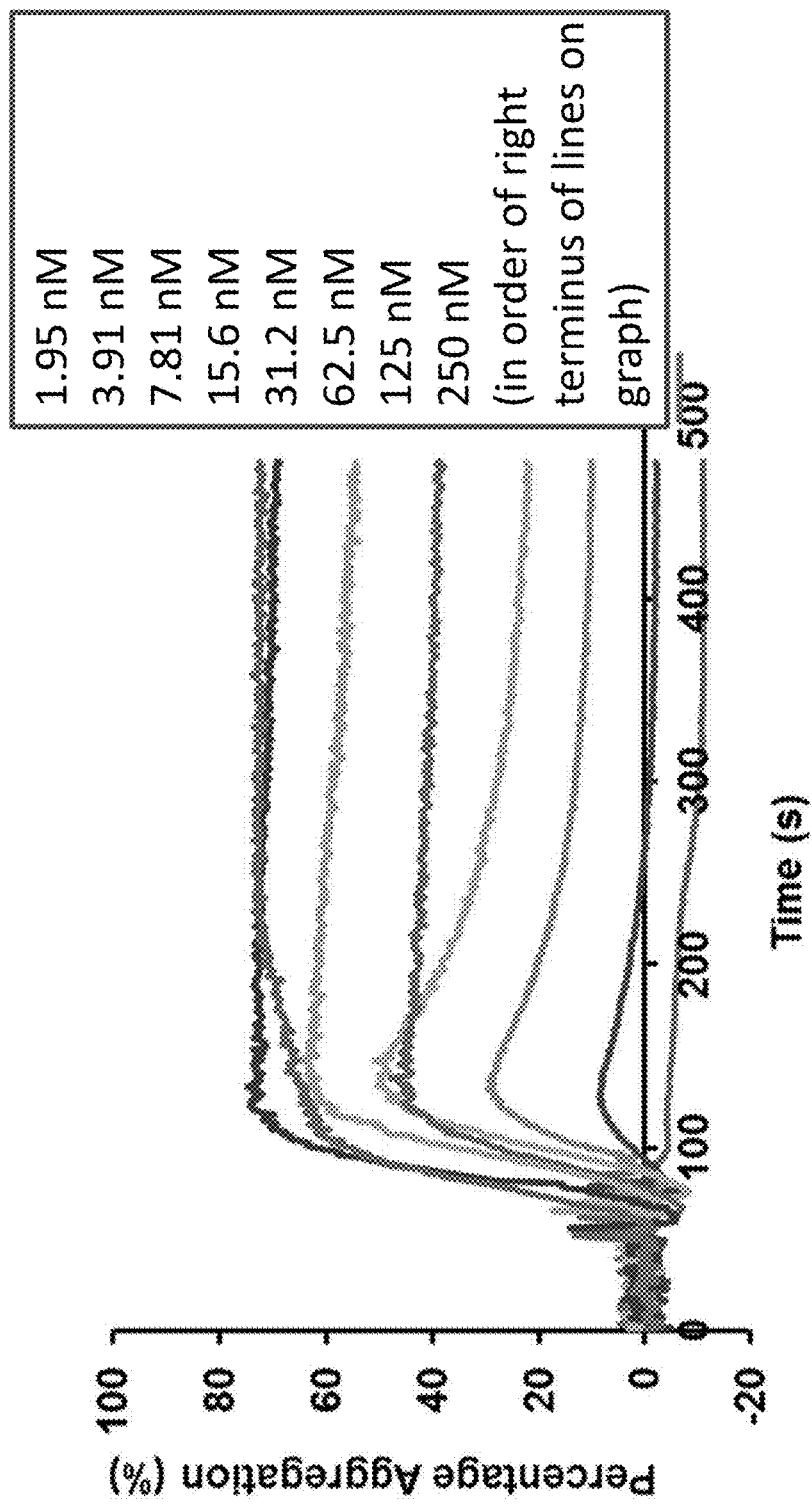
Figure 4C:
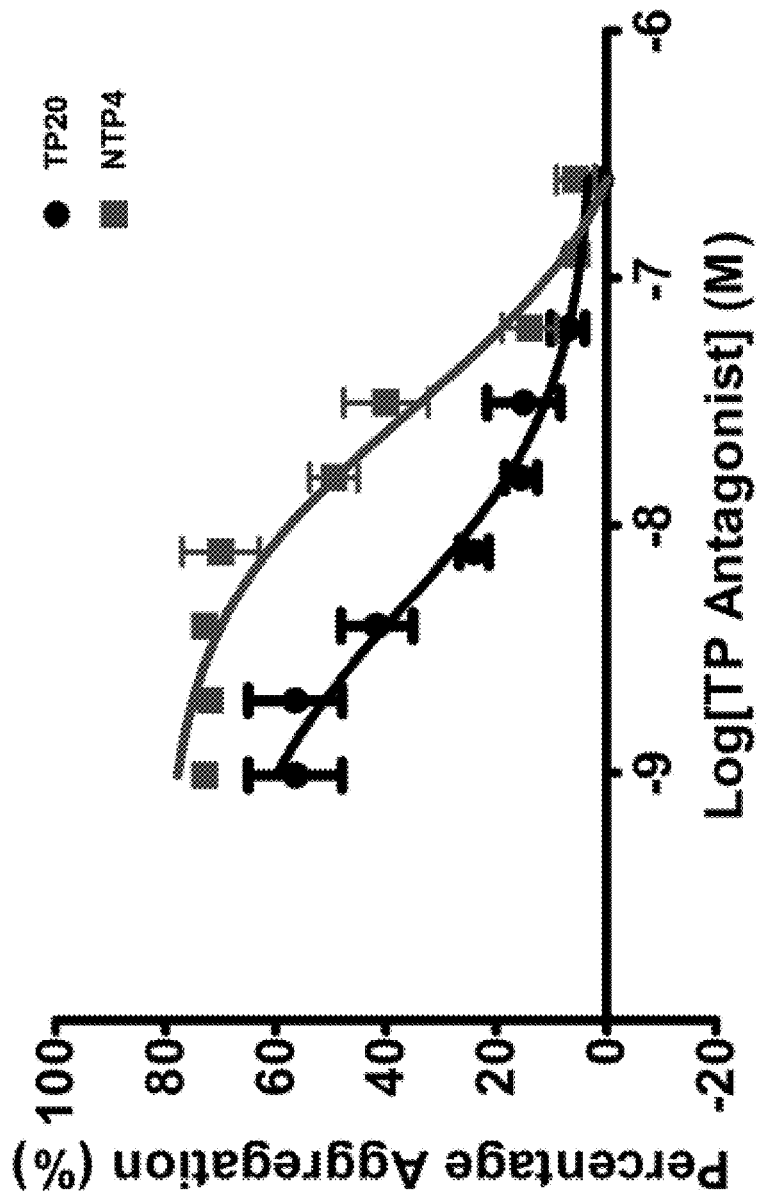

FIG. 4A-4C show the effect of TP20 & NTP4 on U46619-mediated platelet aggregation. PRP was prepared from blood taken from healthy volunteers into syringes containing 3.8% sodium citrate and 10 M indomethacin such that the final ratio of anticoagulant to blood was 1:9. Aliquots of PRP (300 al) were pre-incubated for 10 min with the TP antagonists, TP20 and NTP4, where 2-fold serial dilutions from 1 μM were prepared for each, prior to stimulating platelets with 1 μM U46619, incubated at 37° C., with stirring. FIG. 4A and FIG. 4B: Representative dose-response platelet aggregation profiles for TP20 (FIG. 4A) and NTP4 (FIG. 4B), where data is presented as Percentage Aggregation, as determined by changes in light transmission using the PAP-8E Platelet Aggregation Profiler as a function of time. FIG. 4C: The dose-response curves for platelet aggregation are presented as the mean (±S.E.M.) maximum Percentage Aggregation as a function of the log of the TP antagonist concentration. Data presented is representative of >6 independent experiments.

In side-by-side dose-response assays, TP20 is a potent TP antagonist with IC50=4.62±0.72 nM (n=7) for inhibition of U46619-mediated platelet aggregation. NTP4 is approx.

ten-fold less potent than TP20 with IC50=41.5±7.69 nM (n=6) for inhibition of U46619-mediated platelet aggregation.

What is claimed is:

1. A compound of formula:

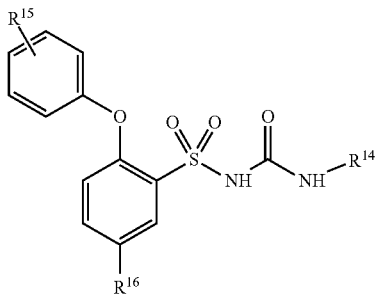

wherein:
R$^{14}$ is an alkyl group;
R$^{15}$ is selected from the group consisting of

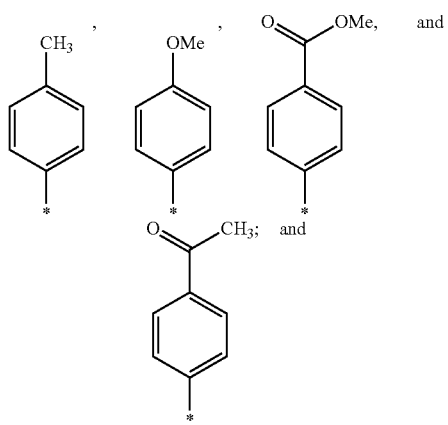

R$^{16}$ is selected from the group consisting of —NO$_2$ and —CN,
or a pharmaceutically acceptable salt thereof.

2. The compound of claim 1, wherein R$^{16}$ is —NO$_2$.

3. The compound of claim 2, wherein R$^{15}$ is

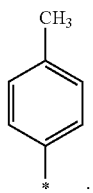

4. The compound of claim 3, wherein R$^{14}$ is selected from the group consisting of an isopropyl group, a pentyl group, a tert-butyl group, and a cyclohexyl group.

5. The compound of claim 2, wherein R$^{15}$ is

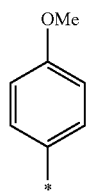

6. The compound of claim 3, wherein R$^{14}$ is selected from the group consisting of an isopropyl group, a pentyl group, a tert-butyl group, and a cyclohexyl group.

7. The compound of claim 2, wherein R$^{15}$ is

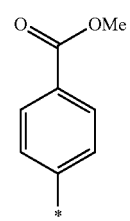

8. The compound of claim 7, wherein R$^{14}$ is selected from the group consisting of an isopropyl group, a pentyl group, a tert-butyl group, and a cyclohexyl group.

9. The compound of claim 2, wherein R$^{15}$ is

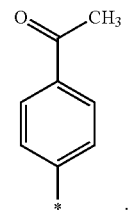

10. The compound of claim 9, wherein R$^{14}$ is selected from the group consisting of an isopropyl group, a pentyl group, a tert-butyl group, and a cyclohexyl group.

* * * * *